United States Patent
Watson et al.

(10) Patent No.: US 9,212,996 B2
(45) Date of Patent: Dec. 15, 2015

(54) ANALYZING AND CORRELATING SPECTRA, IDENTIFYING SAMPLES AND THEIR INGREDIENTS, AND DISPLAYING RELATED PERSONALIZED INFORMATION

(71) Applicant: TellSpec Inc., Toronto (CA)

(72) Inventors: William Stephen Watson, Toronto (CA); Isabel De Oliveira Correa, Toronto (CA)

(73) Assignee: Tellspec, Inc., Toronto, Ontario (CA)

( * ) Notice: Subject to any disclaimer, the term of this patent is extended or adjusted under 35 U.S.C. 154(b) by 0 days.

(21) Appl. No.: 13/958,909

(22) Filed: Aug. 5, 2013

(65) Prior Publication Data
US 2015/0036138 A1 Feb. 5, 2015

(51) Int. Cl.
*G01N 21/25* (2006.01)
*G01N 21/65* (2006.01)
(Continued)

(52) U.S. Cl.
CPC .............. *G01N 21/65* (2013.01); *G01N 21/31* (2013.01); *G01N 21/64* (2013.01); *G01N 2021/6493* (2013.01); *G01N 2201/0221* (2013.01); *G01N 2201/129* (2013.01); *G01N 2201/1293* (2013.01)

(58) Field of Classification Search
CPC .............. G01J 3/46; G01J 3/02; G01J 3/463; G01J 3/501; G01J 3/0272; G01J 3/513; G01N 21/255; G01N 21/25; G01N 21/314; G01N 21/3577
USPC ............ 356/402, 425, 405, 407, 73; 250/226; 702/22, 19
See application file for complete search history.

(56) References Cited

U.S. PATENT DOCUMENTS 6,431,446 B1 * 8/2002 Gu .............................. G01J 3/28
235/454
8,310,672 B2 11/2012 Schmidt et al.
(Continued)

FOREIGN PATENT DOCUMENTS

| WO | WO03027619 | 3/2003 |
| WO | WO03083419 | 10/2003 |
| WO | 2013065035 | 5/2013 |

OTHER PUBLICATIONS

International Search Report for PCT/IB14/63642, Oct. 21, 2014, 5 pgs.

(Continued)

*Primary Examiner* — Tarifur Chowdhury
*Assistant Examiner* — Mohamed K Amara
(74) *Attorney, Agent, or Firm* — Phillips Ryther & Winchester; John P. Davis

(57) ABSTRACT

Obtaining two spectra from the same sample under two different conditions at about the same time for comparison, where at least one of the spectra measures magnitudes of electromagnetic radiation on at least four different ranges or weightings of wavelengths or frequencies. Classifying a sample using these spectra obtained by a user, and using spectra obtained from different samples by different users to identify the sample. Computing correlations between data related to food and ingredient consumption by one or more users over time, and data related to passive personal log data, user entered feedback, user interaction data or personal information related to those users, and detecting: foods or ingredients to which a user may be allergic or intolerant; a possible medical condition of a user; a possible link between food and ingredient consumption and a medical or health condition; or a similarity between at least two such users.

9 Claims, 27 Drawing Sheets

(51) Int. Cl.
  *G01N 21/31* (2006.01)
  *G01N 21/64* (2006.01)

(56) References Cited

U.S. PATENT DOCUMENTS

| | | | |
|---|---|---|---|
| 8,417,014 B2 | 4/2013 | Bolea | |
| 2005/0083293 A1* | 4/2005 | Dixon | G09G 3/3413 345/102 |
| 2005/0154539 A1* | 7/2005 | Butler | G01J 3/28 702/22 |
| 2006/0200320 A1* | 9/2006 | Al-Murrani | 702/20 |
| 2008/0045464 A1* | 2/2008 | Kannar et al. | 514/23 |
| 2010/0049546 A1* | 2/2010 | Neville | 705/3 |
| 2010/0241357 A1 | 9/2010 | Chan et al. | |
| 2010/0309454 A1* | 12/2010 | Zhang | G01J 3/02 356/39 |
| 2012/0201948 A1* | 8/2012 | Huber | 426/637 |
| 2012/0321759 A1* | 12/2012 | Marinkovich et al. | 426/231 |
| 2014/0082854 A1* | 3/2014 | Landa et al. | 8/405 |
| 2014/0236494 A1* | 8/2014 | Kolandaivelu et al. | 702/19 |

OTHER PUBLICATIONS

Written Opinion for PCT/IB14/63642, Oct. 21, 2014, 6 pgs.

* cited by examiner

| Food ID | Parent Food ID | Food 1 ID % | Food 2 ID % | Food 3 ID % | ... | Middle Level ? | Public Good? | Good Bad? | Facts | Alternates |
|---------|----------------|-------------|-------------|-------------|-----|----------------|--------------|-----------|-------|------------|
|         |                |             |             |             |     |                |              |           |       |            |
|         |                |             |             |             |     |                |              |           |       |            |
|         |                |             |             |             |     |                |              |           |       |            |
|         |                |             |             |             |     |                |              |           |       |            |
|         |                |             |             |             |     |                |              |           |       |            |
|         |                |             |             |             |     |                |              |           |       |            |

Food Database 2000

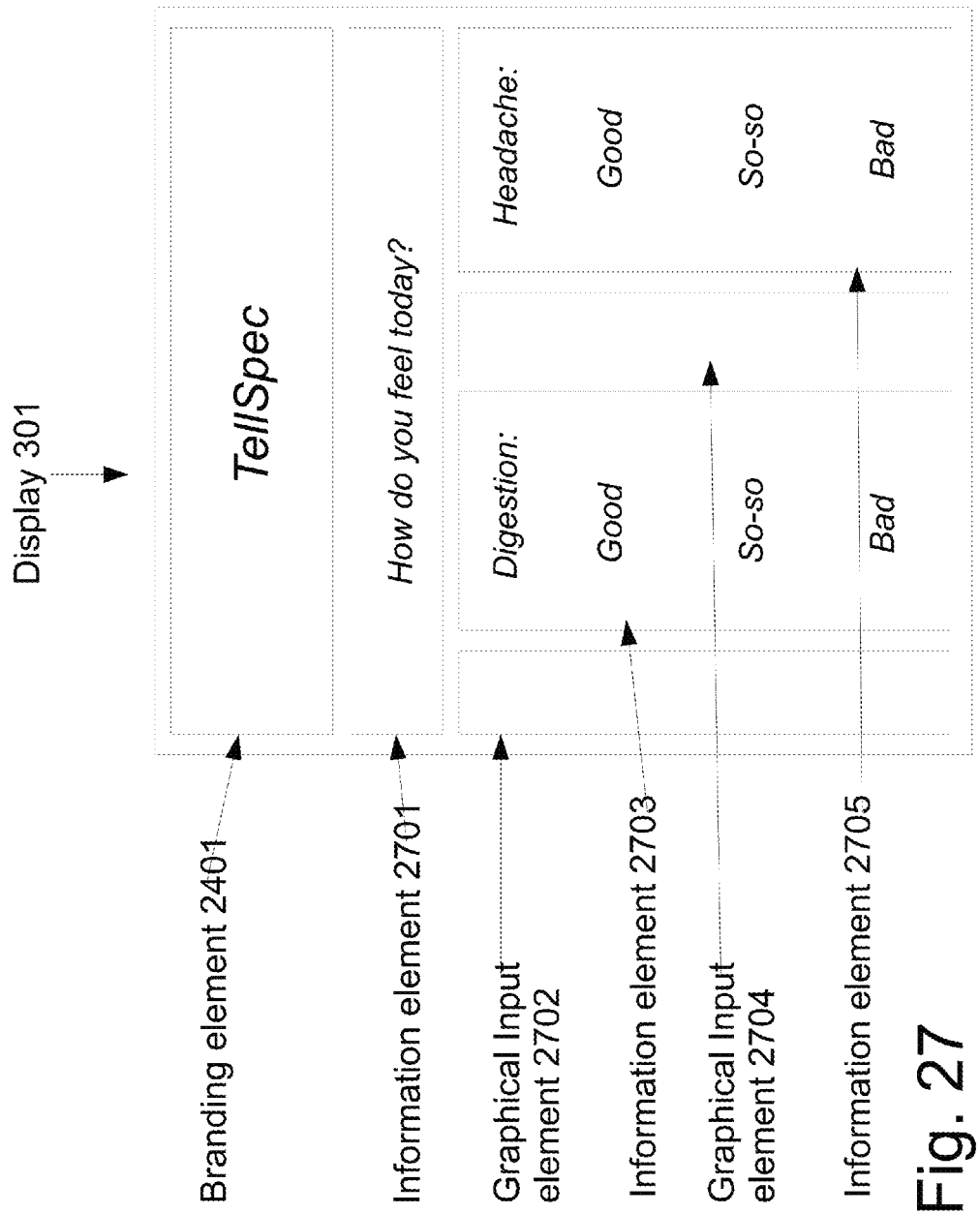

ANALYZING AND CORRELATING SPECTRA, IDENTIFYING SAMPLES AND THEIR INGREDIENTS, AND DISPLAYING RELATED PERSONALIZED INFORMATION

BACKGROUND OF THE INVENTION (1) Field of the Invention

The present invention relates generally to identifying, analyzing, or correlating materials and users through their intensive and/or extensive properties, as detected through scans or spectra, and providing to and receiving from users information related to materials and/or users.

(2) Description of the Related Art

The approaches described in this section are approaches that could be pursued, but not necessarily approaches that have been previously conceived or pursued. Therefore, unless otherwise indicated, the approaches described in this section may not be prior art to the claims in this application and are not admitted to be prior art by inclusion in this section.

Systems for capturing the Raman or other spectrum of a chemical are generally intended for laboratory use or for use by trained personnel in specialized applications such as the manufacture of pharmaceuticals. These spectrometers use a free-space design, in which light travels in air between lenses, gratings and detectors. These systems are bulky, difficult to use, and expensive.

Such systems often perform the analysis in the microprocessor inside the device with reference to a local library stored within the device. This limits the complexity of the calculations, the breadth and depth of the database, and the ease with which the software and the database can be updated.

Such systems usually perform the analysis by finding the closest match in the database, but this approach does not work well with mixtures rather than pure chemical compounds. In such systems, usually reference is made neither to orthogonalizations of one spectrum against another nor to the relative distances between potential matches themselves, and this approach tends to lead to closest matches which are incorrect.

Other systems identify a sample by scanning a bar code or typing in a UPC or EAN. This approach does not work when the original packaging for the sample is no longer available or not convenient to access. This approach also relies on the correctness of the metadata associated with the sample, which is not guaranteed. This approach also fails to detect differences between samples with the same metadata, such as spoiled food.

Systems for presenting information about Raman and other spectra are often designed for experienced scientists who can interpret the spectrum of a chemical, deduce the likely molecular structure of the chemical compound, and guess the identity of the chemical. Even when automated identification is successful, the information is often then presented in a form suitable only for trained chemists.

Systems for identifying a mixture, for example from the universal product code of a product provide little or no information about the composition of the mixture, except for that provided by the manufacturer, when this is available. These lists of ingredients are regulated by institutions such as the FDA, which allows these lists to be incomplete, ambiguous, or even misleading.

BRIEF SUMMARY OF THE INVENTION

The present invention is directed to improvements in identifying substances or materials, and their constituents or ingredients, and in finding relationships between the consumption of, or exposure to, such substances, and a person's health or medical condition, and related matters. Improvements in identifying are accomplished by obtaining and comparing spectra from the same sample under at least two different conditions at about the same time, where at least one spectrum measures magnitudes of electromagnetic radiation on at least four different ranges or weightings of wavelengths, like in the field of spectrometry. Improvements in identifying are also accomplished by comparing the spectra of a substance or material with the compared spectra obtained from previous samples. Improvements in identifying constituents or ingredients are accomplished by first classifying the spectra of a substance or material and then using spectra obtained from different samples in the same class. Other improvements in identifying are accomplished in manners set out in the detailed description.

Improvements in finding relationships are accomplished by computing correlations between data related to food and ingredient consumption by a user over time, and data related to passive personal log data, user entered feedback, user interaction data or personal information related to that user, and detecting foods or ingredients to which that user may be allergic or intolerant or a possible medical condition of that user, and then comparing, aggregating, and correlating such relationships and correlations across a population of users to find similarities between users and possible links between food and ingredient consumption and a medical or health condition. Other improvements in finding relationships are accomplished in manners set out in the detailed description.

The present invention, together with attendant objects and advantages, will be best understood with reference to the detailed description below read in conjunction with accompanying drawings.

BRIEF DESCRIPTION OF THE SEVERAL VIEWS OF THE DRAWINGS

FIG. 27 illustrates a user interface, through the use of which the user can input information about the user's current health and well-being, presented as a linear scale.

DETAILED DESCRIPTION OF THE INVENTION

Figure 1:
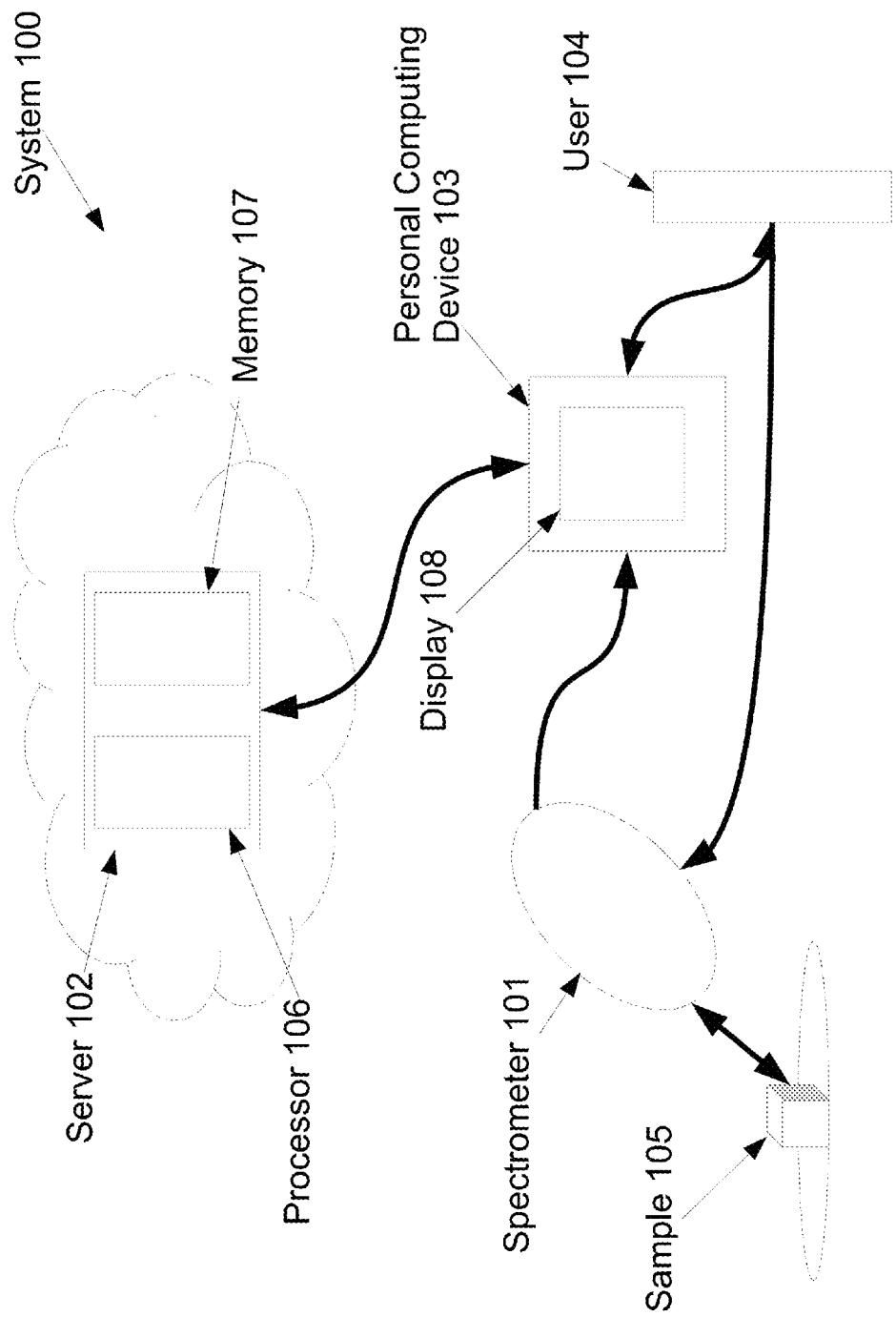
FIG. 1 depicts a block diagram of a system for identifying and analyzing a sample and displaying personalized information related to that sample.

In the description herein, various embodiments of the invention are described, including process steps, data structures, and user interfaces. Those skilled in the art will realize, after perusal of this application, that embodiments of the invention might be implemented using a variety of techniques and/or other techniques not specifically described, without undue experimentation or further invention, and that such techniques and/or other techniques would be within the scope and spirit of the invention.

Those of ordinary skill in the art will recognize, after perusal of this application, that alternative embodiments given herein are illustrative and in no way limiting, and that many variations are workable which remain within the concept, scope, and spirit of the invention.

Those of ordinary skill in the art will recognize, after perusal of this application, that the invention can be embodied in: a physical entity such as a product, apparatus, device, machine, or system; an activity such as a method, process or use; a computer-readable medium and instructions; a computer program for instructing a computer to perform a method; means or steps for performing a function; or a method of doing business.

The elements and devices of the system and its subsystems, including auxiliary elements or devices, not necessarily specifically mentioned, might operate in combination or conjunction, under control of a variety of elements or devices, to perform the steps set out in this disclosure. Those skilled in the art will recognize, after perusal of this application, that such combinations are within the scope and spirit of the invention, and would be workable without undue experimentation or further invention.

Those of ordinary skill in the art will recognize, after perusal of this application, that each of the elements in the devices, systems, subsystems, databases, and modules described herein, whether or not depicted in figures, might be implemented in one of a variety of possible ways. The elements of the devices, systems, subsystems, databases, and modules described herein, whether or not depicted in figures, are those of, and for, some embodiments, except where specifically stated otherwise. No element or description thereof is necessary for all embodiments, unless this is specifically stated.

All examples provided in the description are not intended to be limiting in any way. They are illustrations of specific aspects, features, or applications of a possible embodiment, and are provided for better understanding of the utility of the invention. Whenever the word "example" or "examples" occurs below, the phrases "in some embodiments" and "not intended to be limiting in any way" should be interpolated.

Some of the methods and processes described herein performed by the devices, systems, subsystems, and modules are described serially. However, in all such cases, the flow points and steps of these methods and processes may all be performed independently and in parallel, or by separate elements in conjunction or in parallel, whether asynchronously or synchronously, in a pipelined manner, or otherwise, except where it is necessary that such flow points and steps be performed serially, or where such necessity is explicitly so stated. There is no particular requirement that any method or process must be performed in the same order in which the description lists flow points or steps, except where necessary or where explicitly so stated. Whenever the word "method" or "process" or "step" occurs below, this paragraph should be interpolated.

The descriptions herein of the flow points and steps of process flows, whether or not depicted in figures, are for some embodiments, except where specifically stated otherwise. Nothing in any description of a step is necessary for all embodiments, unless this is specifically stated.

Some of the databases in the description may be described as if they are the sole source of the information that they contain. However in the context of the invention, there is no particular requirement that any database herein is the sole source of the information it contains or the sole source of information about the things about which it contains information or the sole source of information of whatever kind to be used by the subsystem or subsystems to which it provides information. The invention can be used in combination or conjunction with a variety of techniques for storing information, such as, for example, a plurality of databases, a hierarchical representation of data, a hyperlinked representation of data, a dynamically generated representation of data, and/or combinations or mixtures thereof.

Furthermore, while some of the databases in the description and the figures are described as if they are in the same location as each other or as, for example, the processor executing the program which is reading from or writing to the database, in the context of the invention, there is no particular requirement where any database is specifically located. For example, the databases might be located (a) at one or more remote devices available to the processor using a communication device, or (b) on a computer-readable medium coupled to a reader thereof, available to the processor or to any other element of the system.

Some of the aspects of the invention described herein are not specific to the use of a spectrometer 101 or to the data received by the server 102 being an electromagnetic spectrum. Those aspects may use alternate means of sensing a sample, such as for example a food, substance or environment. Examples of such alternate means include reading an RFID tag associated with the sample, or reading a bar code associated with the sample, or means that use techniques from, for example, gas chromatography or GC-mass spectrometry (GCMS), or means that use devices such as chemical sensors, electronic nose sensors, biosensors, bio-mimetic systems, photometric sensors, or micromechanical devices. Such alternate means include any method or means of obtaining data or information from a sample of a material, substance or environment, that is responsive to some characteristics or intensive or extensive properties of that material, substance or environment.

Some of the presentation of information to the user, may be described herein as if presented in primarily a static manner in the form of text. However, in the context of the invention, information may be presented in a dynamic manner, and/or through the use of other techniques for presenting or representing information. For example, the invention could be combined with a hierarchical presentation of data, a hyperlinked presentation of data, a dynamically generated presentation of data, or some combination or mixture thereof. In the context of the invention, information may be presented through any of text, images, audio or video or other means, or any combination of these. For example, the invention could be combined with a presentation of information in the form of a text message, a webpage, a voice message, an animated video, another kind of video, and so forth.

Some of the commands or requests from the user, as the user interacts with the system, or information or feedback entered by the user, may be described herein as if entered on a keyboard. However, in the context of the invention, the system or its subsystems can receive commands or requests from the user, or information or feedback entered by the user through any means available in combination or conjunction with computing devices such as, for example PCs, smart phones, smart watches, tablets, and/or their accessories and/or peripherals. For example, such means includes pointing devices (for example, mice, touchpads, joysticks etc.), imaging and video input devices (for example, eye gaze trackers, gesture input devices), and audio input devices (for example, microphones); and the system or its subsystems can receive commands or requests from the user, or information or feedback entered by the user through the user's voice, gestures, or eye movements.

The invention does not apply only to food, and data or digital information that is responsive to characteristics or properties of food. The invention also applies to cosmetics or household products or, more generally, substances (whether gas, liquid or solid), or environments of any kind, and to data or digital information that is responsive to characteristics or properties of, or related to, such substances or environments. Thus, in the descriptions herein, there is no particular requirement that the systems, subsystems, devices, modules, processes, databases, and user interface be limited to food, or data or digital information that is responsive to characteristics or properties of food. The systems, subsystems, devices, modules, processes, databases, and user interface also apply to cosmetics or household products or, more generally, substances (whether gas, liquid or solid), or environments of any kind, and to data or digital information that is responsive to characteristics or properties of, or related to, such substances or environments.

Lexicography

The general meaning of each of the following terms is intended to be illustrative and in no way limiting. The scope and spirit of the invention is not limited to any of these definitions, or to specific examples mentioned therein, but is intended to include the most general concepts embodied by these and other terms.

As used herein, a "spectrum" (plural, "spectra") refers to a scan that can be arranged as an array or sequence or matrix of numbers or numerical values. One example of a spectrum is information describing electromagnetic radiation with reference to its constituent wavelengths or frequencies, where such information can be arranged as an array of numbers, in which each number represents the magnitude or photon count of that electromagnetic radiation at particular wavelengths or frequencies. Such spectra include, without limitation, emission, reflection, diffusion, and transmission spectra, in the sense that those terms are used by those with skill in the art of spectroscopy, and include, without limitation, Raman, fluorescence, and laser-induced breakdown spectra (the Raman spectra include those enhanced via the Resonant Raman Effect and/or Surface Enhanced Raman Effect). Examples of spectra include three or four dimensional matrices where all but one dimension are spatial dimensions, and one dimension is responsive to magnitude of electromagnetic radiation at particular wavelengths or frequencies. In such examples, the said one dimension can have three values in the case of RGB or tristimulus color space, four values in the case of CMYK color space, or more values in case of traditional emission, reflection, diffusion, and transmission spectra. Sometimes a spectrum is referred to herein as a scan, for example, without limitation, when referring to the period of time over which the spectrum was obtained. Without intending to be limiting in any way, the systems, subsystems, devices, modules, processes, databases, and user interfaces related to the orthogonalizer program, database of spectra, spectrum analysis subsystem, ranking subsystem, link detection subsystem, user profile database, and publishing subsystem can largely be applied to, and used with, spectra defined as scans that can be arranged as arrays or sequences or matrices of numbers or numerical values, which are not necessarily information related to electromagnetic radiation, and such application and use is workable without undue experimentation by one skilled in the art and is within the scope and spirit of the invention.

As used herein, a "scan" refers to data or information related to a sample of a material, substance (whether gas, liquid, or solid) or environment, that is responsive to some characteristics or intensive or extensive properties of that material, substance or environment. For example, scans include data or information obtained through any means of sensing a sample of a material, substance or environment, where such means include reading an RFID tag associated with the sample, or reading a bar code associated with the sample, or means that use techniques from, for example, gas chromatography or GC-mass spectrometry (GCMS), or means that use devices such as chemical sensors, electronic nose sensors, biosensors, bio-mimetic systems, photometric sensors, or micromechanical devices.

As used herein, a "public food" is any food defined to be "public", and a "public food ID" is the food ID of any public food. In some embodiments, such definitions are recorded in the food database. For example, with reference to FIG. 20, a food ID X is "public" if there is a row of the food database 2000, the (column 1) food ID field of which is set to X, and the public field of which is set to yes; and a food is "public" if its food ID is a public food ID. The phrases "public subfood", "public subfood ID" etc. have analogous meanings.

As used herein to refer to foods, "similar" need not closely resemble the use in natural English. The notion of "similar" foods can be implemented in software through "parent IDs" and "subfood IDs". For example, a particular brand of corn bread might have a parent ID which refers to the generic food called "bread" and might fail to have a subfood ID which refers to "wheat flour". So in this case, a food may be called similar to that particular brand of corn bread if it also has a parent ID for "bread" and fails to have a subfood ID for "wheat flour". Generally, a criterion for similarity can be set out by specifying any set of food IDs and defining two foods A and B to be similar in a sense if, for each C of the food IDs in the set, both A and B have C as a parent ID or subfood ID, or neither A nor B do.

As used herein to refer to users, "similar" need not closely resemble the use in natural English. Instead, the notion of "similar" users could be implemented in software through the user profile database. For example, two users could be called similar if they have similar user-entered feedback, passive personal log data, personal information, user interaction data (for example, belong to the same groups), or food consumption, or any combination of conjunction of these.

As used herein, the term "food" encompasses natural foods, packaged foods, prepared dishes, and ingredients of, or additives, in the preceding, and chemicals or combinations of chemicals within the preceding. Food includes, without limitation, dairy, fish, poultry, meat, grains, nuts, seeds, legumes, herbs, spices, vegetables and fruits, and products derived from any of these. Food includes, without limitation, restaurant offerings (both menu listings and specific instances thereof), and homemade preparations. Foods include, without limitation, medications, pharmaceuticals, prescription drugs, non-prescription drugs or health food supplements. A food can be a particular sample of a food, or a stock keeping unit of a food product, or a general category of foods like "vegetables". Thus the usage of the term "food" herein extends beyond common English usage in two ways: first, in the use of a broad range from extreme specificity to extreme generality; and second, with a broad range from specific chemical compounds that may be found in food to classes of chemicals like "proteins" or "vitamins" to combinations of classes of chemicals that may be found in food like "the contents of meat if all sodium was removed" or "the protein contents of bread if all gluten was removed", even though such combinations might not be found in nature. This usage is much broader than the one used in general language, but simplifies and aids the description herein.

As used herein, the term "ingredient" (of a food) includes: ingredients listed on the label such as additives like flavours, flavour enhancers, sweeteners, food colourings, acids, emulsifiers, stabilizers, thickeners, nitrites, and preservatives; and other ingredients such as processed sugars, starches, proteins, or oils, like HFCS, maltodextrin, hydrolyzed proteins, or hydrogenated oils; and nutrients listed on the label such as vitamins, minerals, and the amount or type of fats, proteins, carbohydrates, sugars, salts, or antioxidants; and allergens, pesticides (even for organic food), metals, carcinogens, other toxins, phytonutrients, prebiotics, probiotics, and adulterants. An ingredient can be any defined subset of a particular sample of a food, or of a stock keeping unit of a food product, or of a general category of foods. Thus the usage of ingredients extends beyond common English usage in two ways: first, in the use of a broad range from extreme specificity to extreme generality; and second, with a broad range from specific chemical compounds that may be found in food to classes of chemicals like "preservatives" or "vitamins" to combinations of classes of chemicals that may be found in food like "the vitamin content other than vitamin C" or "the protein content, excepting gluten", even though such combinations might not be found in nature. This usage is much broader than the one used in general language, but simplifies and aids the description herein.

As used herein, the term "database" is used generically and is meant to encompass any organized collection of data, and its supporting data structures, including, without limitation, the data structures found in relational, hierarchical, network, entity-relationship, object, document, file-based and other database management systems or database models.

System Elements

FIG. 1 depicts a block diagram of a system for identifying and analyzing a sample and displaying personalized information related to that sample.

The system 100 depicted in FIG. 1 includes a spectrometer 101, a personal computing device 103, and a server 102. Some embodiments include multiple spectrometers 101, obtaining data from multiple samples 105, and multiple personal computing devices 103, interacting with multiple users 104, and possibly multiple servers 102.

For example, the personal computing device 103 might include one or more of the following devices, possibly operating in combination or conjunction: (a) a handheld or wearable computing device, such as a smart phone, smart watch, or tablet, capable of generalized computation and presentation of information; (b) a PC (personal computer), laptop, or other device suitable for generalized computation and presentation of information; or (c) any other type of computing device suitable for generalized computation and presentation of information. In the context of the invention, there is no particular requirement that personal computing devices 103 be limited to personal use by a human individual. For example, the personal computing device could be used by any one or more users, such as for example individuals, robots, companies, families, or other groups or entities.

For example, the spectrometer 101 might include one or more of the following devices, possibly operating in combination or conjunction: (a) a Raman spectrometer containing a light source, lens, grating and detector; (b) another kind of spectrometer such as an infrared absorption spectrometer, a mass spectrometer, or an atomic absorption spectrometer; (c) another kind of device containing a detector sensitive to the wavelength composition of the electromagnetic radiation transmitted through, reflected by, or radiated by, an object, that object possibly receiving other electromagnetic radiation from the environment or from a light source in the device.

For example, the server 102 might include one or more of the following devices, possibly operating in combination or conjunction: (a) a server, which is a device suitable for generalized computation and storage of information, and which is connected to the internet, and which can be remote from the spectrometer 101 and the personal computing device 103; (b) a virtual server, which acts like a server, but shares its memory, storage, and/or central processing units with other virtual devices, possibly unrelated in function; or (c) any other type of device or combination of devices suitable for generalized computation and storage of information.

Those skilled in the art will recognize, after perusal of this application, that embodiments involving other auxiliary presentation, display, input, output, and computation devices, operating in combination or conjunction are within the scope and spirit of the invention, and would be workable without undue experimentation or further invention. For example, some embodiments might include PCs, laptops, smart phones, tablets, smart watches, or other computing devices, operating in combination or conjunction with each other and with accessories and/or peripherals such as keyboards, pointing devices (for example, mice, touchpads, joysticks etc.), imaging and video input devices (for example, eye gaze trackers, gesture input devices), audio input devices (for example, microphones), display devices, audio output devices (for example (output of sounds or speech), tactile output devices, and/or printers.

In some embodiments, the server 102 contains, or is coupled to at least one communication element, capable of sending and receiving information from a logically remote device, such as for example a computer network coupled to an internet, intranet, LAN, WAN, VPN, or enterprise network. In some embodiments, the personal computing device 103 contains, or is coupled to at least one communication element, capable of sending and receiving information from a logically remote device, such as for example a computer network coupled to an internet, intranet, LAN, WAN, VPN, or enterprise network. In some embodiments, other devices or submodules or subsystems or input or output elements contain, or are coupled to, at least one communication element, capable of sending and receiving information from a logically remote device, such as for example a computer network coupled to an internet, intranet, local network, LAN, WAN, VPN, or enterprise network.

The personal computing device 103 can receive requests from a user 104 of the system 100 and respond to those requests by providing information related to use of the system 100 through the display 108. For example, such information might include: (a) information responsive, at least in part, to the data related to one or more samples 105 which has been obtained by the spectrometer 101; (b) information about those samples, which is responsive, at least in part, to calculations or computations by the server 102; and/or (c) other information, related to those samples or to the use of the system 100. In some embodiments, some elements, devices, submodules, and/or subsystems are responsive to inputs from other elements, devices, submodules, and/or subsystems and respond to those inputs.

The system 100, using the input elements of personal computing device 103, or input elements coupled to, or used in combination with, personal computing device 103, and/or other input elements coupled to, or used in combination with, other devices, elements, subsystems, or submodules, can receive information from the user 104. The user 104 can be, for example, an individual who desires particular or personalized information about sample 105, or about one or more previous samples, individually or collectively. The system 100, using the at least one display element 108 of personal computing device 103, or display elements coupled to, or used in combination with, personal computing device 103, can present information to the user 104.

In the context of the invention, there is no particular requirement that the user 104 is limited to an human individual. The user 104 might include an individual, a robot, a company, a family, or another group or entity. In some embodiments, where the user 104 includes a company or family or another group, the user 104 might include more than one person who interacts with the system 100 from time to time.

Moreover, in the context of the invention, there is no particular requirement that: the same kind of information is received from each input element of the personal computing device 103, or each input element coupled to, or used in combination with, any other device, element, subsystem, or submodule; or that the same kind of information is presented at each output element of the personal computing device 103 or each output element coupled to, or used in combination with, any other device, element, subsystem, or submodule. In some embodiments, the one or more input elements and the one or more output elements of the personal computing device 103 are coupled to the processor 106 and the memory or mass storage 107 using a local network, such as for example a LAN, VPN, or enterprise network.

In some embodiments, the server 102, under control of the processor 106 and using memory or mass storage 107, can: (a) process some or all of the data obtained by one or more spectrometers 101 (for example, the spectra of samples), the data originally obtained by one or more passive log devices 303 of FIG. 3, other data or information obtained through one or more personal computing devices 103 or other devices, such as user feedback or user interaction data, including explicit or implicit commands or requests from the user 104, and/or other data or information; (b) parse, recognize, process, and/or store those data, spectra, commands, requests, or information; (c) determine zero, one, or more responses to make to those data, spectra, commands, requests, or information; and (d) direct one or more output elements of one or more personal computing devices 103 to present those such responses to one or more users 104.

Figure 2:
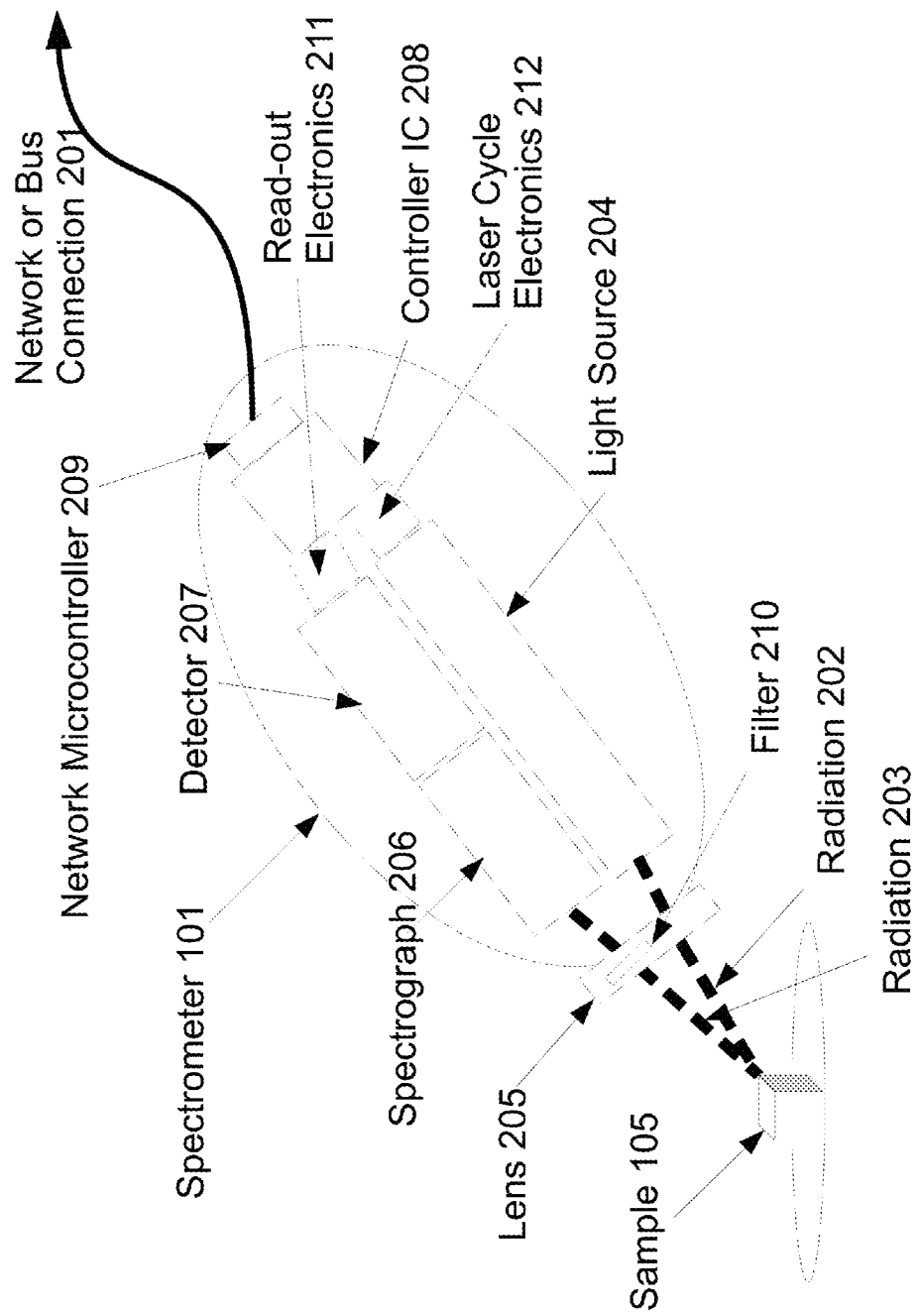
FIG. 2 depicts a block diagram of a spectrometer 101 including a means of obtaining a Raman spectrum of a sample 105 and transmitting it for analysis.

FIG. 2 depicts a block diagram of a spectrometer 101 including a means of obtaining a Raman spectrum of a sample 105 and transmitting it for analysis.

(a) the spectrometer 101 includes a light source 204, for example, a laser, or spectrum-narrowed LED, which emits electromagnetic radiation 202 at the sample 105 through a lens or substantially transparent aperture 205; (b) the spectrometer 101 also includes a grating 206, or other spectrograph, capable of separating the incoming electromagnetic radiation 203 into a frequency spectrum; and (c) the electromagnetic radiation 203 has been emitted by the sample 105 at least partly in response to its absorption of some of the energy of the electromagnetic radiation 202. In some alternate embodiments, the electromagnetic radiation 203 can instead be a part of the electromagnetic radiation 202 that has not been absorbed by the sample 105. In some embodiments, the spectrograph 206 could be a prism or linear variable filter.

The spectrometer 101 includes a detector 207, which is capable of producing an electrical or electronic signal, in response to incoming electromagnetic radiation, which, under the control of controller integrated circuit 208, can be digitized and transmitted in packets over the network or bus connection 201 by network microcontroller 209. In other embodiments, the detector could be any one or more wavelength selective elements, such as a complementary metal oxide semiconductor (CMOS) or charge coupled device (CCD) image sensor.

In some embodiments, the detector is sensitive to 256 frequencies or narrow frequency bands, corresponding to the approximate Raman offsets −1515 to −535, which is understood by those with ordinary skill in the art. The actual measurement band can be calculated by those with ordinary skill in art from those Raman offsets and the wavelength of the laser. In the example of a 785 nm laser, the measurement band could extend from 825 nm to 895 nm. In some embodiments, the number of frequencies or narrow frequency bands could be 512 or 128 or some other number. In other embodiments, the frequencies or narrow frequency bands could correspond to a different range of Raman offsets, or to a selection of non-evenly spaced Raman offsets, chosen to obtain adequate data at a reduced cost. In the example of a non-evenly spaced selection of frequencies, the frequencies can be chosen carefully, and in some embodiments, the detector can be sensitive to as few as 50 frequencies or narrow frequency bands. In the context of the invention, there is no requirement that the laser be near-infrared; the laser could be far-infrared or mid-infrared or visible light or ultraviolet or in another part of the electromagnetic spectrum.

In some embodiments, the detector is 16-bit. In other embodiments, the detector can be 12-bit, 8-bit, or even single-bit, and this choice might depend on the available read-out rate. In some embodiments, the light source can cycle between on and off, and the system can obtain spectra of the sample while it is stimulated by the light source, and spectra of the sample while it is not so stimulated. Accordingly, in those embodiments, the read-out of the detector can be synchronized with the cycle of the light source, and the minimum bit count for the detector depends in part on the light throughput and the rate at which the light source cycles. For example, the detector could be 12 bit at 2 Hz, or 8 bit at 24 Hz. In some embodiments, the detector might read-out out-of-sync with the light source, but, in those cases, the read-out rate may be at least several times larger than the cycle rate of the light source, say at least 6 times. In those conditions, methods familiar to those skilled in the art can be used to recover a sufficient number of readouts that are as if synchronized. For example, if the read-out rate is at least 6 times the cycle rate of the light source, then four out of six readings at least will be as if in sync, and methods familiar to those skilled in the art can be used to design software that can detect these and discard the others.

In some embodiments, (a) the spectrograph 206 is a high resolution spectrometer constructed using techniques of nanophotonics with a wide spectral range and a small footprint (e.g. 5 mm squared), and made from versatile materials compatible with CMOS assembly; and (b) the spectrograph 206 contains an optical resonant cavity and a wavelength demultiplexer. In some embodiments, polarization splitting is not performed in the spectrograph, but in other embodiments, it is performed.

In some embodiments, the light source 204 is a visible light laser at 532 nm and power approximately 5 mW. In other embodiments the laser could be approximately 5 mW at 1064 nm with a 532 nm component, or the laser could be approximately 1 mW at 785 nm. The light source 204 can be a diode laser or a diode pumped solid state (DPSS) laser that is implemented in popularly known laser pointers or another kind of laser. In some embodiments, the light source is the flash built into a camera or smart phone.

In some embodiments, (a) the lens 205 includes a filter for light with a wavelength close to that of the light source; (b) the spectrometer 101 contains a safety button so that the light source 204 emits the radiation 202 only when the button is held down by the user 104; (c) the spectrometer 101 emits radiation 202 from the light source 204, and receives radiation 203, through the lens 205, which protrudes no more than 1 cm from the body of the enclosure; (d) a bandpass filter 210 eliminates (e.g. reflects away) reflected laser light; and (e) the focal point of the laser is between 3 mm and 10 mm from the lens.

In some embodiments, (a) if wired, the spectrometer 101 obtains its power over the USB connection, and if wireless, the spectrometer 101 obtains its power from batteries; (b) the network or bus connection 201 is USB, if wired, and Bluetooth, if wireless; and (c) the spectrometer 101 has a form factor that makes it comfortable to hold, operate, and point, with one hand. For example, the spectrometer might be shaped like an ellipsoid with dimensions 8 cm by 4 cm by 1 cm.

In some embodiments, the spectrometer 101 is integrated into a handheld or wearable computing device such as a smart phone, smart watch, or into another personal computing device, like a tablet. In some such embodiments, for example in a smart phone: (a) the lens 205 for the spectrometer might be the same as, or adjacent to, the lens for the built-in camera in a smart phone, although the filter 210 might extend over part or all of the lens; (b) the laser or other light source 204 might be integrated with, or be the same as, or be adjacent to, the flash for the camera in a smart phone; (c) some or all of the spectrograph or grating 206, the detector 207, the laser-cycle electronics 212, and/or the read-out electronics 211 are integrated into the electronics of a smart phone; and/or (d) the controller IC 208, network microcontroller 209, and/or network connection 201 might be the same as those found in a standard smart phone. In some embodiments, the detector 207 is part of, integrated with, or adjacent to, the built-in camera in a smart phone.

In other embodiments, the spectrograph comprises a tunable filter, such as a liquid crystal (LC) tunable filter, an acousto-optic tunable filter, or a rotating color wheel. In some such embodiments, wavelength tuning or selection is performed by varying the voltage applied to the liquid crystal or by rotating the color wheel.

In some embodiments, the light source 204 on the one hand, and the filter 210, spectrograph 206, and detector 207 are positioned on opposite sides of the sample 105, in order to measure the absorption spectrum of the sample 105. In some such embodiments, and in other embodiments, the sample 105 is placed in a transparent sample holder, such as a cuvette. In some such embodiments, the light source 204 is broadband such as an LED, and, for example, the absorption spectrum of room air, or outdoor air, or the gases exhaled, or released by, the user or another person, is obtained.

In some embodiments, the spectrometer 101 is integrated with a camera capable of taking a two- or three-dimensional photograph or video of the sample, and in some of those embodiments the photograph or video might be taken automatically at substantially the same time as the scan is obtained. In some such embodiments, the photograph or video is transmitted to, and received by, the server 102 following steps similar to those depicted in FIG. 5. In some embodiments, after the photograph or video is received by the server, it (or a reference to it) is indexed by the database of spectra 2200, and the photograph or video could be used, for example, to estimate the volume of the sample, as discussed herein. For another example, the photograph or video could be used to estimate the homogeneity of the sample, and, if the system determines that the sample is not homogeneous, then: (a) the user could be prompted to perform another scan; (b) the user could be prompted to perform the scan while moving the spectrometer relative to the food, or the food relative to the spectrometer; (c) a signal triggering an audible sound indicating that the scan is complete might be delayed until the system determines that data has been received for all parts of the sample; and/or (d) generalizations or the like. For another example, a video could be used to estimate the movement of the spectrometer relative to the food or the food relative to the spectrometer, and then the variation over time of the scan could be used to estimate the homogeneity of the sample, and the reliability of, or confidence in, the identification of the samples performed by the system 100 and/or the timing of a signal triggering an audible sound indicating that the scan is complete. In some embodiments, a photograph or video of the food could be analyzed by a person or an image recognition software, and the identification provided by the system could be compared with the identification provided by the person or image recognition software, and the result of such comparison could be used to verify, or support, or estimate, the reliability of, or confidence in, the identification of the sample by the system. In another example, the photograph or video could be used to estimate the ambient light on the sample and/or the placement of the spectrometer relative to the sample, and the change in, and/or variability of, this ambient light or this placement during the period of time that the scan is obtained, and these estimates could be compared with, or correlated with, or related to, the data related to the spectrum obtained by the spectrometer and/or the ambient light gathered by, computed by, or deduced by, the decolorizer 702, and, in response to this comparison, correlation, or relation, the system could prompt the user to keep the spectrometer at a more fixed angle or position, or a closer or farther position, or to shield the sample from the ambient light in some way. In another example, the photograph or video could be used as a media object presented to another user in combination or conjunction with the recommendation or discussion of a food or meal or in the sharing of a user's eating experiences with their friends, or as a media object presented to the same user reviewing their past food intake or past eating experiences, and the like. In some embodiments, the spectrometer 101 is integrated with, or used in conjunction with, a device other than a camera that can be used to estimate the volume of a sample.

In some embodiments, the spectrometer 101 and/or personal computing device 103 also contains a beeper, buzzer or other component capable of emitting an audible sound. For example, this sound could be similar to that heard when scanning a badge or key card when entering a workplace. For example, this audible sound could be emitted after the user presses the button on the spectrometer 101 and keeps it pressed down continuously for 5 seconds. In another example: (a) the spectrometer 101 can upload a scan to the server 102 every 1 second; (b) the server 102 can process the uploaded spectra and evaluate whether or not the server has received enough data to confidently identify all parts of the sample; (c) the server 102 can, after determining that enough data has been received, send a signal to the spectrometer 101, through the personal computing device 103, or to the personal computing device 103, indicating that enough spectra have been received; and (d) the spectrometer and/or the personal computing device can, on receiving this signal, emit an audible sound. In some embodiments, the light source 204 illuminates only a small portion of the sample, and the user can be instructed to move the spectrometer when scanning so that a scan of all parts of the sample is obtained. In conjunction with the embodiments described below for the spectrum processing subsystem 403, some such embodiments could provide a user experience in which the user need not carefully scan each food on their plate, for example, individually, but instead, for example, the user can just scan their plate, moving the spectrometer around, back and forth or in circles, until they hear a beep, and then they're done.

Figure 3:
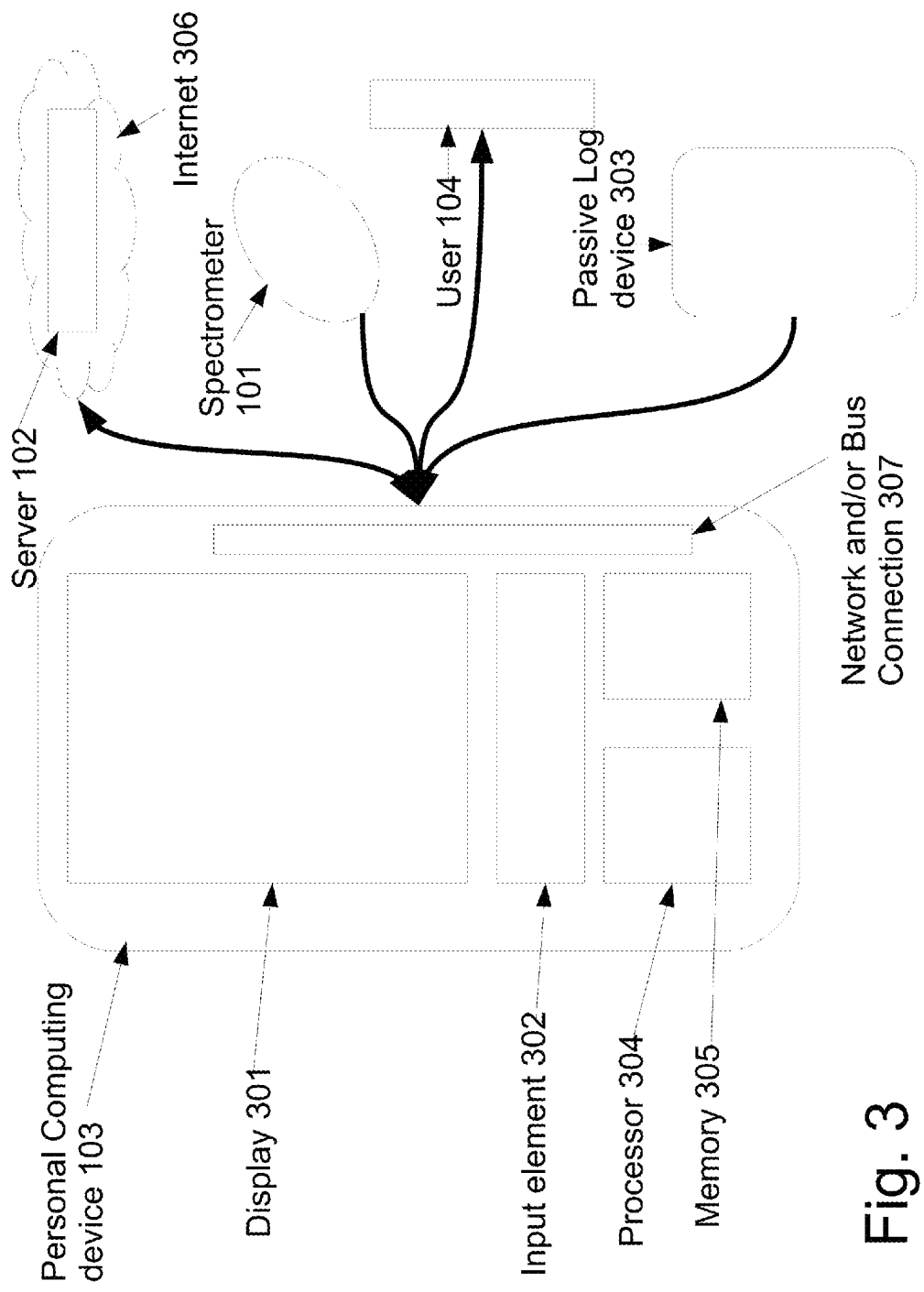
FIG. 3 shows a block diagram of a personal computing device including a means for receiving and transmitting spectra of samples and other data to a server, and a display for showing personalized information about samples and other information.

FIG. 3 shows a block diagram of a personal computing device including a means for receiving and transmitting spectra of samples and other data to a server, and a display for showing personalized information about samples and other information.

Personal Computing Device

FIG. 3 depicts a block diagram of a personal computing device 103, including a display 301, an input element 302, memory 305, a central processor 304, and a network and/or bus connection 307. The personal computing device 103 is attached to the spectrometer 101 by either a wired, such as USB, or wireless, such as Bluetooth, connection. In some embodiments, the personal computing device 103 is attached to a passive log device 303, such as a personal health monitor.

Those skilled in the art will recognize that the input element 302 and the display screen 301 operate in combination or conjunction, under control of the processor 304 and the memory or mass storage 305, to present a user interface, or UI, possible examples of which are described herein.

Examples of the UI are depicted in FIG. 24, FIG. 25, FIG. 26, and FIG. 27. The UI includes at least some elements to be presented on the display screen 301, including possibly a set of screen regions. These screen regions include information elements, such as 2404 in FIG. 24, branding elements, such as 2401 in FIG. 24, and graphical input elements such as 2702 in FIG. 27. In some embodiments, screen regions may sometimes be disjoint and/or sometimes overlapping and elements to be presented on the display screen may include one or more scroll affordances or scroll bars (possibly horizontal or possibly vertical), one or more highlighting features or pointing elements, one or more iconic or symbolic elements, one or more pictures (possibly still pictures, animation, or motion video), and/or one or more units of text (possibly presented in one or more fonts), and the like. The description of the UI herein as consisting of two dimensional, relatively static presentations on a display screen is in no way limiting, and a UI in which some or all presentations are audio/video are workable without undue experimentation.

The UI also includes at least some elements to be used to receive input from the user 104, such as the graphical input element 2702 depicted in FIG. 27. In alternate embodiments, these elements presented on the display 301 include a set of buttons, possibly pre-selected and fixed in function, or possibly selected in response to user preferences or other input and alterable in function from time to time.

As described herein, references to the UI or the personal computing device "receiving" input or "presenting" output describe operations by the processor 304 and the program and data memory or mass storage 305, as described above, to (a) receive explicit or implicit commands or requests from the user 104 and/or other data or information, (b) parse, recognize, process, and/or store these commands, requests, and/or other data or information, (c) determine zero, one, or more responses to make to those commands, requests, and/or other data or information, and (d) direct the display 301 and/or one or more other output elements to present those responses to the user 104. FIG. 3 depicts the personal computing device as receiving input from the server 102 through the interne 306, from the spectrometer 101, from the user 104, and from the passive log device 303. FIG. 3 also depicts the personal computing device as presenting output to user 104.

Figure 4:
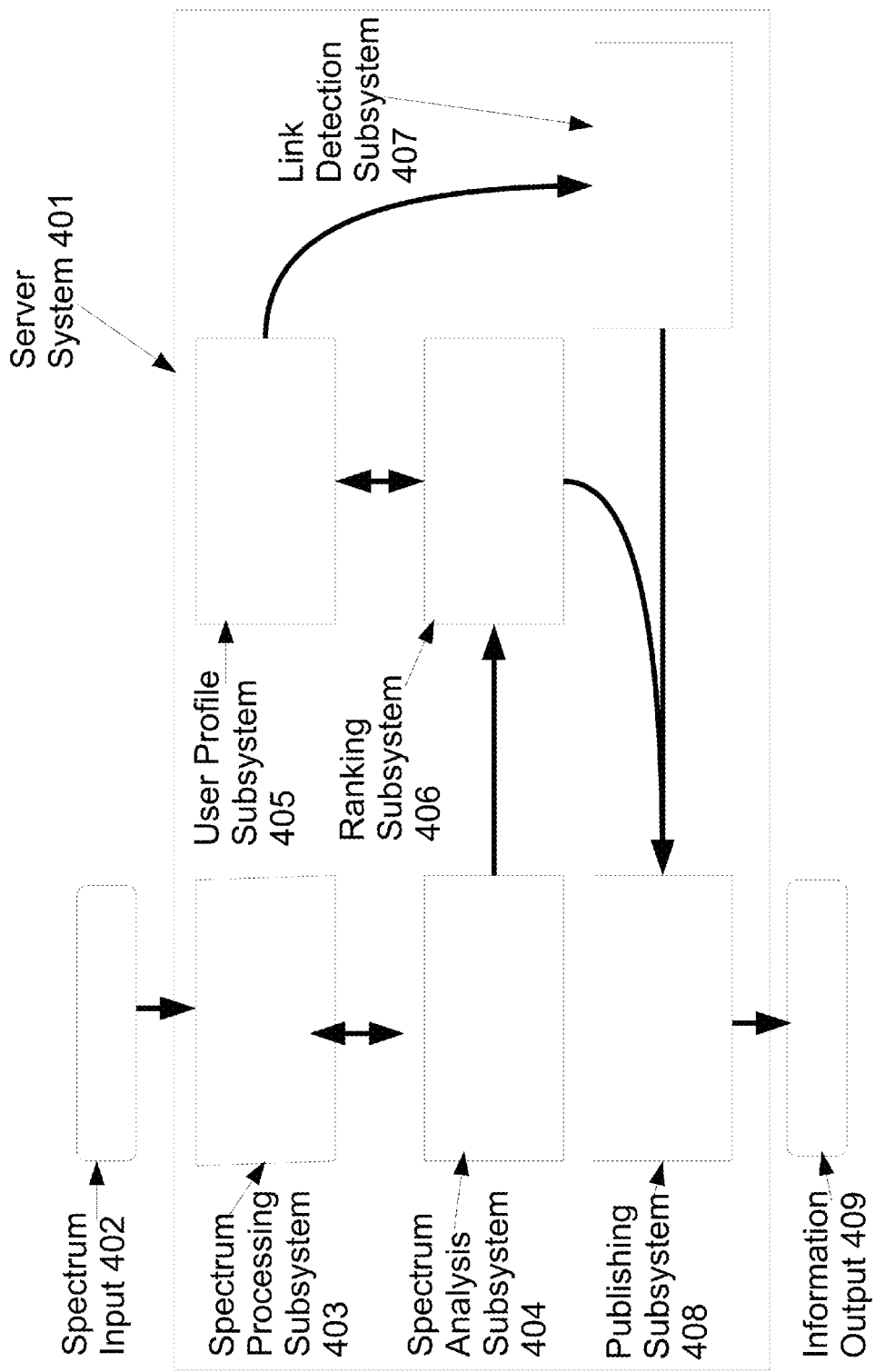
FIG. 4 shows a block diagram of a server system including a means for processing and analyzing spectra of samples and other data and a means for publishing personalized information about samples.

FIG. 4 shows a block diagram of a server system including a means for processing and analyzing spectra of samples and other data and a means for publishing personalized information about samples.

The server system 401 depicted in FIG. 4 includes a spectrum processing subsystem 403, a spectrum analysis subsystem 404, a publishing subsystem 408, a user profile subsystem 405, a ranking subsystem 406, and a link detection subsystem 407. In some embodiments: (a) the server system 401 is connected to a network, and through that connection the server system 401 can receive an input spectrum 402 and can output information 409 to be displayed on a personal computing device 103; (b) an input spectrum 402 received by the server system 401 is input to the spectrum processing subsystem 403; (c) the output of the spectrum processing system 403 is input to the spectrum analysis subsystem 404; and (d) the output of the spectrum analysis subsystem 404 is input to the ranking subsystem 406. In some embodiments: (a) the ranking subsystem 406 can query the spectrum analysis subsystem 404; (b) the spectrum analysis subsystem 404 can query the spectrum processing subsystem 403; (c) the ranking subsystem 406 can query the user profile subsystem 405; (d) the link detection subsystem 407 can query the user profile subsystem and output to the publishing subsystem 408; (e) the ranking subsystem 406 can output to the publishing subsystem 408; and (f) the output information 409 is output by the publishing subsystem 408.

In some embodiments, the server 102, and its software, the server system 401, and the subsystems 403, 404, 405, 406, 407, and 408 are, and can be, updated, improved, changed, replaced, moved, distributed, and/or extended without the need for any changes to the spectrometer 101 or the personal computing device 103. In some embodiments, additionally, the personal computing device 103 and its software is, and can be, updated, improved, changed, extended, and/or replaced, without the need for any changes to the spectrometer 101. In some embodiments, the system 100 contains many spectrometers 101, of various models, dates, and capabilities, and many personal computing devices 103, of various models, dates, and capabilities.

Figure 5:
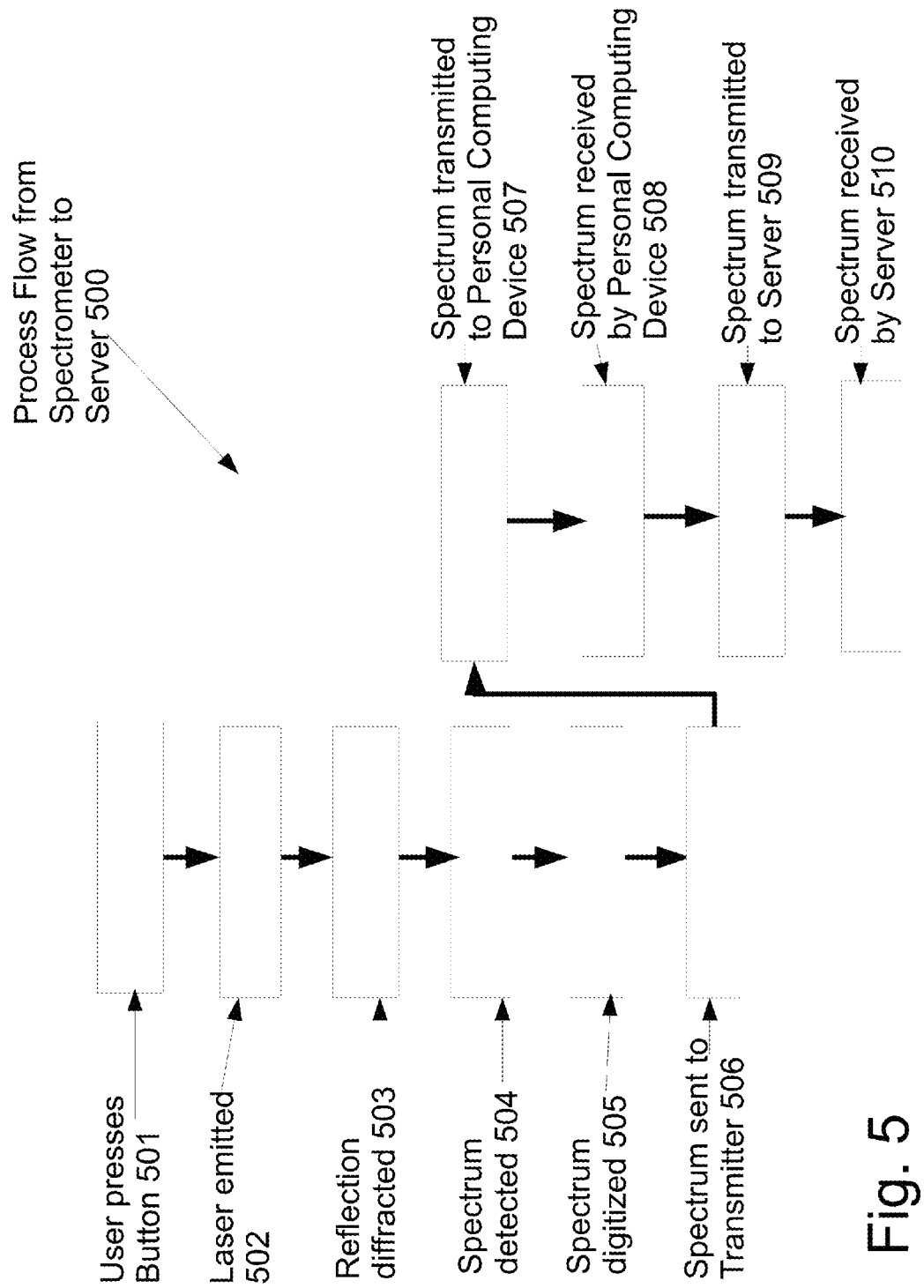
FIG. 5 depicts the process flow 500 of a method of operation of a spectrometer 101 and transmission of spectra of samples obtained by the spectrometer to a server system 401 through a personal computing device 103, as portrayed in the block diagrams FIG. 1, FIG. 2, and FIG. 3.

FIG. 5 depicts the process flow 500 of a method of operation of a spectrometer 101 and transmission of spectra of samples obtained by the spectrometer to a server system 401 through a personal computing device 103, as portrayed in the block diagrams FIG. 1, FIG. 2, and FIG. 3.

FIG. 5 depicts a step 501, in which the user 104 provides input to the spectrometer 101, for example by pressing a button, and holding that button down until an audible or other signal, such as a beep, is emitted by the personal computing device 103 and heard or otherwise noticed by the user.

FIG. 5 depicts a step 502, in which the spectrometer 101, specifically the light source 204, emits laser radiation 202, under control of the controller IC 208, and the laser cycle electronics 212, in response to the input provided in step 501. For example, the laser radiation focuses substantially on, or in, the sample 105.

FIG. 5 depicts a step 503, in which the filter 210 in the lens 205 reflects or absorbs some of the radiation emitted by sample 105 in response to the radiation 202, and the spectrograph 206 receives some of the radiation that passes through the lens 205, where it is diffracted, and separated into a frequency spectrum, which is emitted into the detector 207.

FIG. 5 depicts a step 504, in which the detector 207 produces an electrical or electronic signal in response to the incoming frequency spectrum emitted into it at step 503, and transmits this signal to the read-out electronics 211.

FIG. 5 depicts a step 505, in which the read-out electronics 211, under the control of the controller IC 208, converts the analog signal received from the detector 207 into a digital signal suitable for packetization and transmission.

FIG. 5 depicts a step 506, in which the network microcontroller 209 transmits, or causes to be transmitted, the digital signal produced in step 505 by the read-out electronics 211, directly or indirectly, to the network microcontroller 209.

FIG. 5 depicts a step 507, in which the network microcontroller 209 prepares the digital signal received after step 506 as data suitable for transmission over a network, for example by packetization, and sends it over the network or bus connection 201, for example by Bluetooth or USB, to the personal computing device 103.

FIG. 5 depicts a step 508, in which the personal computing device 103 receives the data sent in step 507, through the network or bus connection 307.

FIG. 5 depicts a step 509, in which the personal computing device 103 transmits the data received in step 508, to the server 102 over a network, such as the internet 306, through the network or bus connection 307.

FIG. 5 depicts a step 510, in which the server 102 receives the data sent in step 509, and this data becomes, as depicted in FIG. 4, input to the server system 401 at spectrum input 402.

Figure 6:
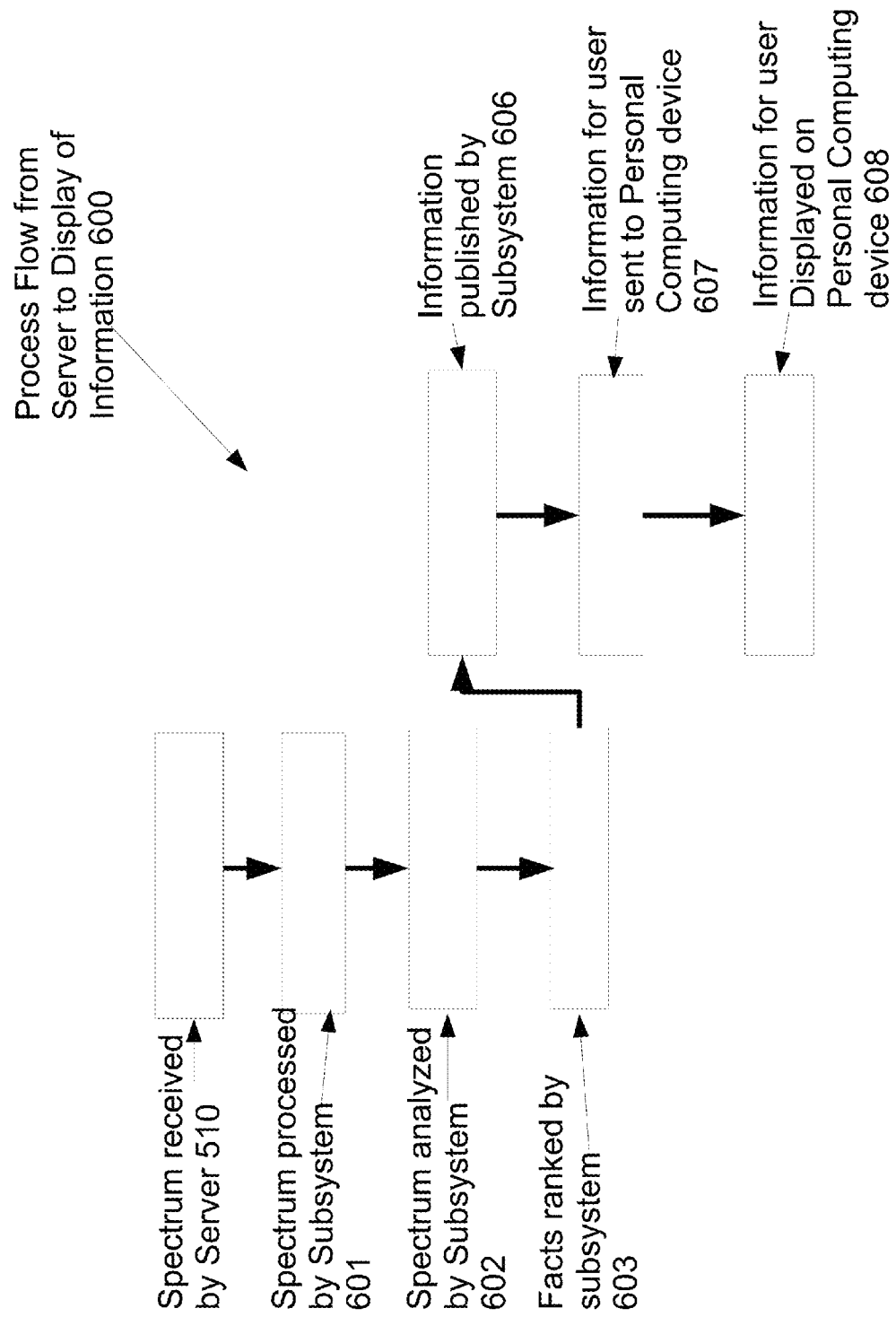
FIG. 6 depicts the process flow 600 of a method of operation of a server system 401 and transmission of data from the server system to a personal computing device 103 and display of information on the personal computing device, as portrayed in the block diagram FIG. 1, FIG. 3 and FIG. 4.

FIG. 6 depicts the process flow 600 of a method of operation of a server system 401 and transmission of data from the server system to a personal computing device 103 and display of information on the personal computing device, as portrayed in the block diagram FIG. 1, FIG. 3 and FIG. 4.

FIG. 6 depicts a step 510, at which the server 102 has received the data sent in step 509 of FIG. 5 as input to the server system 401, and sends this as input to the spectrum processing subsystem 403.

FIG. 6 depicts a step 601, at which the spectrum processing subsystem 403 of the server system 401 processes the data received after step 510 is performed, and then sends the output to the spectrum analysis subsystem 404.

FIG. 6 depicts a step 602, at which the spectrum analysis subsystem 404 of the server system 401 processes the data received after step 601 is performed, and then sends the output to the ranking subsystem 406.

FIG. 6 depicts a step 603, at which the ranking subsystem 406 of the server system 401 processes the data received after step 602 is performed, in particular by ranking facts about food, and then sends the output to the publishing subsystem 408.

FIG. 6 depicts a step 606, at which the publishing subsystem 408 of the server system 401 processes the data received after step 603 is performed, in particular preparing information suitable for display to the user 104 on the personal computing device 103.

FIG. 6 depicts a step 607, at which the server 102 transmits the information prepared by the server system 401, specifically the publishing subsystem 408, at step 606, to the personal computing device 103.

FIG. 6 depicts a step 608, at which the personal computing device 103 receives the information sent in step 607, and, under the control of the processor 304 and memory 305 displays it to the user 104 on the display 301.

Spectrum Processing

Figure 7:
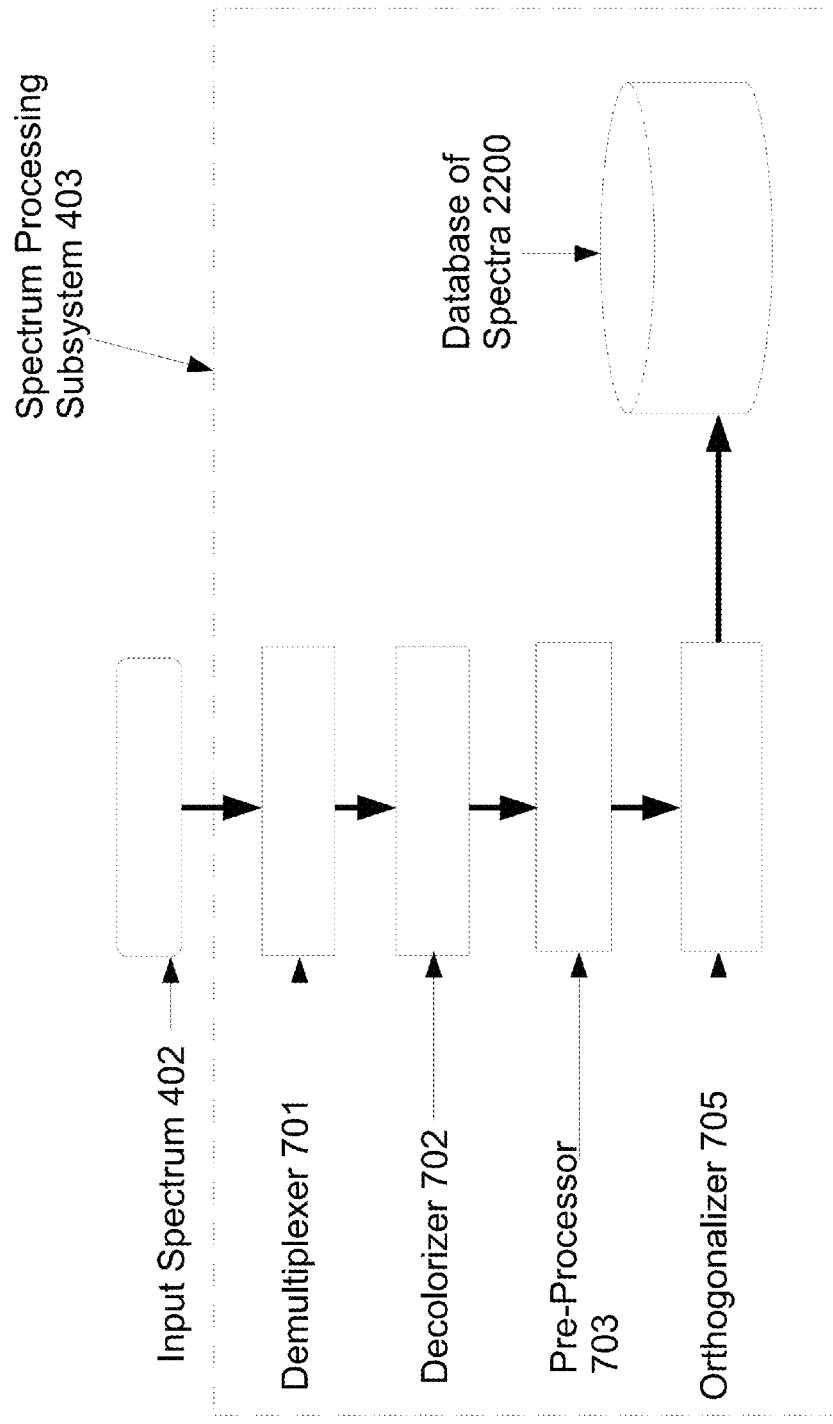
FIG. 7 shows a block diagram of the spectrum processing subsystem of a server system, including means for processing spectra into a form suitable for analysis.

FIG. 7 shows a block diagram of the spectrum processing subsystem of a server system, including means for processing spectra into a form suitable for analysis.

The spectrum processing subsystem 403 depicted in FIG. 7 includes a demultiplexer program 701, a decolorizer program 702, an orthogonalizer program 705, and a database of spectra 2200. In some embodiments, the decolorizer program 702 includes a program capable of removing or reducing fluorescence and/or the spectrum processing subsystem 403 includes a pre-processor program 703 capable of additional processing such as the smoothing of spectra and/or extraction of first and/or second differences of the spectra. In some embodiments: (a) the spectrum processing subsystem 403 is connected to a network, and through that connection is capable of receiving an input spectrum 402; (b) the spectrum processing system 403, specifically the orthogonalizer program 705 within that system, can write to the database of spectra 2200, and when it does this, can notify the spectrum analysis subsystem 404, which can then respond by initiating its own process; (c) the spectrum analysis subsystem 404 can query the database of spectra 2200 within the spectrum processing subsystem 403, and, in response, the spectrum processing subsystem 403 can output the requested data stored in the database of spectra 2200; and/or (d) an input spectrum 402 received by the spectrum processing subsystem 403 can be an input for the demultiplexer program 701, and the output of that program can be an input for the decolorizer program 702. In some embodiments, the output from the decolorizer program 702 is capable of being an input to the program 703 capable of additional processing. In some embodiments, the output from the decolorizer program 702 can be an input to the orthogonalizer 705. If the pre-processor program 703 is present, then in some embodiments, its output can be an input to the orthogonalizer program 705. In some embodiments, the orthogonalizer program 705 can write its output to the database of spectra 2200. In alternative embodiments, output from the orthogonalizer program 705 is capable of being a direct input for the spectrum analysis subsystem 404.

In some embodiments: (a) the spectrum input 402 contains one or more spectra of the sample 105 gathered through the operation of the detector 207 when the light source 204 is emitting light, and one or more spectra of the sample 105 gathered through the operation of the detector 207 when the light source 204 is not emitting light; (b) the demultiplexer 701 can output a single spectrum of the sample in response to the aforementioned spectra that were gathered when the light source was emitting light, and that single spectrum is expected to substantially measure the sum of the Raman scattering and the fluorescence in response to the light source radiation and the Rayleigh scattering and fluorescence in response to the ambient light; and (c) the demultiplexer 701 can output a single spectrum of the sample in response to the aforementioned spectra that were gathered when the light source was not emitting light, and that single spectrum is expected to substantially measure only the Rayleigh scattering and fluorescence from the ambient light.

In some embodiments, the decolorizer 702 can receive the two (single) spectra output by the demultiplexer 701 as input, and the decolorizer 702 can then subtract the single spectrum of the sample calculated in response to the spectra that were gathered when the light source was emitting light from the single spectrum of the sample calculated in response to the spectra that were gathered when the light source was not emitting light. This difference spectrum is expected to substantially measure the sum of the Raman scattering and some fluorescence.

In some embodiments, the pre-processor 703 can further process the spectrum output by the decolorizer 702 before it is input to the orthogonalizer 705. This pre-processor 703 may, for example, smooth the spectrum, or compute the first or second differences of the spectrum. In some embodiments, the pre-processor can (a) perform a (principal component analysis) PCA decomposition, thereby transforming the spectrum from one basis to another, in the sense of linear algebra; (b) transform the spectrum to some other basis, for example, a basis consisting of wavelets or using a discrete Fourier transform; and/or (c) perform several such transformations, in parallel or in series (i.e. iteration). There is no particular requirement that a transformation use an orthogonal basis, or even a basis. The transformations may use techniques from factor analysis, canonical correlation analysis, non-linear generalizations of PCA, multilinear PCA, higher-order PCA, or weighted PCA.

In some embodiments: (a) the spectrum X output by the decolorizer can be input to the orthogonalizer program 705, which maintains a list of reference spectra against which it can compute orthogonalizations; (b) the orthogonalizer program can, for each reference spectrum Y, compute the projection P of the input spectrum X onto the reference spectrum Y, and then subtract this projection P from the input spectrum X; and (c) the orthogonalizer program can write this resulting difference X−P spectrum to the database of spectra 2200. The resulting difference spectrum X−P, which we call herein an ortho spectrum, is expected to be substantially orthogonal to the reference spectrum Y, and the difference P between the spectrum X input to the orthogonalizer 705 and an ortho spectrum X−P is expected to be substantially a scalar multiple of the corresponding reference spectrum Y. In some embodiments, the number of reference spectra in the list of reference spectra maintained by the orthogonalizer program 705 is about 60. In some embodiments, the number of reference spectra could be as small as two or three, or as large as several thousand.

In some embodiments, some of the reference spectra used by the orthogonalizer 705 are obtained by means of PCA-like analysis of spectra in various states of processing. For example, a reference spectrum Y can be obtained by computing the spectrum X(F), projection onto which gives the greatest variance among multiple spectra of a food or class of foods F, and then computing the spectrum Y of length one onto which the projections of a family of X(F) are largest. For another example, a reference spectrum Z can be obtained by computing the spectrum Z, such that the projections onto Z of spectra in a class of foods C and the projections onto Z of spectra not in a class of foods C have the greatest difference. For another example, a reference spectrum Z can be obtained by computing the spectrum Z, such that dot products of spectra with Z give the closest match to a numerical characteristic of foods, possibly from a 3rd party database, such as sugar content. In some embodiments, the computations above can be iterated, combined, and modified through a variety of techniques such as averaging known to those familiar with the art.

In some embodiments, the list of reference spectra against which the orthogonalizer 705 computes orthogonalizations is maintained by periodically optimizing the choices in the list, while the number of reference spectra is fixed, perhaps at 60. In some such embodiments, the strategy optimizer 905, depicted in FIG. 9 re-generates the list of strategies at step 1007, as depicted in FIG. 10, and generates a report which records how often each orthogonalization is used in identifying spectra. Then, periodically, the least useful spectra can be dropped from the list of reference spectra, and new spectra to replace these may be added speculatively. In some embodiments, these new spectra are chosen by trial and error with the benefit of human intuition or knowledge. In alternative embodiments, other methods are used. For example, even highly useful spectra in the list of reference spectra might be speculatively replaced by similar spectra until each reference spectrum is locally optimized. In alternate embodiments, some orthogonalizations are computed against more than one reference spectrum—that is, what we call here a reference spectrum is a multi-dimensional subspace of the space of all spectra. In some embodiments, at least one reference spectrum is not a spectrum output by the decolorizer at all, but is a spectrum derived from other spectra, such as an average of other spectra or an orthogonalization of a spectrum against another.

Figure 22:
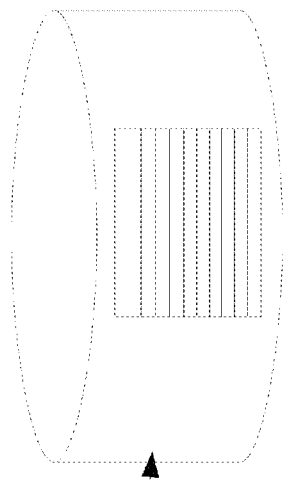
FIG. 22 illustrates a database of spectra, including an identifier for the spectrum, an identifier for the user who obtained the scan, the date and time the scan was obtained, the raw spectrum, the various ortho spectra obtained after processing, and the food ID that was assigned to the scan.

After a spectrum X has been input to the orthogonalizer 705, and the orthogonalizer has completed its calculations, the orthogonalizer can write the ortho spectra it has computed from that spectrum X to a single row of the database of spectra 2200, depicted in FIG. 22. For example, the input spectrum 402 in FIG. 7 can be written to the 4th column, entitled Raw Spectra, in FIG. 22. For example, three ortho spectra can be calculated relative to three reference spectra, and these three ortho spectra can be written by the orthogonalizer to the database of spectra 2200 in that same single row, in the 5th, 6th and 7th columns, entitled Ortho Spectra, in FIG. 22. FIG. 22 depicts a number of reference spectra equal to 3, but this is only for convenience of depiction, and unlikely, although possible. In some embodiments, the orthogonalizer 705 cannot write to the column (depicted as column 8 in FIG. 22) entitled Food ID. In some embodiments, an input spectrum 402 to the spectrum processing system 403 has associated metadata, such as, for example, a globally unique identifier for the spectrum, a globally unique identifier for the user who obtained the spectrum, and an identifier for the date on which the spectrum was created, all of which accompany the input spectrum 402 when it is transmitted or stored, and is written by the spectrum processing system 403, for example, to the 1st, 2nd and 3rd columns in FIG. 22.

In some embodiments, the incoming spectra 402 to the server are analyzed by the spectrum processing system 403 for changes over time that could be attributed to inhomogeneity of the sample. For an example, if the sample is an inhomogeneous food like a soup mix, containing dried peas, dried carrots, and soup powder, then the spectrum of the soup mix over some period of time, as the user moves the spectrometer even slightly, may look like dried peas for a short interval of time, then like dried carrots, then like soup powder, then like dried peas again, and so on. In some such embodiments, the spectrum processing system 403 is capable of: (a) detecting such changes in an input spectrum X; (b) computing subsets Y(0), Y(1), Y(2), . . . which add up to X (except any discarded subsets), each Y(i) of which do not internally exhibit changes that could be attributed to inhomogeneity; (c) adding up some of the Y(i), for example Y(0), Y(3), Y(7), . . . , which do not exhibit differences between them that could be attributed to inhomogeneity; and (d) thereby obtaining sums Z(j), which are thenceforth treated as spectra of different foods within the sample. So, for example, the spectrum for the first short interval, might be put into a first group, the spectrum for the second short interval, where it looks different from how it looked in the first short interval, might be put into a second group, and so on, and the spectrum for the fourth short interval when it looks different again, but similar to how it looked in the first short interval, is put again into the first group.

In some embodiments, with reference to the aforementioned audible sound or other signal emitted by the spectrometer 101 when enough data has been received by the server system 401, when the spectrum processing system analyzes the incoming spectra over time for changes that could be attributed to inhomogeneity of the sample, the spectrum processing system can wait until enough data has been received by the server system 401 for each of the aforementioned groups, before sending a signal to the spectrometer and/or personal computing device that causes the spectrometer and/or personal computing device to emit an audible sound or other signal indicating that enough data has been obtained. For the example of a soup mix, the system can wait until we have enough data to identify all three of the ingredients of the soup mix as dried peas, dried carrots, and soup powder. In some embodiments, the system might use a rule in which the amount of time for which we need to collect data for each group depends on the number of groups. For example, for a homogeneous sample, that rule might specify that we need at least 5 seconds of data; while for a sample consisting of two types of foods, we need at least 4 seconds of each type, which might take a total of 11 seconds; and for the example of the soup mix, with three types of foods, we need at least 3 seconds of each type, which might take a total of 14 seconds.

Some or all of the capabilities and process steps described herein related to possible inhomogeneity of the sample (but without limitation) could be carried out by the spectrometer 101 or by the personal computing device 103 instead of by a server 102. For example, the processing and/or analysis of the incoming spectra, and subsequent analysis, and detection of the number of different groups of spectra, and the amount of time each group has been scanned so far, can be performed on the personal computing device to improve the user experience.

Figure 8:
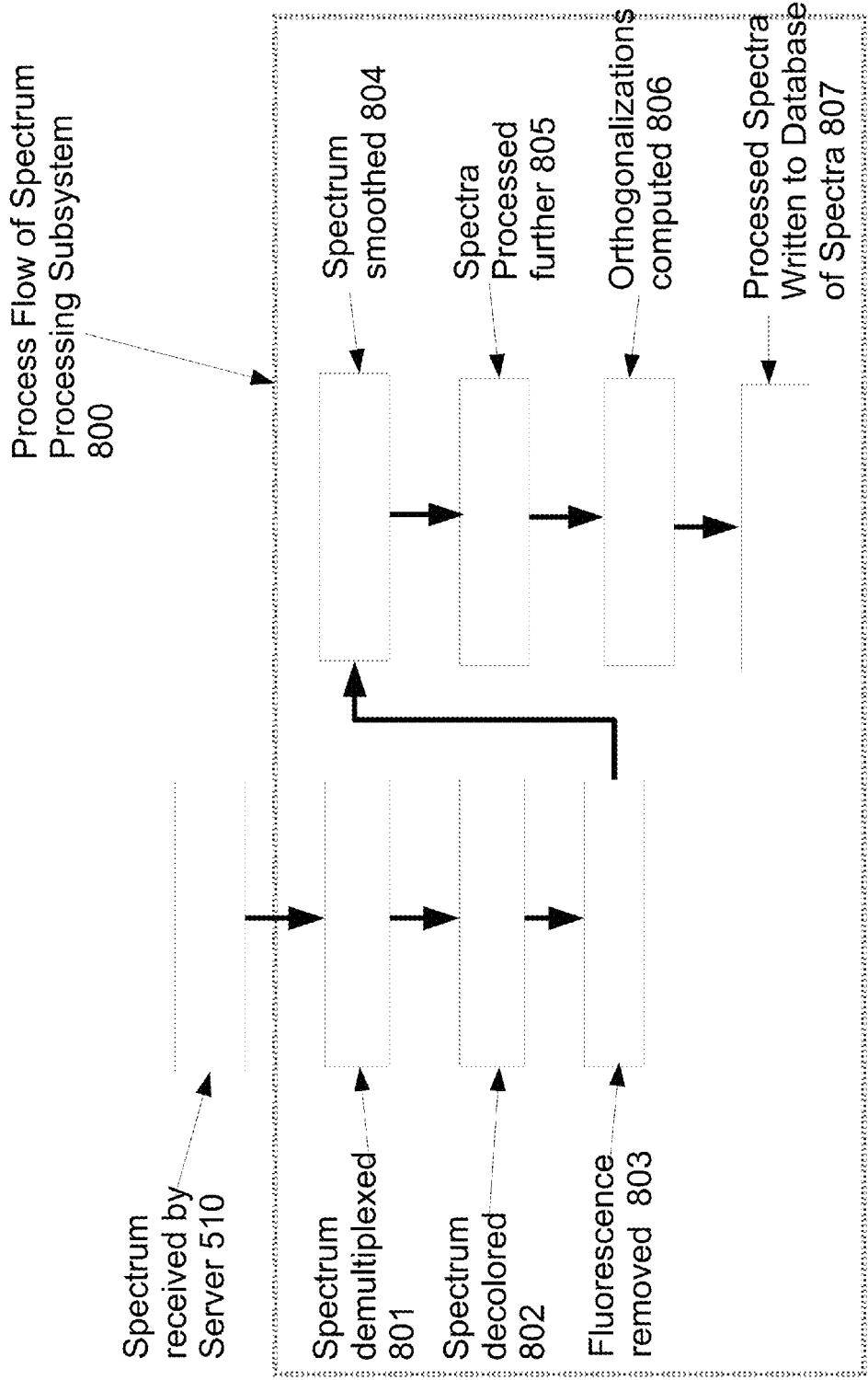
FIG. 8 depicts a process flow 800 of a method of operation of the spectrum processing subsystem of the server system, as depicted in FIG. 7.

FIG. 8 depicts a process flow 800 of a method of operation of the spectrum processing subsystem of the server system, as depicted in FIG. 7.

FIG. 8 depicts a step 510, at which an input spectrum has been received by the server and is input to the spectrum processing subsystem. This input spectrum contains one or more spectra of the sample 105 gathered through the operation of the detector 207 when the light source 204 is emitting light, and one or more spectra of the sample gathered by the detector when the light source is not emitting light.

FIG. 8 depicts a step 801, at which the spectrum is demultiplexed, and specifically: (a) a single spectrum of the sample is calculated in response to those of the aforementioned spectra that were gathered when the light source was emitting light; (b) a single spectrum of the sample is calculated in response to those of the aforementioned spectra that were gathered when the light source was not emitting light; and (c) this calculation is performed by, at each index or position or offset in the array, adding the magnitudes of the corresponding spectra at that index or position or offset (those skilled in the art will recognize this as point wise addition).

FIG. 8 depicts a step 802, at which the spectrum is decoloured, and specifically: (a) the decolorizer 702 subtracts the spectrum of the sample calculated from the spectra that were gathered when the light source was emitting light from the spectrum of the sample calculated from the spectra that were gathered when the light source was not emitting light; and (b) this calculation is performed by, at each index or position or offset in the array, subtracting the magnitude of the first at that index or position or offset from the magnitude of the second at the same index or position or offset (those skilled in the art will recognize this as point wise subtraction).

At step 803, in some embodiments, fluorescence is removed from the spectrum. Specifically, in some embodiments: (a) a cubic spline with the same domain as the spectrum and three segments is calculated (this spline could, for example, be the usually unique such spline which is, at each point, less than the spectrum, but whose Euclidean distance from the spectrum is least possible); and (b) this spline is subtracted from the spectrum. It is expected that such a spline will closely resemble the fluorescence of the sample, and that the result of the subtraction, by point wise subtraction, substantially resembles the Raman spectrum of the sample. In some embodiments, this step 803 is skipped.

At step 804, in some embodiments, the spectrum is smoothed. Specifically, in some embodiments, the value of the spectrum at each element of the domain is replaced by the average value of the spectrum at the three values of the domain centred at that element, possibly weighted with weights ¼, ½, and ¼. The result of this step is expected to usually show substantially fewer sudden changes and usually substantially reduce the relative effect of noise on the spectrum. In some embodiments, this step 804 is skipped.

At step 805, in some embodiments, the spectrum is processed further. In one example, the spectrum is replaced by its first differences. That is, the value of the spectrum at each element of the domain is replaced by the difference between the values of the spectrum at that element and the previous element (i.e. the next smaller wave number). The resulting spectrum is expected to resemble the first derivative of the spectrum, were it a differentiable function. In another example, the spectrum is replaced by its second differences. That is, the value of the spectrum at each element of the domain is replaced by sum of the values of the spectrum at the two adjacent elements minus twice the value of the spectrum at that element itself. The resulting spectrum is expected to resemble the second derivative of the spectrum, were it a twice differentiable function. In some embodiments, this step is skipped.

At step 806, in some embodiments, the spectrum is input to the orthogonalizer 705 directly after step 802. In other embodiments, the spectrum is input to the orthogonalizer after any or all of steps 803, 804, and 805.

In some embodiments, for each reference spectrum Y in the list of reference spectra against which it computes orthogonalizations, the orthogonalizer 705 computes the projection P of the spectra X input to the orthogonalizer onto the reference spectrum Y, and subtracts this projection P from the spectrum X.

In some embodiments, at step 807: (a) the orthogonalizer writes each of the resulting difference spectra X−P, called ortho spectra, from step 806, to the database of spectra 2200, depicted in FIG. 22; (b) the orthogonalizer writes the ortho spectra it has computed to a single row of the database of spectra 2200 (for example, if the demultiplexer 701 wrote the input spectrum received in step 510 to the 4th column, entitled Raw Spectra, of a row in FIG. 22; then the three ortho spectra calculated relative to three reference spectra are written by the orthogonalizer to the database of spectra 2200 in the 5th, 6th and 7th columns, entitled Ortho Spectra, in the same row, in FIG. 22. FIG. 22 suggests that the number of reference spectra used is 3, but this is only for convenience of depiction); (c) the orthogonalizer does not write to the 8th column entitled Food ID, but rather leaves this blank or uninitialized; and (d) metadata associated with the spectrum input to the spectrum processing system at step 510, such as for example a globally unique identifier for the spectrum X, a globally unique identifier for the user who obtained the spectrum X and the date on which the spectrum X was created, are written by the demultiplexer 701 to the database of spectra 2200, for example in the 1st, 2nd and 3rd columns in FIG. 22.

Spectrum Analysis

Figure 9:
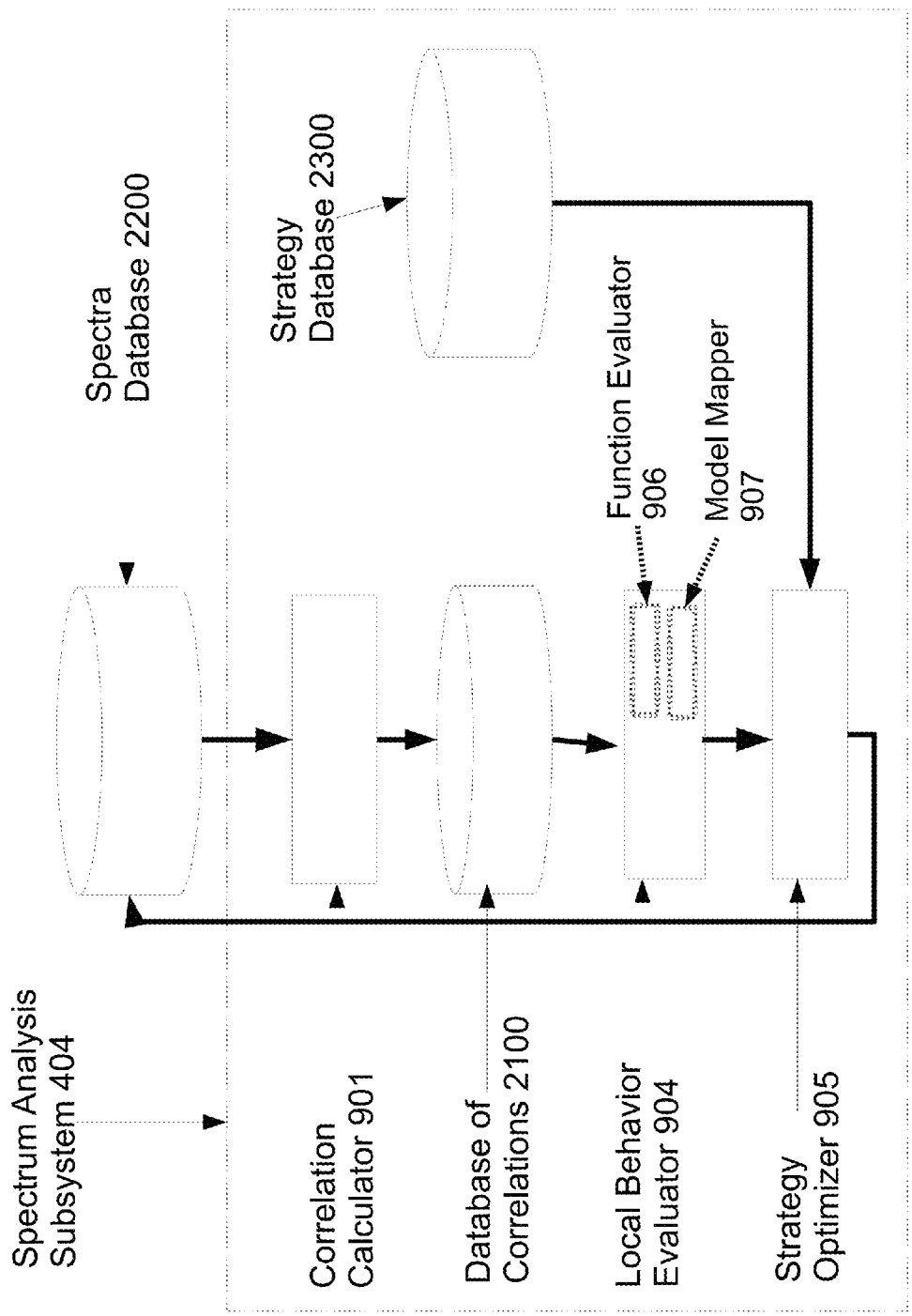
FIG. 9 shows a block diagram of the spectrum analysis subsystem of a server system, including means for analyzing spectra of samples, identifying the samples and facts about them, and storing these in a food database.
Figure 10:
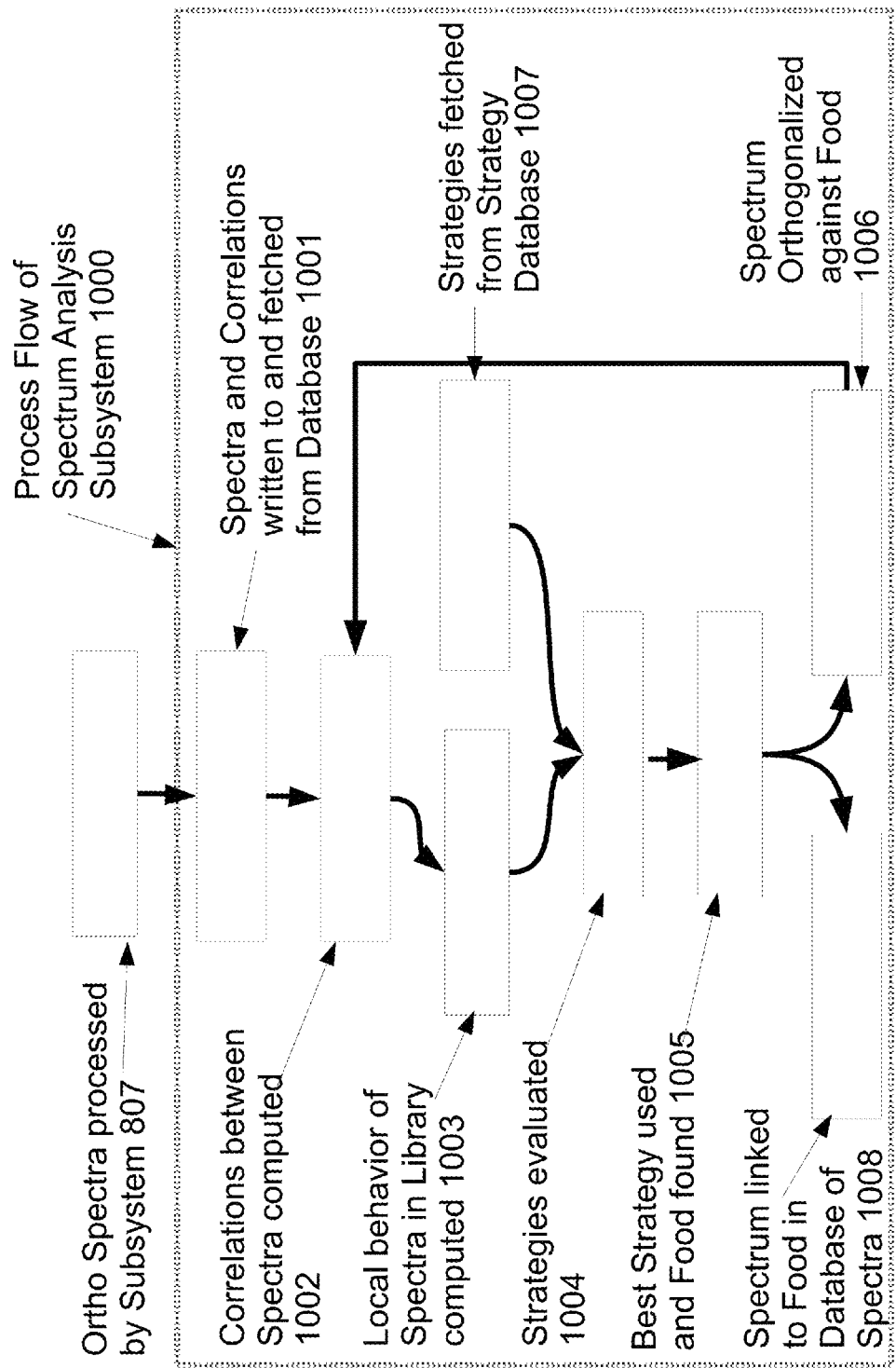
FIG. 10 depicts the process flow 1000 of a method of operation of the spectrum analysis subsystem of the server system, as depicted in FIG. 9.

FIG. 9 shows a block diagram of the spectrum analysis subsystem of a server system, including means for analyzing spectra of samples, identifying the samples and facts about them, and storing these in a food database.

FIG. 9 depicts the spectrum analysis subsystem 404, including a correlation calculator program 901, a local behavior evaluator program 904, a strategy optimizer program 905, a database of correlations 2100, and a database of strategies 2300. In some embodiments: (a) the spectrum analysis subsystem 404 is connected to the spectrum processing subsystem 403; (b) the spectrum analysis subsystem 404 is responsive to output from the spectrum processing subsystem 403; (c) within the spectrum analysis subsystem 404, output from the spectrum processing subsystem 403 to the spectrum analysis subsystem 404 can be input to the correlation calculator program 901, which can write to the database of correlations 2100 and can output to the local behavior evaluator 904; (d) the local behavior evaluator 904 is responsive to output from the correlation calculator 901, and is connected to, and can query, the database of correlations 2100, and receive data indicating correlations between spectra stored therein; (e) the strategy optimizer 905 is connected to the local behavior evaluator 904, and is responsive to the output of the local behavior evaluator 904; (f) the strategy optimizer 905 is connected to, and can query, the strategy database 2300, and receive data indicating strategies stored therein; and (g) the strategy optimizer 905 can write its output to the database of spectra 2200. In some embodiments, the spectrum analysis subsystem 404 can query the spectrum processing subsystem and receive data from the database of spectra 2200.

Figure 21:
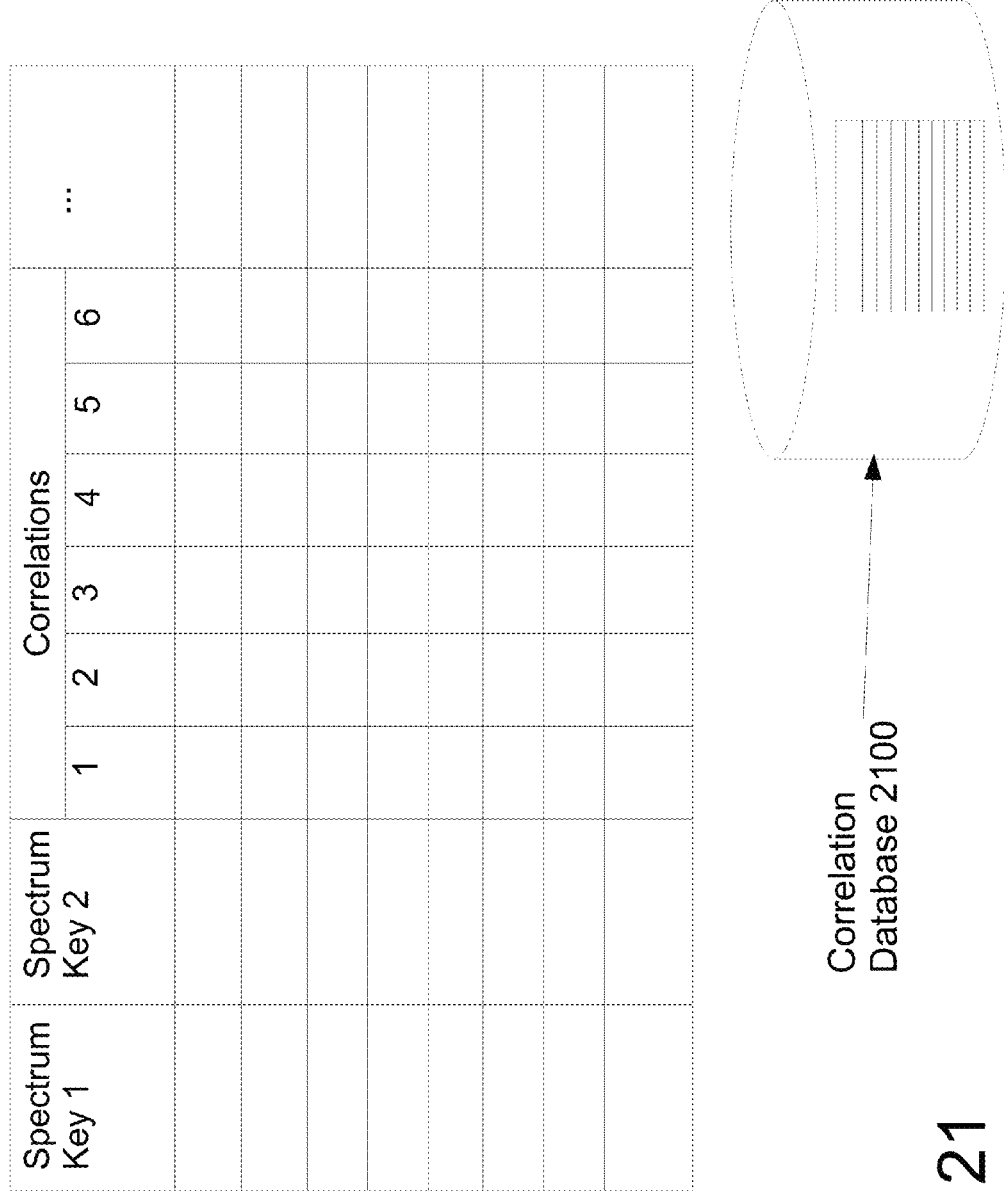
FIG. 21 illustrates a database of correlations between spectra, calculated in various ways.

One embodiment of the database of correlations is depicted in FIG. 21. In a theoretical embodiment, this database contains one row for each unique pair of distinct spectrum keys, but this is not generally practical since a million spectra would then imply a database with almost 400 billion rows. However, the reader may find it helpful to initially envision the database of correlations in this way. In some embodiments, for each pair of spectrum keys for which a row is present in the database of correlations, the correlations depicted in FIG. 21 are the Euclidean distance between the corresponding ortho spectra of the two spectra corresponding to that pair of spectrum keys. That is, the entry in the 1st row and 3rd column of FIG. 21 might be the Euclidean distance between the ortho spectra written in the 1st and 2nd rows of FIG. 21 in the 5th column. In other embodiments, the correlations might be dot products or distances under other metrics, such as the sup metric. In some embodiments, the correlation calculator 901 can act on input of a spectrum, and can write a new row for some pairs of distinct spectrum keys where one of the keys is the key of the spectrum input, and the other key is the key of a spectrum already in the database of spectra 2200. In some embodiments, pairs of spectra can be chosen so that given a spectrum X, the specific spectra Y for which there is a row in the database of correlations, the entries of which in the first two columns are the indices for X and Y in some order, number about 100,000. For each X, the aforesaid specific Y's can be selected in such a way that, for each column of correlations, Y's are selected randomly or pseudo-randomly in such a way that if the correlation between X and Y is in a particular percentile of all the correlations between X and a possible Y, then the Y can be selected with probability corresponding to that percentile. In some embodiments, statistical methods known to those of skill in the art can be used to select specific Y's for an X without computing all such correlations.

In some embodiments: (a) the local behavior evaluator 904 includes a function evaluation submodule 906; and/or (b) the function evaluation submodule 906 can take as input a spectrum key K and a functional computer program P, and, with reference to a particular column of correlations in the database of correlations 2100, can execute the functional computer program P on input of the spectrum key K, and can thereby obtain an output which is a spectrum key, which we denote P(K).

In some embodiments, the functional computer programs P are programs obtained using techniques from machine or statistical learning. For example, the functional computer programs may implement methods of decision tree learning, association rule learning, artificial neural networks, inductive logic programming, support vector machines, clustering, or Bayesian networks. In some embodiments, the functional computer programs: reference only the aforesaid particular column of correlations, along with the first two columns, in the database of correlations 2100; take one spectrum key as input; and produce only one spectrum key as output. In some embodiments, the functional computer programs P are compositions of an "atomic" computer program, which takes as inputs a spectrum key K and an integer i, and which is substantially a hash H of arrays, which makes the aforesaid column of correlations available, so that the array H(K) is an array of spectrum keys H(K)(i) such that H(K)(0) is the spectrum key most closely correlated to K according to that column of correlations, H(K)(1) is the spectrum key next most closely correlated, and so on.

In some embodiments: (a) the local behavior evaluator 904 also includes a model mapper submodule 907; (b) the model mapper can take as input a spectrum key K and an array M of functional computer programs P(0), P(1), . . . as described in the previous paragraph, which we call a model generator; (c) the model mapper can carry out a computation, with reference to the food database 2000 and with reference to a particular column of correlations in the database of correlations 2100, where the column of correlations used is the same for each functional computer program in the model generator M; (d) the model mapper can carry out this computation by taking the spectrum key K and each functional computer program P(0), P(1), . . . as inputs to the function evaluation submodule 906, with reference to that same particular column of correlations in the database of correlations; (e) the model mapper can thereby obtain the outputs P(0)(K), P(1)(K), . . . ; (f) the model mapper can evaluates the food IDs F(0), F(1), . . . corresponding to the outputs P(0)(K), P(1)(K), . . . , with reference to the spectra database 2200; (g) the model mapper can evaluate the parent food IDs G(0), G(1), . . . corresponding to these food IDs, with reference to the food database 2000; (h) the model mapper can perform a simple computation on the IDs G(0), G(1), . . . , only evaluating for some i and j whether G(i) equals G(j), and outputs some simple output, typically a bit string of length between 5 and 100; and (i) the output of the model mapper is invariant under renaming of distinct IDs G(0), G(1), . . . . In some embodiments, the process of finding the parent food ID can be repeated, so that in fact the grandparent food IDs, or even the great-grandparent food IDs are found.

In some embodiments: (a) the local behavior evaluator 904 can take as input a spectrum key K and a stored array of model generators, and with reference to the spectra database 2200 and food database 2000, can take each model generator M in the stored array in turn, and execute the model mapper program on input of K and that model generator M; (b) the local behavior evaluator can store these outputs, one by one, to the entries of an array, called the local behavior of the spectrum key K, relative to the spectra database and the food database. For example, this array can be an array of bit strings B, one bit string B(M,K) for each model generator M in the stored array of model generators, with the position of the (reference to the) bit string B(M,K), in the local behavior array, equal to the position of M in the stored array of model generators. The column of correlations used can vary depending on the model generator.

In FIG. 9, the spectrum analysis subsystem 404 also includes a strategy optimizer 905. A strategy, as referred to herein, is a data structure that comprises a particular model generator M and a particular bit string B that might, or can, in principle, be output by the action of the model mapper on a spectrum key and the model generator M, with reference to the spectra database 2200 and with reference to the food database 2000. In some embodiments: the strategy optimizer can: (a) apply an ordered list of strategies to a particular input spectrum key K; and (b) generate such an ordered (prioritized) list of strategies.

Regarding the ability of the strategy optimizer to apply an ordered list of strategies to a particular input spectrum key K, in some embodiments: (a) on input spectrum key K, the strategy optimizer can take the strategies (M,B) in the list of strategies, in order, and, for each one, compare the output of the model mapper program B(M,K) on input of the model generator M and spectrum K, which it can read from the output of the local behavior evaluator 904, with the bit string B; (b) if these bit strings B(M,K) and B are equal, then the strategy optimizer 905 can write the food ID of the closest spectrum to the input spectrum, as calculated from the column of correlations corresponding to the model generator M in the database of correlations 2100, into the database of spectra 2200 in the row corresponding to the input spectrum and in the column entitled Food ID (and terminate); (c) if these bit strings are not equal, then the strategy optimizer can repeat this process with the next strategy in the list of strategies; (d) if the list of strategies is exhausted without the bit strings B(M,K) and B ever being equal, then the strategy optimizer 905 can write "no food found" into the database of spectra 2200 in the row corresponding to the input spectrum (and terminate) and in the column entitled Food ID.

In some embodiments, the food ID recorded in the database of spectra 2200 is not the food ID of the closest spectrum to the input spectrum, as calculated from the column of correlations corresponding to the model generator M in the database of correlations 2100. Instead, the parent food ID may be recorded, or the grandparent food ID, or even the great-grandparent food ID. The particular food ID to be recorded can be responsive to the closeness of the match, or the confidence of the match, or the type of food. For example, the sample might be identified to a specificity so that the confidence in the identification is at least 99%. The SKU might be identified, or, if the confidence is high enough, even the batch of the sample, described for example by geographical area or time period might be identified. In the context of this invention, a stock-keeping unit (SKU) is a product with a barcode i.e. a UPC or EAN. Alternatively, if the confidence is not so high, then the type of food only might be identified. These embodiments can do this by choosing the most specific among food ID, parent food ID, grandparent food ID, great-grandparent food ID, etc. for which the confidence in the identification is at least some set value, like 99%.

Regarding the ability of the strategy optimizer to generate such an ordered or prioritized list of strategies, in some embodiments, the strategy optimizer can (a) take all strategies (M,B) in a stored list of all strategies to be considered, in any order, and, for each combination of a strategy (M,B) and a possible input spectrum K, evaluate B(M,K), the output of the model mapper program on input of the model generator M and the spectrum key K, and compare it with B; (b) if these bit strings are equal, compare the parent (or grandparent etc.) food ID of the closest spectrum to the input spectrum, as calculated from the column of correlations corresponding to the model generator NI in the database of correlations 2100, with the corresponding parent (or grandparent etc.) food ID of the possible input spectrum K itself; (c) if these food IDs are equal, record the strategy (M,B) comprising the model generator M and bit string B as correctly predicting the possible input spectrum K; (d) if these food IDs are not equal, record the strategy (M,B) as incorrectly predicting the possible input spectrum K; (e) if the aforementioned bit strings are not equal, record (M,B) as inapplicable to the spectrum key K; (f) estimate the effectiveness of each strategy (M,B) in the stored list of all strategies to be considered by computing how many input spectra K it computes correctly and how many incorrectly; (g) order the list of strategies in terms of how effective they are, by, for example, listing the most effective strategy first and so on; and (h) recording a strategy as more effective than another strategy if the fraction of correctly computed spectra is higher, or, if equal, if the number of spectra which are correctly computed is higher.

In some embodiments: (a) the stored list of all strategies to be considered is generated in an obvious manner to one skilled in the art from a stored list of all model generators, and for each model generator, a list of all possible bit strings B that could be the output of the model mapper program on input of the model generator M and any spectrum key K; (b) the list of all possible model generators is generated by taking all initial segments of length less than some chosen number, from a family of 10 ordered master lists of functional computer programs; and (c) each aforementioned master list of functional computer programs is a list of the first 50 functional computer programs, ordered in some intuitively reasonable, but hand-chosen, manner (for example, in terms of simplicity, brevity, effectiveness, computation time etc.)

FIG. 10 depicts the process flow 1000 of a method of operation of the spectrum analysis subsystem of the server system, as depicted in FIG. 9.

FIG. 10 depicts a step 601, at which ortho spectra have been created and written to the database of spectra 2200 by the spectrum processing subsystem 403, the process flow for which is depicted in FIG. 8 and described in detail herein, and have been input to the spectrum analysis subsystem 404.

FIG. 10 depicts a step 1001, at which some rows are read from the database of correlations 2100, as depicted by way of example in FIG. 21. Also, some ortho spectra are read from the database of spectra 2200, as depicted by way of example in FIG. 22.

FIG. 10 depicts a step 1002 at which: (a) the correlation between each of the ortho spectra input in step 601 and each of the various corresponding ortho spectra read from the database of spectra is computed, possibly as the Euclidean distance; and (b) these correlations are written to the database of correlations, for example in a new row whose first and second column entries are, in some order, the spectrum key of the ortho spectrum read from the database of spectra and the spectrum key of the spectrum input in step 601. In alternative embodiments, the correlations might be dot products or distances under other metrics, such as the sup metric.

FIG. 10 depicts a step 1003, in which the local behavior is evaluated as follows: (a) the spectrum key K of the ortho spectra input in step 601 is taken as an input with reference to a defined array of model generators M, where each model generator M is an array $P(0), P(1), \ldots$ of functional computer programs; (b) calculations are performed for each of the model generators M in the defined array, one after the other; (c) in particular, for a particular model generator M, which is an array of functional computer programs $P(0), P(1), \ldots$, two calculations are done for each of the functional computer programs in the array, one after the other; (d) the first of these calculations executes the functional computer program on input of the spectrum key K with reference to a particular column of correlations in the database of correlations 2100, to produce an output, which is a spectrum key $P(i)(K)$; and (e) the second of these calculations takes each output $P(i)(K)$ of the first calculation, and with reference to the spectra database 2200, finds the food IDs corresponding to each output, and then, with reference to the food database 2000, finds the parent food ID corresponding to each food ID, and produces outputs $G(0), G(1), \ldots$, which are the parent food IDs. In some embodiments, the process of finding the parent food ID is repeated, so that in fact the grandparent food ID, or even the great-grandparent food ID is found, and the outputs $G(i)$ are grandparent food IDs etc.

In some embodiments, once these two calculations in step 1003 are done for each of the functional computer programs in a particular model generator: (a) the model mapper computer program is executed on the input of all of these last found food IDs $G(0), G(1), \ldots$ of the second calculation, with reference to that same particular column of correlations in the database of correlations; (b) the output bit string of the model mapper program is computed for each model generator in the defined array, and the array of bit strings thus computed is the local behavior of the spectrum key K, relative to the spectra database and the food database, which is input for step 1004.

FIG. 10 depicts a step 1007 at which: (a) an ordered list of strategies is fetched from the strategy database 2300, where a strategy is a pair (M,B) comprising a particular model generator M and a particular bit string B that might, or can in principle, be output by the action of the model mapper on that model generator M and a spectrum key K, with reference to the spectra database 2200 and with reference to the food database 2000; (b) this list of strategies is generated anew periodically, but this is not necessarily done each time step 1007 is performed; (c) the generation of a new list involves something like the repeated execution of step 1004; and (d) when the ordered list of strategies is generated anew, strategies may be ordered differently, new strategies may appear in the list, and old strategies may disappear from the list.

FIG. 10 depicts a step 1004 at which: (a) the strategy optimizer applies the strategies in the ordered list of strategies to the given input spectrum key K, by taking each strategy (M,B) in the list of strategies, in order, and, for each one, comparing the previously computed local behavior B(M,K) of the input spectrum key K for the model generator M with B;

(b) if these bit strings are equal, the strategy optimizer proceeds to step 1005 using the strategy (M,B) as the best strategy; and (c) if these bit strings are not equal, then the strategy optimizer tries the next strategy (that is, it repeats this process with the next strategy in the list of strategies).

FIG. 10 depicts a step 1005 at which the strategy optimizer uses the column of correlations in the database of correlations 2100 corresponding to the model generator M from the strategy (M,B) found at step 1004 to compute the closest spectrum to the input spectrum K, and looks up the food ID (or parent food ID etc. as discussed herein) of that closest spectrum in the database of spectra 2200.

FIG. 10 depicts a step 1008, at which the strategy optimizer writes the food ID (or parent food ID etc. as discussed herein) found at step 1005 into the database of spectra 2200 in the row corresponding to the input spectrum key K.

At any time, the ordered list of strategies fetched at step 1007 can be calculated anew. This is done by performing step 1004 for each possible strategy (M,B) and each possible input spectrum K, except that if the aforementioned bit strings are equal, then the parent (or grandparent etc.) food ID of the closest spectrum to the input spectrum is compared with the parent (or grandparent etc.) food ID of the input spectrum itself, and if these are equal then the strategy (M,B) is recorded as correctly predicting the input spectrum, whereas if not, then the strategy (M,B) is recorded as incorrectly predicting it. After this is done for each possible strategy (M,B) and each possible input spectrum K, the effectiveness of each strategy is estimated by counting how many input spectra are recorded as having been computed correctly and how many incorrectly. The list of strategies is then ordered in terms of how effective they are.

FIG. 10 depicts a step 1006 and an arrow from step 1006 back to step 1002. The arrow indicates that steps 1002, 1003, 1004, 1005, and 1006 can be iterated to find ingredients, subfoods, substances, chemicals, and families of chemicals, within the food sample A. Each such iteration uses a food, ingredient, subfood etc. B against which the spectrum of A is orthogonalized at step 1006. In various embodiments, at step 1006, this food, ingredient, subfood etc. B can be found by: (a) when the food sample A has been identified, with reference to the food database and data therein that relates to scans by other users and/or information obtained from 3rd parties; (b) when the food sample A cannot be identified, by calculating the food, ingredient, subfood etc. B that is the most likely ingredient or subfood etc. based on (i) how commonly B is found in identified foods similar to A (for example, with similar spectra); (ii) how highly B is correlated with A (e.g. using the dot product); (iii) how large a concentration of B is present in that linear combination of common ingredients which is smaller than but closest to the spectrum of A. In one example, such possible B are listed in order under each of criteria (i), (ii), and (iii), and then the B with the lowest sum of indices in each ordered list is chosen. In some embodiments, in the second iteration of steps 1002, 1003, 1004, 1005, and 1006, all computations and correlations etc. are calculated after all spectra are orthogonalized against B, and so on.

In some embodiments, a food sample A may be identified with high confidence while the concentration of, for example, a chemical B within A may be too low to identify B directly through the aforementioned iteration. For example, the data in a single scan of a particular duration might only enable the detection of chemicals that are present at sufficiently high concentrations. For a specific example, the system might iterate the process depicted in FIG. 10 and thereby, with 99% confidence, be able to detect concentrations of 400 ppm (parts per million) in a scan of duration 1.5 sec, 200 ppm in 8 sec, 100 ppm in 30 sec, 50 ppm in 2 min, 20 ppm in 14 min, 10 ppm in 1 hr and 5 ppm in 4 hrs. In that specific example, the food sample A itself might however be identified with 99.99% confidence. In such an example, the data in multiple scans by many users can be assembled, when the confidence is sufficiently high that they are all of the same food. That is, using the rough durations above in the example, rather than requiring 1 hr to detect a chemical at 10 ppm, the data of 1000 scans, each of 3 seconds, can be assembled so that using such data from the food database and spectra database, derived from the spectra gathered by users of the system, a user performing a 3 second scan could get information about chemicals present at a concentration of 10 ppm. In such an example, with enough users, say 100,000 scans of 3 seconds, the system could even detect chemicals at concentrations of 1 ppm.

In some of the embodiments described above, a scan is first used to identify a food, and then the scan is combined with other scans of the same food to perform an analysis that is able to detect chemicals at low concentrations. For example, these other scans could be scans by other users, or they could be scans performed in a laboratory with more sophisticated equipment. In some cases, once the food is identified, information about that food can be obtained from laboratory analyses using various methods of spectrometry or chemometrics, or simply from published research reports. In some embodiments, information about the possible presence of a given chemical in a food is obtained by using one or more, or a combination of, methods, including (a) detecting the chemical from a single scan of a sample (which we call single direct detection); (b) detecting the chemical by combining multiple scans of the same food (which we call crowd direct detection); or (c) deducing the concentration of the chemical from 3rd party information (which we call indirect detection). In some such embodiments, the system has no inherent lower limits on the concentrations of chemicals that can be detected. Instead, in those embodiments, as the concentration of a chemical decreases from 4000 ppm to 50 ppm to 1 ppm to 100 ppb, the system can use a continuum of single direct detection, crowd direct detection, and indirect detection, changing the emphasis on each method towards the one that best handles the relevant concentration. The relative emphasis on each method can be responsive to various factors such as, for example: (i) how specifically the food has been identified from the scan and the confidence in that identification; (ii) the relative strength or intensity of the signal attributed to that chemical, and how easily the signal from that chemical can be separated or extracted from the scans of the samples; (iii) the acceptable rates (possibly responsive to business rules or marketing preferences or regulatory rules or guidelines) for false positives and false negatives; (iv) the other characteristics of the scans. For some specific examples, crowd direct detection could be used, by taking those scans from a particular time period or taken at a particular location, to detect a chemical contaminant (or spoilage) in a particular batch of a food. For another specific example, indirect detection could be used to first identify a fish sample as halibut, and then report that it likely contains 240 ppb of mercury, based on FDA reports, even though not enough scans are available to detect this directly.

In embodiments in which the spectrometer 101 is integrated with, or used in conjunction with, a device that can estimate the volume of a sample, the estimates of the relative concentration of ingredients, subfoods, substances, chemicals, and families of chemicals, within a sample, can be converted from relative (for example, per serving) estimates to absolute estimates. In some such embodiments, the spectrometer 101 is also integrated with, or used in conjunction with, or implement, a method that enables the user to provide input describing the food leftover from a meal. In one example, the user can type in a description, graphically indicate a proportion, or upload a photograph of the leftover food on the plate. In some such embodiments, the system can track the user's overall consumption of ingredients, subfoods, substances, chemicals, and families of chemicals.

In some embodiments, the operation of the spectrum analysis subsystem 404, and in particular the correlation calculator 901 and/or the strategy optimizer 905 are responsive also to: data in the user profile database 1900, such as foods previously or often scanned by that user or by other users in the same household or geographically nearby; and/or data in the food database 2000, such as foods available geographically nearby in stores or restaurants.

User Profile

Figure 11:
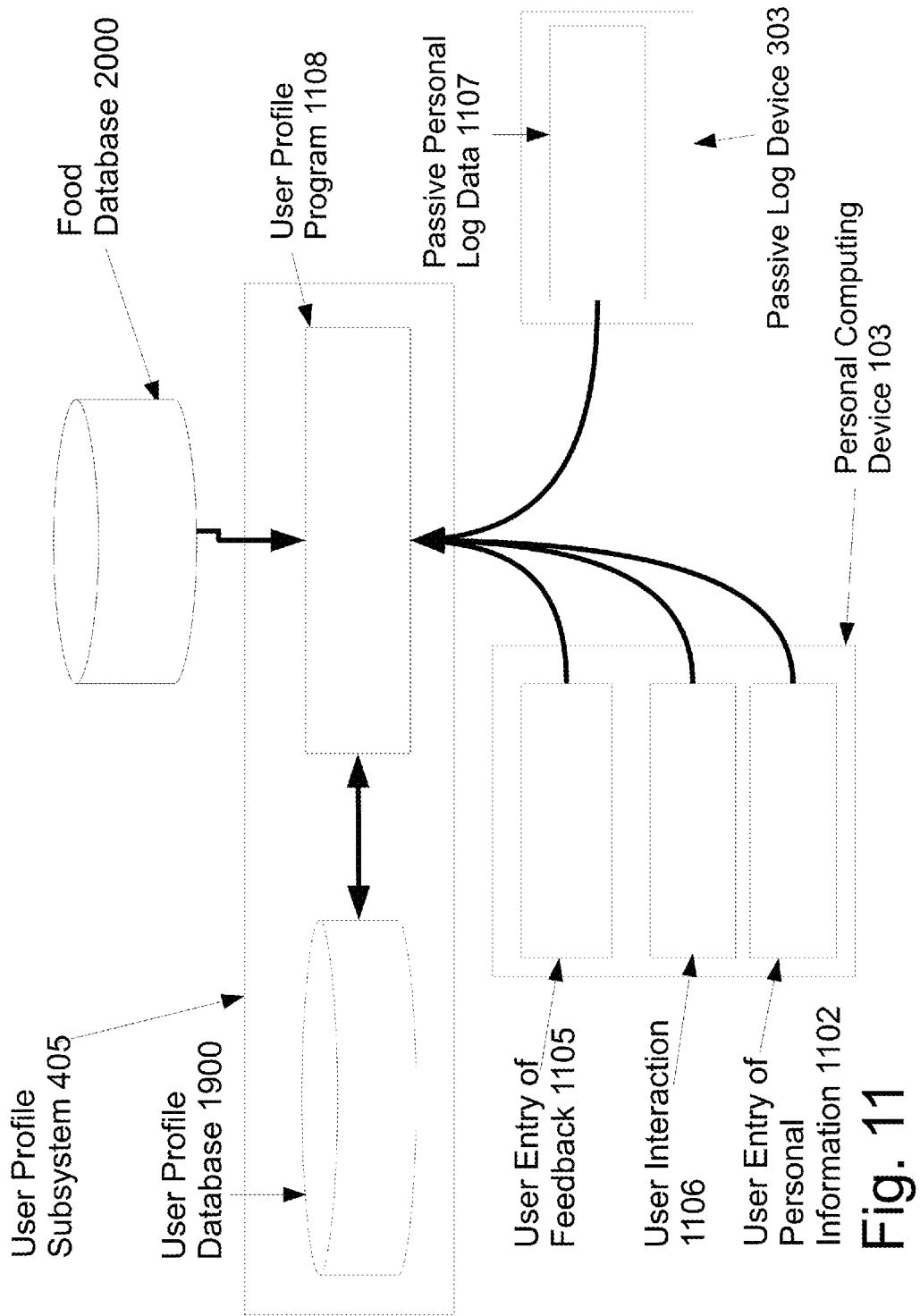
FIG. 11 shows a block diagram of the user profile subsystem of a server system, including means for receiving, organizing, and providing personalized data about food and usage, feedback, and personal log data.

FIG. 11 shows a block diagram of the user profile subsystem of a server system, including means for receiving, organizing, and providing personalized data about food and usage, feedback, and personal log data.

The user profile subsystem 405 includes a user profile program 1108 and a user profile database 1900. The user profile program 1108 can read from, and write to, the user profile database 1900. The user profile subsystem 405 is connected to the ranking subsystem 406, the personal computing device 103, and the passive log device 303. In some embodiments, the user profile subsystem 405 is responsive to both communications from the passive log device 303 that contain passive personal log data 1107 and to communications from the personal computing device 103 that contain user entered feedback 1105, records of user interaction 1106, and personal information 1102 that is entered by the user, created automatically (for example, real-time GPS location), or obtained in another way. In some embodiments, the user profile subsystem 405 is responsive to output from the ranking subsystem 406, and the ranking subsystem 406 is responsive to output from the user profile subsystem 405.

In some embodiments, the spectrometer 101 itself can be used as a passive log device 303. That is, the spectrometer can be used by the user 104 to scan his or her fingers, skin, fingernails, tongue, saliva, urine, faeces etc. The spectra thereby obtained might then be responsive to the chemical composition of such samples, for example Raman spectra of skin responsive to the chemical composition below the skin (e.g. oxygen level or glucose level of the blood) or the absorption spectra of exhaled air responsive to differences between normal and disease-state glucose metabolism.

In some embodiments, the passive personal log data 1107 includes data about the user's environment. In some such embodiments, the spectrometer 101 itself is capable of being used as the passive log device 303. For example then, the passive personal log data can include: (a) the spectrum of sunlight, which may be influenced by the absorption of water, ozone, carbon dioxide or other gases, and such a scan can then be used as an environmental indicator; (b) air pressure data, which can be correlated with the user's migraine headaches; (c) air temperature, humidity, cloud cover, or other meteorological data; and/or (d) carbon monoxide or natural gas levels in the environment. In some embodiments, GPS can be used to correlate environmental passive personal log data of different users so that data obtained by one user can be used for the benefit of another nearby user.

In some embodiments, the passive log device 303 includes, without limitation, the functionality of a metabolic measuring device, a wearable energy tracking device, a self-quantification device, and/or a wearable real-time measuring device such as an accelerometer or pedometer. In some embodiments, the passive personal log data 1107 includes, without limitation: data related to the metabolic rate; body composition data or body mass index (BMI) data; data related to daily calorie or energy expenditure; data that tracks sleep pattern, sleep quality, mood, and/or stress level; measurements of calories burned; data related to motion, posture, heart rate, eye movement, blood oxygen level, galvanic skin response, and/or skin temperature; and/or measurements of nutritional state, such as a real-time estimate of which macronutrient is being metabolized.

Figure 12:
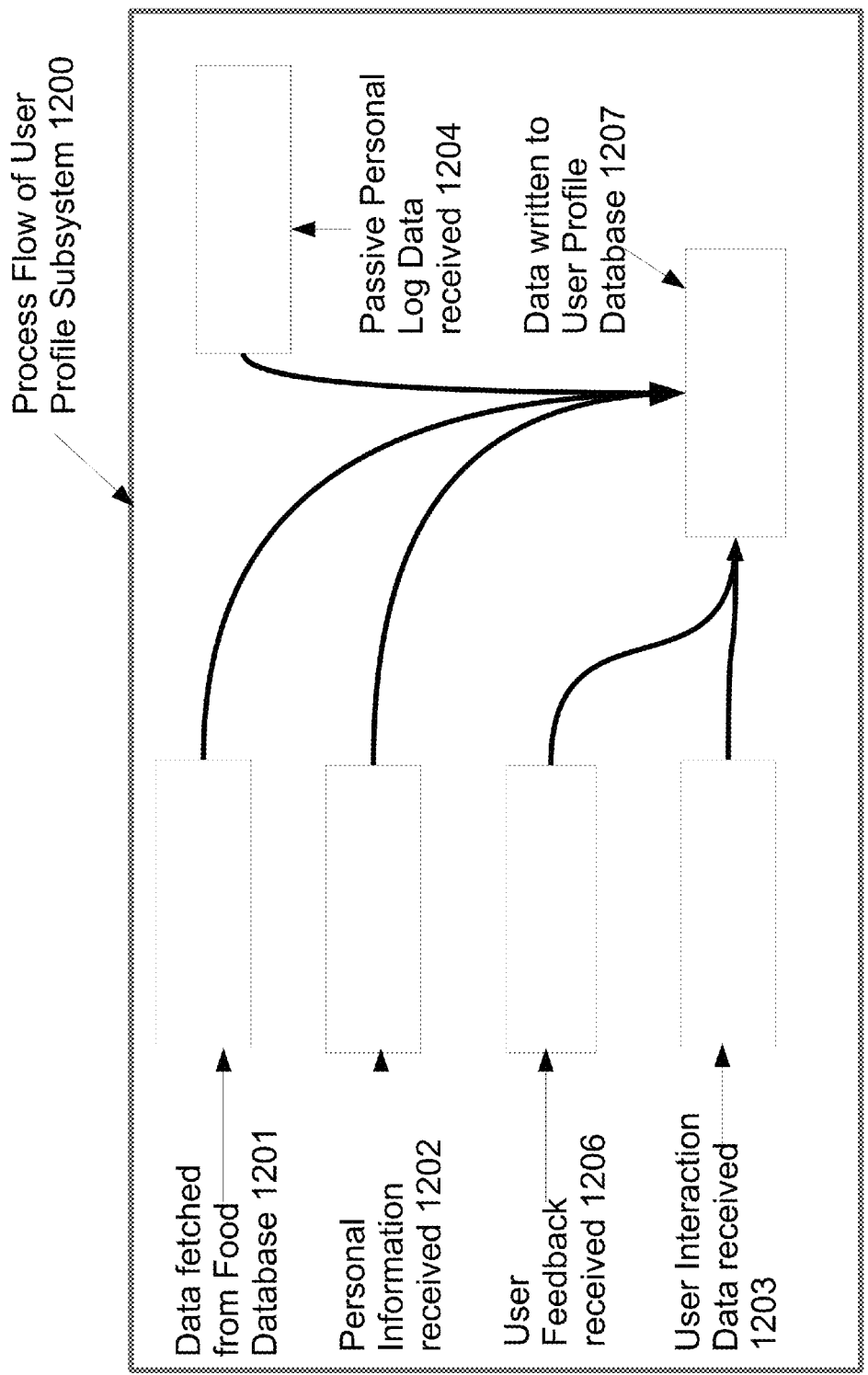
FIG. 12 depicts the process flow 1200 of a method of operation of the user profile subsystem of the server system, as depicted in FIG. 11.

FIG. 12 depicts the process flow 1200 of a method of operation of the user profile subsystem of the server system, as depicted in FIG. 11.

In step 1201, food consumption data is fetched from the food database, with reference to the database of spectra; possibly whenever a spectrum is written to the spectra database 2200. For example, with reference to FIG. 22, whenever a row written to the spectra database has 2nd column, for the user, set to X, and the last entry, for the food ID, set to Y, and, with reference to FIG. 20, the row of the food database 2000, whose first column, for the food ID, is set to Y, has a Food 1 ID (or Food 2 ID, Food 3 ID, etc.) set to Z, then Z is written, with reference to FIG. 19, to the food ingested field of a new row of the User Profile Database 1900 whose user field is set to X. Extending that example, if the row of the food database 2000, whose first column, for the food ID is set to a Z, has a parent food ID (or Food 1 ID, Food 2 ID, Food 3 ID, etc.) set to W, then W is written to the food ingested field of a row of the user profile database 1900 whose user field is set to X.

In step 1202, personal information is received by the user profile subsystem 405. This information might, for example, have been entered by the user into a form, or the information might have been entered by the user in a free-form manner. This information might also have been obtained, without input by the user, from another source such as, for example, a third party database. In specific examples, the user indicates that they have an intolerance to gluten, a desire to not consume preservatives or follow a low-sodium diet, and/or a desire to ingest adequate vitamins without taking supplements. For example, with reference to FIG. 19, each item of personal information is entered into the user profile database 1900 as a row with a subject field and a preference field, with the subject field taking on values like, for example, "gluten-intolerance" or "preservatives" or "low-sodium-diet" or "vitamin-supplements" and the preferences field taking on values like, for example, "moderate" or "avoid" or "yes" or "none", respectively, and where each such row also has a date field and a user field.

In step 1206, user feedback is received by the user profile subsystem. For example, this feedback might be entered by the user periodically over time in response to queries like "how is your digestion?" or "what is your mood?" or "have you had headaches?" or "are you feeling dizzy?" or "how hungry are you?" or "do you have any cravings?" or "how is your libido?" For example, with reference to FIG. 19, each item of user feedback is entered into the user profile database 1900 as a row, with a query field set to values like, for example, "digestion", "mood", "headaches", "dizziness", "hunger" etc. and a response field set to values like, for example, integers between −10 and 10, where −10 might indicate a most negative response and 10 a most positive response, and where each such row also has a date field and a user field.

In step 1203, user interaction data is received. This includes, for example, records related to which information is viewed by the user, and how the user interacts with, or provides input to, the personal computing device; for example, where the user clicks on a webpage. For example, the fact that user X on date Y viewed information on food Z (for example, vitamin D) might be recorded to the user profile database.

In step 1204, passive personal log data is received by the user profile subsystem. In some embodiments, the user's passive log device 303 (which could be the spectrometer 101 itself, or a similar device, as discussed herein) records at least some of the user's personal log data. This data is recorded passively, in the sense that it is recorded without necessarily the need for conscious action by the user. In some embodiments, some action by the user might be required to facilitate the recording of passive personal log data. For example, the user might need to point, or move, or adjust the passive log device 303, or press a button on the passive log device 303, or even spit or urinate etc., to facilitate the collection of the personal log data. For example, this personal log data might contain records of the user's pulse, blood pressure, blood oxygen levels, or blood sugar level. For example, this data might be evaluated and recorded once per minute.

In step 1207, the data fetched from the food database at step 1201, the personal information received at step 1202, the user feedback received at step 1206, the user interaction data received at step 1203, and the passive personal log data received at step 1204, are all written to the user profile database 1900.

Ranking

Figure 13:
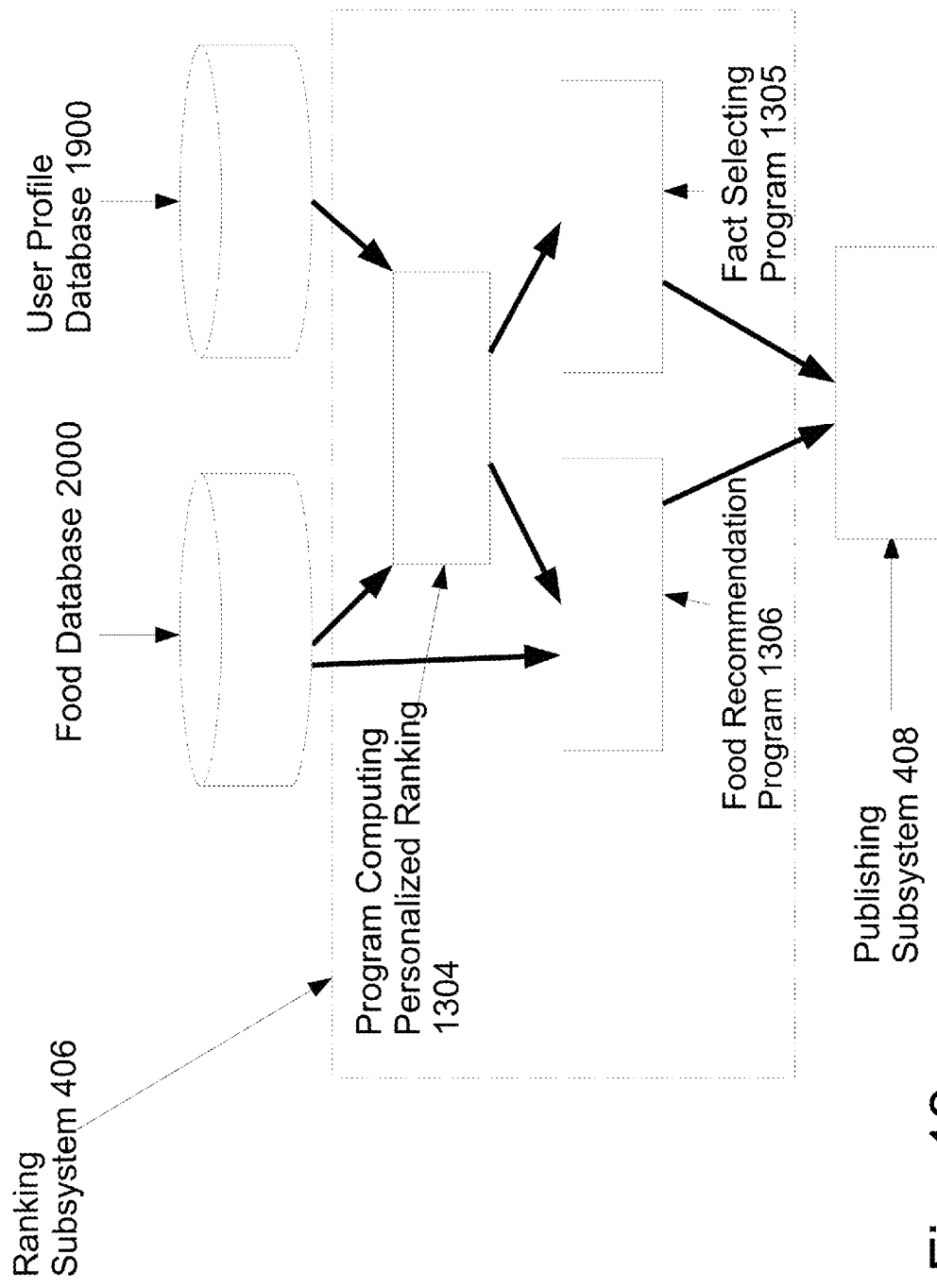
FIG. 13 shows a block diagram of the ranking subsystem of a server system, including means for receiving data for the food database and user profile database, and computing personalized facts and recommendations about food.

FIG. 13 shows a block diagram of the ranking subsystem of a server system, including means for receiving data for the food database and user profile database, and computing personalized facts and recommendations about food.

FIG. 13 depicts a ranking subsystem 406, which includes a personalized ranking program 1304 which can compute personalized rankings of foods and facts about foods, a food recommendation program 1306 which can choose foods to be recommended to users, and a fact selection program 1305 which can select facts suitable for presentation to users. The ranking subsystem 406 is responsive to output from the spectrum analysis subsystem 404. The ranking subsystem 406 is connected to the publishing subsystem 408, and the publishing subsystem 408 is responsive to output by the ranking subsystem 406. In some embodiments, the ranking subsystem 406 is responsive to changes in the food database 2000 and/or changes in the user profile database 1900.

The program 1304 can compute personalized rankings of foods and facts about foods on input of a particular food ID. In some embodiments: (a) the ranking subsystem is responsive to the spectrum analysis subsystem writing a food ID field in a row in the database of spectra 2200, and this so-written food ID can be the input A to the program 1304; (b) the program 1304 can query the food database 2000, and receive the row R of the food database 2000 whose food ID field is A, where the row R contains multiple subfood IDs B(1), B(2), . . . ; (c) the program 1304 can query the food database 2000, and receive in response, the rows of the food database 2000 whose food IDs are among the subfood IDs B(1), B(2), . . . ; (d) the program 1304 can iterate this process until, for example, data about those subfoods, whose field in the food database 2000 is yes, is obtained; (e) the program 1304 can calculate, for each public subfood ID, in response to the concentration X of that subfood within the sample whose food ID is A, and the middle level Y recorded in the food database 2000, a relative significance indicator S, where the quantities X and Y are numbers and this calculation of S performed by the program 1304 by dividing X by Y, and taking the natural logarithm of the result; and (f) the result can also be responsive to recorded levels of confidence in X and Y.

The program 1304 can read from, and write to, the user profile database 1900. In some embodiments, the program 1304 can: (a) receive data associated with the user ID of the user to whom the output of the ranking subsystem 406 is to be presented by the publishing subsystem 408, including personal info, user feedback, user interaction data, passive personal log data, and food consumption data; and (b) write data associated with the user ID of the user to the user profile database 1900, including a personal importance level to the user of any public food or subfood.

The program 1304 can also take the aforementioned logarithm and modify it in response to data obtained from the user profile database 1900, such as, for example, the personal importance level of foods. For example, the program 1304 can: (a) add each such personal importance level to each aforesaid logarithm, and thereby obtain a personal level for that subfood as it occurs in the sample; and (b) order all these personal levels for the subfoods in a sample; and (c) output a personalized ranked list of the subfoods in a sample, which we call facts.

For example, for each public subfood and each user, the program 1304 can compute a personal importance level of that subfood, indicating the level of personal importance of that subfood to that user, and the program 1304 can write that personal importance level to the user profile database 1900. This computation of the personal importance level of a food or subfood for a user can be responsive to data in the user profile database 1900 about that user, including personal info, user feedback, user interaction data, passive personal log data, and food consumption data. For example, the personal importance level can be responsive to a record of the user's expressed interest in following a low sodium diet, or a record of the user's expressed interest in a certain kind of food additive, or a record of the user viewing information about a certain ingredient, or a record of the kinds of foods the user is apparently most interested in scanning, or to data indicating a medical condition of the user, or, with reference to the food database, to data indicating the beneficial or harmful properties of a food to a one or more medical conditions. For example, as a result of this, the personalized ranked list can be produced in response to: (a) the feedback the user provides from time to time on his/her health or mood; (b) the user's medical information over time e.g. pulse rate, blood pressure, blood glucose level etc.; and/or (c) or the user's stated medical issues such as gluten intolerance, diabetes, high blood pressure etc.

The ranking of a fact can be responsive to the estimate of the quantity detected, and/or the confidence in that estimate. For example, the presence of a small amount of maltodextrin might be ranked below (i.e. less important than) the presence of a large amount of high fructose corn syrup. Or the presence of soybean oil, and thus the unconfirmed presence of trans fats, might be ranked below the stated presence of sodium benzoate. The ranking of a fact can also be responsive to the recent scans associated with that user ID, which can be interpreted to reflect the historical consumption of the user. For example, if a customer has already consumed too much sugar in the past 24 hours, then the ranking of a fact about the high sugar content of a food might be raised; and, if a user has already consumed enough vitamin C in the past week, then the ranking of a fact about the vitamin C content of a food might be lowered. Facts that together have more severity than each fact by itself can be raised in ranking. For example, if a food contains sodium benzoate and another food scanned a few minutes earlier contains vitamin C, then the ranking of the fact that the second food contains sodium benzoate can be raised so as to better warn the user of the possible interaction between the sodium benzoate and the vitamin C, and the consequent production of benzene, which is carcinogenic. For another example, if the user profile database indicates that the user smokes tobacco, then the ranking of a fact that the user has scanned a food with a large amount of vitamin A can be raised.

In embodiments in which the system is integrated with, or used in conjunction with, a device that can estimate the volume of a sample, the facts about samples mentioned herein can be converted from relative or per serving estimates to absolute estimates. In some such embodiments, the system tracks the user's overall consumption of additives, processed sugars, starches, or proteins, vitamins, minerals, fats, proteins, carbohydrates, sugars, salts, calories, allergens, pesticides, metals, carcinogens, other toxins, antioxidants, or phytonutrients, etc. and can compare such consumption with desired or recommended (e.g. by FDA) levels. In some such embodiments, the system can assess the user's adherence to a specific diet such as Atkins diet, South Beach diet, low-sodium diet, or vegan diet, and help the user adhere to the diet, or present to the user how well they have adhered to the diet. In some such embodiments, in conjunction with a method of estimating calories burned, the system can compute and present to the user the expected change in their weight. In some such embodiments, the system could compute and present to the user whether their food intake has provided an adequate amino acid profile.

In some embodiments, the personalized ranking program 1304 can calculate a personal rank for the food whose food ID is A in response to the personal levels for all its subfoods and in response to the good-bad field for those subfoods in the food database 2000. In some embodiments, each good-bad field is a positive or negative number, and the program 1304 can: (a) multiply, for each subfood, the computed personal level and the number in the good-bad field; (b) add up the results; and (c) compute the rank of the food to be the index of that food in a list of all foods listed according to these sums.

In alternate embodiments, some or all of the aforementioned subfoods is associated with a scale that maps concentrations of that subfood within a sample to a positive or negative integer in such a way that a positive integer reflects a desirable concentration, and a negative integer reflects an undesirable concentration, and the magnitude of the integer reflects the severity of the desirability or undesirability. In some such embodiments, the rank of the food is responsive in part to the sum of the aforementioned integers for each such subfood.

In some embodiments, the rank of a food is responsive also to the volume of the sample. For an example, data on calories per serving could be converted to total calories in the sample or could be normalized to a common serving size before comparing the ranks of foods. In another example, the glycemic index of a food can be converted to glycemic load before calculating the rank of the food.

In some embodiments, the rank of a food is responsive also to: (a) the user's reported like or dislike of that food or similar foods; and/or (b) the capacity of that food to satisfy the appetite of that user as reported by that user for that food or similar foods and/or as calculated from the food's ingredients, or some combination thereof. For example, celery might be ranked higher than iceberg lettuce for a user even when iceberg lettuce is otherwise ranked slightly higher, if the user reports that they like celery but strongly dislike iceberg lettuce.

Figure 25:
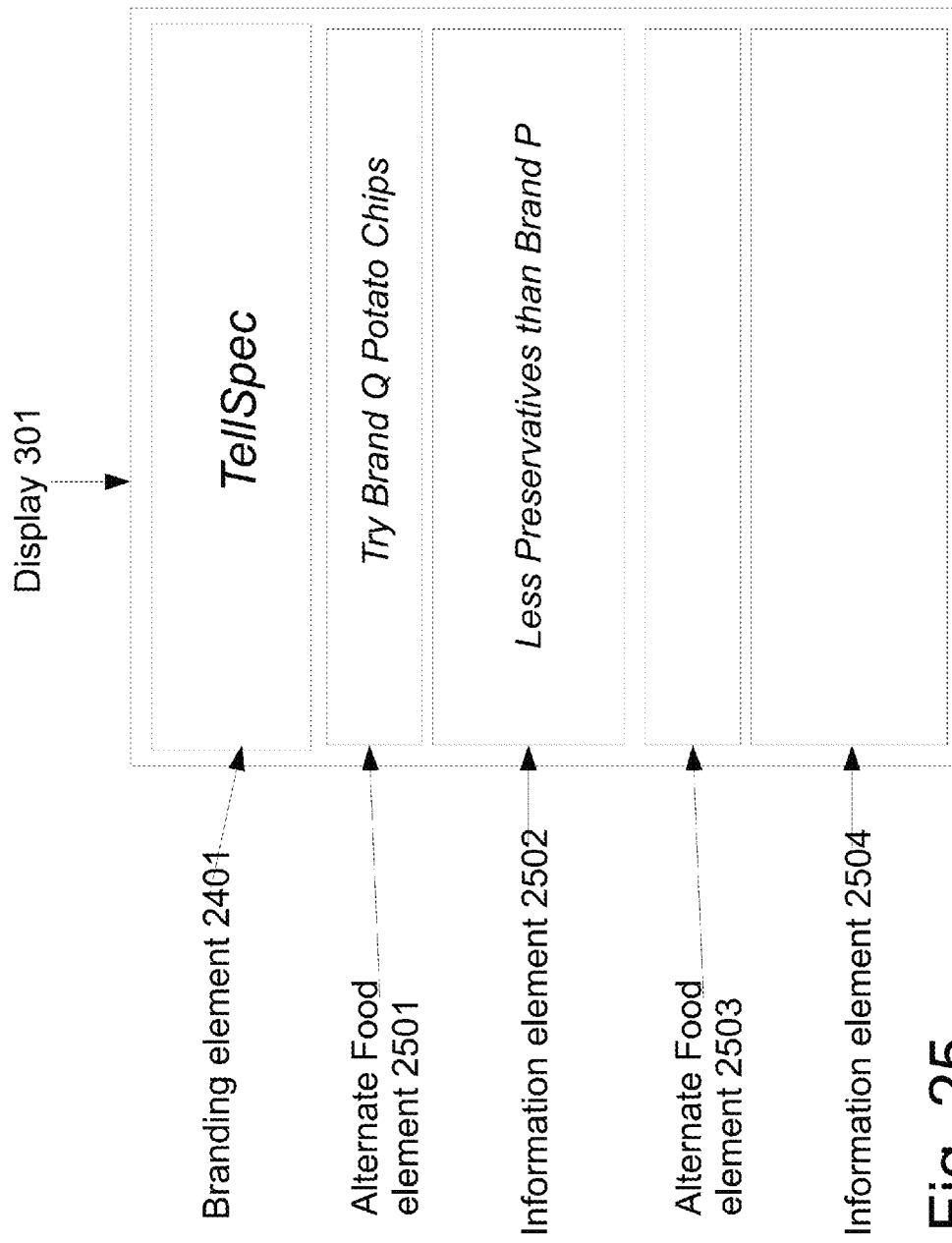
FIG. 25 illustrates a user interface that shows: suggestions of alternate foods, with higher personalized rankings; reasons for these suggestion; and built-in hyperlinks to information about these alternate foods.

The presentation of information about a food A that is depicted in FIG. 25 includes a suggestion of an alternate food B that is similar to A. In some embodiments, any suggested alternate food B must have a higher personalized ranking for the user to whom the information is presented than the food A, about which information is being viewed. For example, in FIG. 25, the user has just scanned Brand P Potato Chips, and the presented information is suggesting Brand Q Potato Chips as an alternative. In another example, the user is presented with information indicating whether or not the food most recently scanned by that user is better, in that user's personalized ranking of foods, than a similar food that the same user had scanned a few minutes earlier, or the previous week. In another example, a user scans two products in a grocery store, and the user is then be presented with information identifying the better product, according to that user's personalized ranking of foods. In another example, a user scans a dish in a restaurant, and the user is then presented with information recommending a similar but better dish, under that user's personalized ranking of dishes, at the same restaurant, or another nearby restaurant, or a recipe for a similar but better dish together with a suggestion of a nearby food store which sells the appropriate ingredients. In some embodiments, a suggestion presented to the user for a similar but better food or dish is accompanied by an incentive, such as a coupon or special offer.

In some embodiments, the presentation of information about a food includes a suggestion of a food complementary, rather than similar, to the one about which information is being viewed, or complementary to the foods recently ingested. In this context, complementary means that together the (nutrients in the) foods are balanced better, or work together better. In one example, if folic acid contributes to the protective nature of fruits and vegetables against large-bowel cancer, then the system can present a suggestion for a food that contains a good amount of folic acid to someone who has recently consumed lots of fruit and vegetables.

In some embodiments, the system combines rankings of food or meals to produce overall rankings of cafes, restaurants, food stores, personal diets, or types of food, and presents information about these to users. In some embodiments, the rankings of foods or meals or the aforementioned overall rankings are compared over time, and the system presents the user with information about changes or improvements in these rankings over time. For example, the system can present the user from time to time with an overall quality index for the food the user ingests and a report on changes in that index over time. In another example, the system assesses, and presents the user with information about, the single most beneficial yet incremental change the user can make to his/her diet. In another example, the system presents the user at dinner preparation time with an assessment of the day's food intake and suggest areas that need attention. In another example, the system informs the user that they have consumed too much sugar, too many calories, not enough protein, and not enough vitamin E, and recommends a meal that addresses these issues, while still satisfying the user.

These rankings of food enable a method or a method of doing business in which foods, or other products, are ranked by some algorithm, and advertisements are accepted from potential advertisers only for suggesting products A as alternatives to other products B, where the suggested products A are ranked higher by the algorithm than the other products B. In some embodiments, these rankings are personalized, and so advertisements of a product C as an alternative to another product D are accepted for some users but not others.

In some embodiments in which the system 100 contains, is integrated with, or is used in conjunction with, a device that can estimate the volume of a sample, the system ranks foods at least partly in response to their volume, their serving size, and/or their effect on satiety or blood sugar level. In one example, the system presents a suggestion to a user, who is considering consuming a particular volume or weight or serving size X of a food A, of a volume or weight or serving size Y of an alternate food B, which has lower caloric content than the serving X of A, but which provides similar satiety to the user, measured for example by effect on blood sugar.

In some embodiments, when the system 100 presents to the user information responsive to the rank of a food or meal, summary information about the food could also be presented. For example, a numerical, visual, or textual description, assessment, or score, of how natural, processed, healthy, nutritious, or appetite-satisfying, a food or meal is, or the degree to which the food or meal meets the user's dietary or medical needs or desires could be presented.

In some embodiments, the ranking of facts or foods or meals is responsive to a diet that the user has indicated they wish to follow, or to the knowledge base, advice, and/or dietary guidelines set out or disseminated by institutions like United States Department of Agriculture, Centers for Disease Control and Prevention, the US Food and Drug Administration, or the World Health Organization, or any other international organization or governmental body, as it relates to food safety programs, product-specific information, food allergens, food borne illness, and food contaminants.

Figure 14:
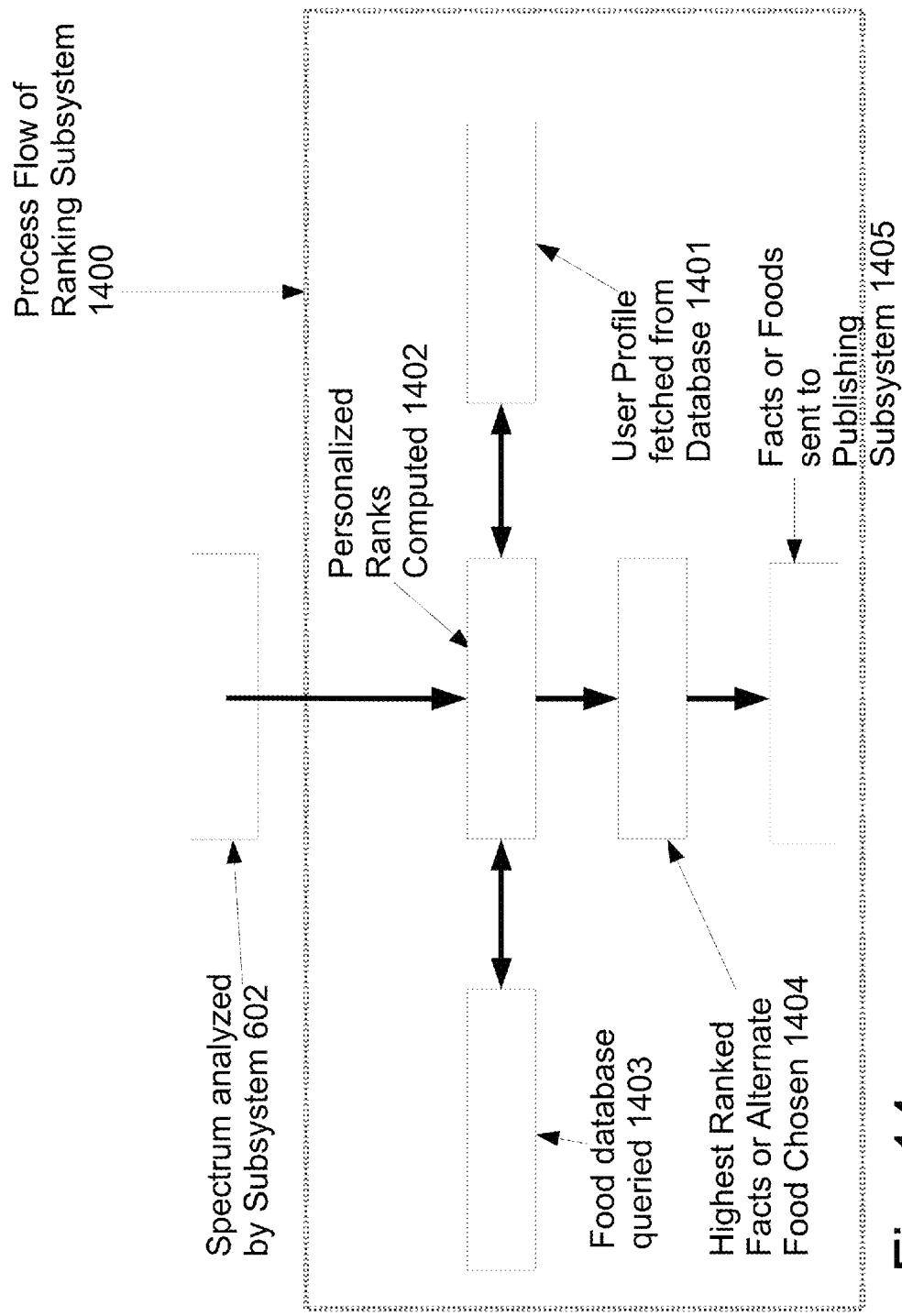
FIG. 14 depicts a process flow 1400 of a method of operation of the ranking subsystem of the server system when ranking facts and selecting facts for presentation, or when ranking foods and selecting alternate or complementary foods to suggest, with reference to FIG. 13.

FIG. 14 depicts a process flow 1400 of a method of operation of the ranking subsystem of the server system when ranking facts and selecting facts for presentation, or when ranking foods and selecting alternate or complementary foods to suggest, with reference to FIG. 13.

At step 602, a input spectrum has been analyzed, and the spectrum analysis subsystem has, for example, written a food ID A in the food ID field in a row in the database of spectra 2200, and this so-written food ID A is input to the ranking subsystem.

In step 1403, the program 1304 queries the food database 2000, and receives the row R of the food database 2000 in which the food ID field is the A from step 602. The program 1304 queries the food database 2000, and receives the rows of the food database 2000 whose food IDs are among B(1), B(2), . . . where B(1), B(2), . . . are the subfood IDs that row R contains. The program 1304 recursively iterates this process for all such food IDs and subfood IDs. The aforementioned recursion terminates for any public subfood, and recursion does not extend to the subfood IDs of a public subfood.

In step 1401, the program 1304 queries the user profile database 1900, and receives data associated with the user whose user ID is written in the row of the database of spectra 2200 corresponding to the input spectrum of step 602.

In step 1402, the program 1304 calculates, for each public subfood ID, in response to the concentration of that subfood within the sample whose food ID is A, and the middle level recorded in the food database 2000, an indicator of relative significance of that subfood with respect to the sample, whose spectrum is the input spectrum of step 602. The aforesaid concentration and middle level are numbers and this calculation is done by dividing the first by the second, and taking the natural logarithm of the result. The program 1304 then takes that logarithm and modifies it in response to the data obtained from the user profile database 1900 in step 1402. For each recursively obtained public subfood of the food whose food ID is A, the program 1304 computes personal importance levels, which indicate a level of personal importance of each subfood to the user, adds each such personal importance level to each corresponding aforesaid logarithm of each subfood, and thereby obtains a personal level for each subfood.

The program 1304 also calculates a personal rank for the food whose food ID is A in response to the personal levels for all the recursive subfoods and in response to the good-bad field for those recursive subfoods in the food database 2000. Each good-bad field is a positive or negative number and program 1304 multiplies, for each recursive subfood, the computed personal level and the number in the good-bad field, and adds up the results to obtain a sum. The rank of the food whose food ID is A is then computed as the index or placement of that food in a list of all foods listed according to these sums.

In step 1404, the program 1304: (a) orders all these personal levels, and creates a ranked list of the subfoods, which we call facts; (b) calculates the personal rank of the food itself; and (c) queries the food database for alternate foods B to the food whose food ID is A such that the rank of B is higher than the rank of A. This query can be performed with reference to fields in the food database that indicate a preference for certain foods according to some business rules.

In step 1405, the program 1304 outputs: (a) the ranked list of subfoods or facts; (b) one or more suggested alternate foods B; and possibly (c) some information indicating some reasons why B is ranked higher than A.

The ordering of the ranked list in step 1404 can be responsive to a desire to present a balanced selection of facts in whatever lists are to be presented to, or viewed by, the user. For one example, the ordering can be responsive to a desire that the ten top facts be somewhat balanced between positive and negative facts (e.g. at least 3 positive and at least 3 negative), and be somewhat balanced in terms of the different types of facts (e.g. no more than 2 facts about toxins, and no more than 3 facts about vitamins). In some embodiments, this can be done probabilistically, so that, if the first three facts are negative facts, then when selecting the fourth fact, the fact selection program 1305 might effectively raise the ranking of the highest-ranked positive facts so that the fourth fact is more likely to be positive. Similarly, in some embodiments, if the first two facts are about toxins, then the fact selection program 1305 might effectively lower the ranking of the next highest-ranked facts about toxins so that the third fact is less likely to be about toxins.

Link Detection

Figure 15:
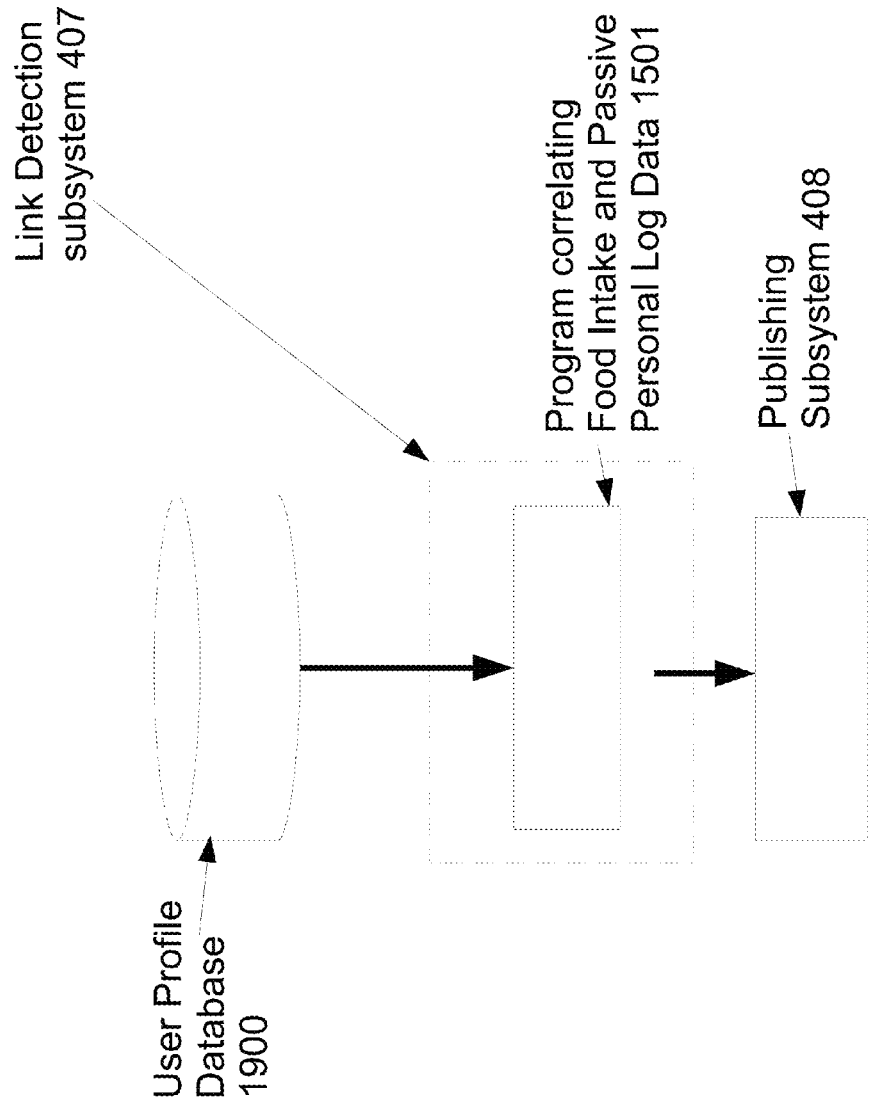
FIG. 15 shows a block diagram of the link detection subsystem of a server system, including means for receiving data from the food and user profile databases, correlating food intake and personal log data, and detecting possible links between them.

FIG. 15 shows a block diagram of the link detection subsystem of a server system, including means for receiving data from the food and user profile databases, correlating food intake and personal log data, and detecting possible links between them.

The link detection subsystem 407 includes a program 1501 that can correlate food consumption data for a user over time, passive personal log data 1107 related to that user gathered over time, and possibly user feedback, user interaction data, and personal information related to that user, or other users, gathered over time. The food consumption data, passive personal log data, user feedback, user interaction data, and personal data related to that user, or to other users, are stored in a user profile database 1900. The link detection subsystem 407 is responsive to changes in the user profile database 1900 and is connected to the publishing subsystem 408. The publishing subsystem 408 is responsive to output from the link detection subsystem 407.

The program 1501 can take food consumption data for a user over time and passive personal log data 1107 over time, and/or possibly user feedback, user interaction data, and personal information related to that user over time, and compute a correlation factor. For example: the program 1501 can: (a) compute, for each public food, in response to the food consumption data for that user over time, an array of non-negative numbers indexed by time periods, which indicate the intake by the user of that public food in each time period; (b) take passive personal log data 1107 over time, or possibly user feedback, user interaction data, and personal information related to that user over time, and compute arrays of numbers indexed by time periods, which indicate states of that user, including well-being, blood pressure, intestinal comfort, etc.; (c) compute several different such arrays, each indicating various different facets of the state of the user; (d) translate all these arrays, in the mathematical sense, so that the average value is zero, and normalize them so that the average absolute value (magnitude) of the entries is one; (e) compute correlation factors by multiplying, for each time period, the entry in the array indicating intake of a public food with the entry in the array indicating a state of the user, both corresponding to that time period, and then adding up these products for all time periods; (f) compare correlation factors with preset values and output those which are greater than one preset value or less than a second preset value; and (g) rank the correlation factors and output the greatest and/or smallest of these.

For example, the user feedback 1105 can include manually entered feedback that the customer provides from time to time on his/her health or mood and the passive personal log data 1107 can include the customer's medical information over time such as pulse rate, blood pressure, or blood glucose level, and so, if a statistical correlation is found between the user's consumption of foods containing gluten and lower feelings of well-being reported by the user, then the system can present information to the user indicating that the user may be gluten intolerant, and, if a statistical correlation is found between the user's consumption of foods containing sodium and his/her higher blood pressure, then the system can present information to the user indicating that he/she might consider reducing salt intake or increasing potassium intake. In another example, a user may repeatedly experience an allergic reaction but be unable to determine the food or ingredient, or combination thereof, that is causing the reaction, but the link detection subsystem may be able to detect a particular food or ingredient, or combination thereof, that is likely or possibly causing this reaction.

In some embodiments, correlation of passive personal log data of a user over time and food consumption data for that user over time provide tell-tale fingerprints of allergies, food intolerances, or other disorders or diseases. In some such embodiments, such correlations also involve user feedback, user interaction data, and personal information related to that user over time. For one example, in the special case in which the foods are medications, pharmaceuticals, prescription drugs, non-prescription drugs or health food supplements, then the link detection subsystem could provide information about allergies to, or intolerances to, or effectiveness of, or side effects of, those medications etc or combinations of them. For another example, correlation between food and ingredient consumption and passive personal log data or user feedback data across large populations of users may be able to detect relationships between toxins and other chemicals, and illnesses or medical disorders.

In some embodiments, the passive personal log data and food consumption data of a population of users over time, and possibly also the user feedback, user interaction data, and personal information of those users over time, could be correlated to obtain information about the relationship between food (and medicine) intake and personal health across a population. For example, such populations could be defined using personal information received, and could include males between 25 and 39, or female smokers, or unemployed males in Ohio, or females with stressful occupations who commute at least one hour per day. As other examples: (a) correlation with user interaction data could be used to, for example, determine that 85% of those who acted on, and followed, five suggestions for better food within the last year, experienced an improvement in their blood pressure; and (b) correlation with data received by a company offering coupon incentives to try suggestions of better food could be used to determine that 90% of those who used at least three coupons in the past month, reported higher feelings of well-being.

In some embodiments, the link detection subsystem can detect the similarity of the passive personal log data, and possibly also the food consumption data, user feedback, user interaction data, and personal information over time, of two users, and the similarity of those two users could then be responsive to that detected similarity of that passive personal log data, and possibly also that food consumption data, user feedback, user interaction data, and personal information over time. For example, two users that have similar interests in food and/or similar concerns or interests in toxins or allergens may be considered similar in one or more steps, processes, etc. where information related to a user B more similar to a user A is treated differently from information related to a user B less similar to a user A.

In some embodiments, the link detection subsystem 407: (a) correlates food consumption data for a user X over time, passive personal log data related to that user X gathered over time, and possibly user feedback, user interaction data, and personal information related to that user X gathered over time, and with reference to food consumption data for other users over time, passive personal log data related to other users gathered over time, and possibly user feedback, user interaction data, and personal information related to other users gathered over time; and (b) in response to said correlations, estimates or determines the expected future medical and/or health conditions of that user X, for example, including estimated expected net present value of medical costs and life expectancy. In these embodiments, the estimated expected net present value of medical costs and life expectancy could be used to assess the price of life insurance or medical insurance. For example, a user can opt to share these estimates with a seller of life insurance in the case where this results in a reduction in that cost. In some such embodiments, the user could be presented with information related to how their actions or choices could raise or lower their insurance costs and/or the user could receive a rebate in insurance costs, for example, for completing portfolios of accomplishments.

Figure 16:
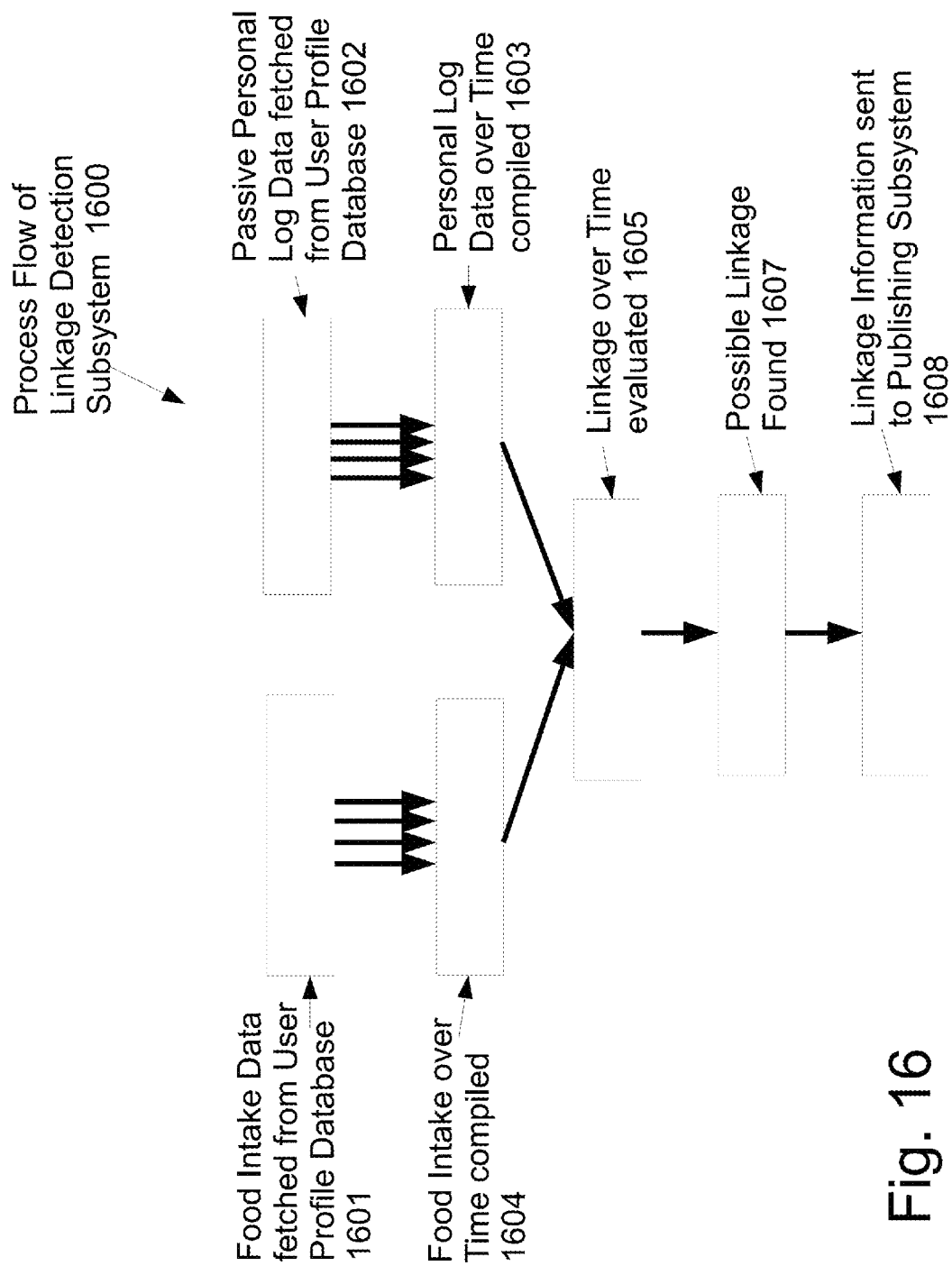
FIG. 16 depicts a process flow 1600 of a method of operation of the link detection subsystem of the server system with reference to FIG. 15.

FIG. 16 depicts a process flow 1600 of a method of operation of the link detection subsystem of the server system with reference to FIG. 15.

In step 1601, the program 1501 fetches food consumption data related to a user from the user profile database 1900, with reference to the food database 2000, and possibly in response to a change in the user profile database 1900.

In step 1604, the program 1501 computes, in response to the aforementioned food consumption data related to a user, for each public food, an array of non-negative numbers indexed by time periods, which indicates the intake by the user of that public food in each time period.

In step 1602, the program 1501 fetches passive personal log data related to that user, and possibly user feedback, user interaction data, and personal information related to that user, from the user profile database 1900.

In step 1603, the program 1501 computes, in response to the aforementioned passive personal log data related to that user, and possibly user feedback, user interaction data, and personal information related to that user, arrays of numbers indexed by time periods, which indicate the state of that user.

In various embodiments, the program 1501 computes various numbers of such arrays, which indicate various facets of the state of the user.

In step 1605, the program 1501 uses the arrays related to food consumption by a user and the arrays related to passive personal log data related to that user, and possibly user feedback, user interaction data, and personal information related to that user, to compute, for each such array, correlation factors. These correlation factors are computed by multiplying, for each time period, the entry in an array indicating consumption level of a public food with the entry in an array indicating state of the user, both entries corresponding to that same time period, and then adding up these products over all time periods.

In step 1607, the program 1501 compares the computed correlation factors with preset values and outputs those which are greater than a first preset value or less than a second preset value and/or ranks the correlation factors and outputs the greatest and smallest of these.

In step 1608, the link detection subsystem 407 sends the linkage information computed in step 1607 to the publishing subsystem 408.

Publishing

Figure 17:
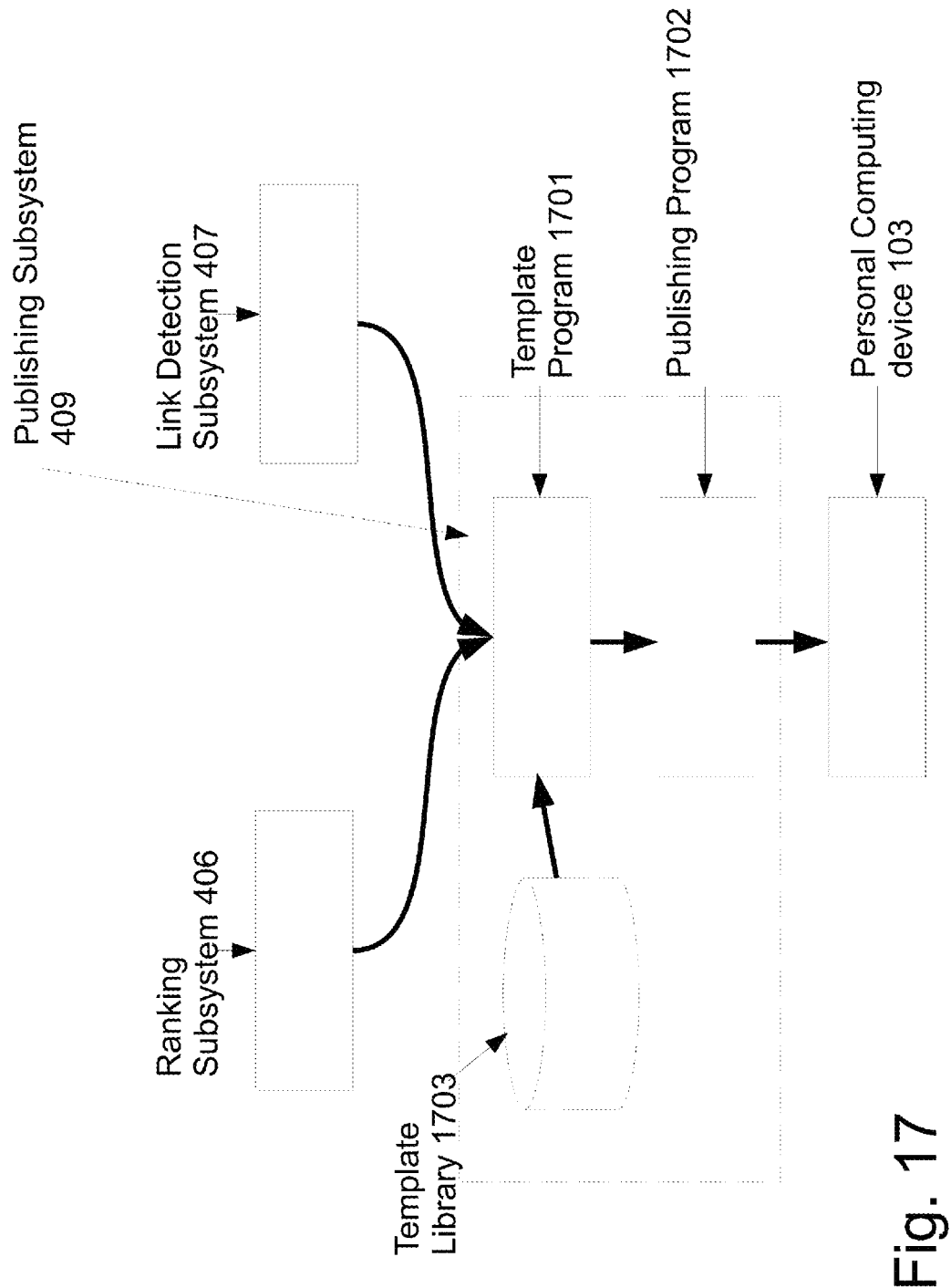
FIG. 17 shows a block diagram of the publishing subsystem of a server system, including means for receiving personalized data and for using templates to create personalized information suitable for display on a personal computing device.

FIG. 17 shows a block diagram of the publishing subsystem of a server system, including means for receiving personalized data and for using templates to create personalized information suitable for display on a personal computing device.

The publishing subsystem 408 includes a template library 1703, template program 1701, editing and publishing program 1702, connections to the ranking subsystem 406 and the link detection subsystem 407, and a means of transmitting personalized information suitable for display to a personal computing device 103. The publishing subsystem 408 is responsive to output by the ranking subsystem 406 or the link detection subsystem 407, and to communications received from the personal computing device 103. Within the publishing subsystem 408, the editing and publishing program 1702 is responsive to output of the template program 1701. The publishing subsystem 408 is attached to the personal computing device 103 by an internet or other connection.

The personalized information displayed on the personal computing device can be presented to the user through any of text, images, audio, or video or other means, or any combination of these. For example, the presentation can be in the form of a text message, a webpage, a voice message, a sequence of photographs or drawings, an animated video, another kind of video, and so forth.

This disclosure describes many possible embodiments and examples without details on the presentation to the user of information in these embodiments or examples. In these embodiments and examples, or variations thereof, the information can be output to the publishing subsystem 408 and, with or without the use of templates not described here, but obvious to those familiar with the art, that information can be displayed on a personal computing device 103.

Figure 18:
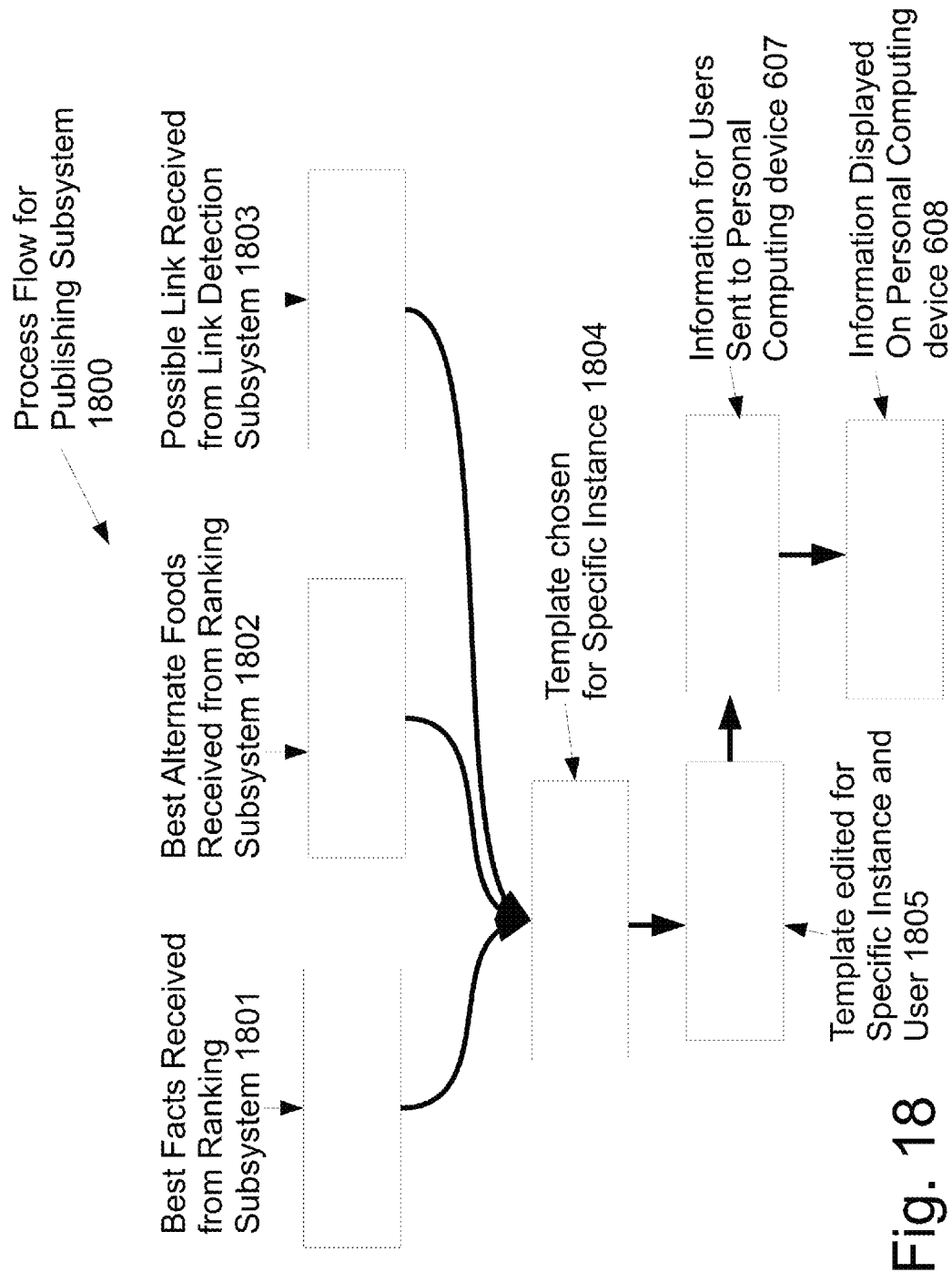
FIG. 18 depicts a process flow 1800 of a method of operation of the publishing subsystem of the server system with reference to FIG. 17.

FIG. 18 depicts a process flow 1800 of a method of operation of the publishing subsystem of the server system with reference to FIG. 17.

In step 1801, the template program 1701 receives a ranked list of facts personalized for a user and related to a food, for example being at that time considered by a user, from the ranking subsystem 406.

In step 1802, the template program 1701 receives a list of possible foods that are alternate or complementary to a food, for example being at that time considered by a user, from the ranking subsystem 406.

In step 1803, the template program 1701 receives information about a possible link between, for example, a user's consumption of foods and ingredients, and that user's passive personal log data or user feedback data, from the link detection subsystem 407.

In step 1804, the template program 1701 parses and edits the specific information received in steps 1801, 1802 or 1803, determines the appropriate template for presenting that information, fetches that appropriate template from the template library 1703, and outputs the parsed and edited specific information and the template to the publishing program 1702.

In step 1805, the publishing program 1702 receives, as input, the template and parsed and edited information output by the template program 1701, which was output in step 1804, adds the parsed and edited information to the template, and prepares a page of information personalized for the user containing the parsed and edited information, possibly further edited, within the template, also possibly edited.

In step 607, also depicted in FIG. 6, the server 102 transmits the information prepared at step 1805, to a user's personal computing device 103.

In step 608, also depicted in FIG. 6, the personal computing device 103 receives the information sent in step 607, and displays it to the user 104.

Figure 19:
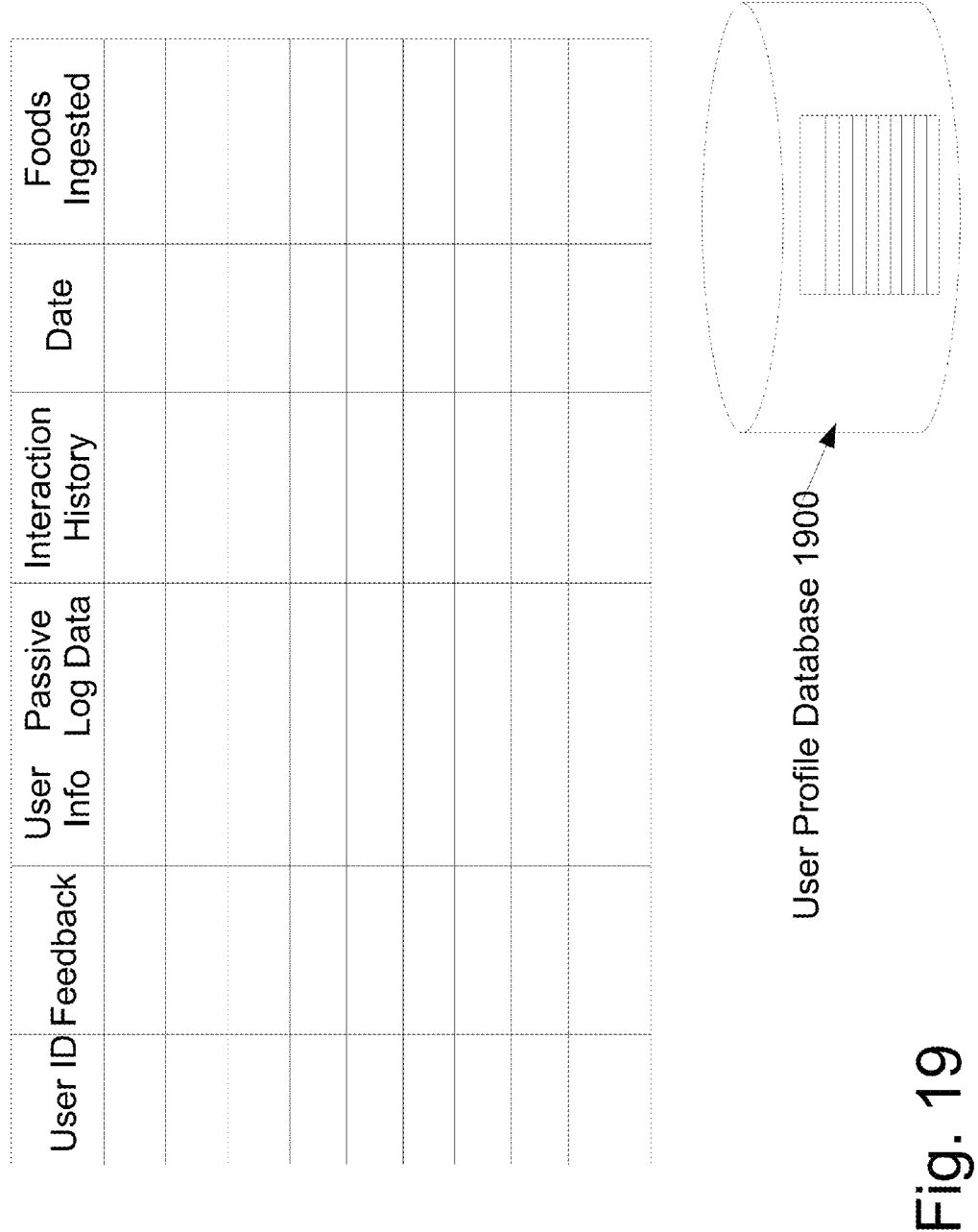
FIG. 19 illustrates a database of user profiles, including user IDs, user feedback, user information, passive log data, interaction history, date and time, and food ingestion history.

FIG. 19 illustrates a database of user profiles, including user IDs, user feedback, user information, passive log data, interaction history, date and time, and food ingestion history.

The user profile database 1900 can include information about users. In the context of the invention, there is no particular requirement that the user profile database 1900 is limited to information about users. For one example, the user profile database 1900 could include information about groups of users and about persons that might consume some of the foods being scanned, but who are not necessarily users, or groups of such persons.

In FIG. 19, the user profile database 1900 includes one row for each kind of data received at a particular date and time, a particular user ID, and of a particular kind. In the example depicted in FIG. 19, a typical row can contain data in the 1st and 6th columns, but may contain non-default data in none, one, or more, of the 2nd, 3rd, 4th, 5th, and 7th columns, depending on the kind of information.

In some embodiments, the user profile database 1900 contains genetic information about the user. An example of such information would be the genetic polymorphisms of the user. For example, such information can be then used to determine that certain nutrients are recommended in greater or lesser quantities to the user, or recommended to be ingested in different forms.

In some embodiments, the user profile database 1900 includes real-time user location, body mass index (BMI) history, medical history, risk factors associated with various diseases and medical conditions such as obesity and diabetes, demographic information, and/or information about relevant, or geographically near, epidemics.

In some embodiments, the user profile database 1900 and the food database 2000 could contain, or can query, a database that contains information about the food available to the user, either in their home refrigerator, cupboards, pantry, freezer etc., or food on order by the user and expected to be delivered, or food available at a nearby store, at various times of the day. In some such embodiments, the suggestions of alternate foods described herein could be tailored to those on which the user can act most effectively.

Figure 20:
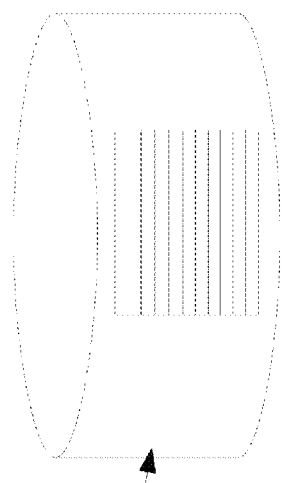
FIG. 20 illustrates a database of foods, including restaurant offerings, including fields for main food ID, parent food ID, subfood IDs, subfood percentages, middle levels, public indicator, good-bad indicator, a list of facts, and a list of alternates.

FIG. 20 illustrates a database of foods, including restaurant offerings, including fields for main food ID, parent food ID, subfood IDs, subfood percentages, middle levels, public indicator, good-bad indicator, a list of facts, and a list of alternates.

The food database 2000 can include information about foods or other samples whether or not they have been scanned by the spectroscope 101. The food database can include rows for foods at varying levels of generality. For example, a row can be written in the food database for each scan of each sample. If the same food is scanned again a few minutes later, another row can be written in the food database. Any time that a scan of a sample is recorded, and the sample is identified as a sample of a SKU of food, then a row R can be written to the food database for that SKU, if not already present. The food ID for the row R may be the parent food ID for the rows for particular scans of samples of that food. Rows can also be written to the food database, when not already present, for generic unbranded types of food, such as "Corn Flakes" and for general categories of food such as "Breakfast Cereals".

The food database 2000 can also include information about food ingredients, such as, for example, sugars, proteins, vitamins, and additives. The food database can include rows for such ingredients at various levels of generality. For example, when an ingredient is detected directly or indirectly in a sample, a row for that ingredient in that sample can be written in the food database. If the sample is scanned again a few minutes later, and the same ingredient is detected in that sample from that scan, then another row can be written in the food database. Any time that an ingredient is known to be present in a SKU of food, a row R can be written to the food database for that ingredient in that SKU. The food ID for this row R may be the parent food ID for the rows for the same ingredient in particular scans of samples of that food. Rows can also be written to the food database, when not already present, for generic ingredients, such as "Preservatives" and for general categories of food such as "Additives".

The ingredients of a SKU of food recorded in the food database 2000, or the amounts or percentages of each ingredient in a SKU of food recorded there, need not agree with the ingredients or their amounts or percentages listed on the label provided with that SKU of food, since regulations sometimes allow food companies to not list certain additives or nutrients, or to list them in ways that mislead consumers. For example, although some regulations allow foods with less than 0.5 g of trans fats per serving to declare 0 trans fats, more accurate information about trans fats can be recorded in the food database 2000.

The information about a food recorded in the food database 2000 can include information derived, aggregated, processed, or computed from information about the ingredients of that food or other information about that food. For example, such information can include calories or glycemic load per serving.

In some embodiments, information about foods can relate to inaccuracies or omissions in the food label. For example, such information can include facts or suspicions related to: (a) inaccurately labeled fish species or varieties; (b) horse meat inaccurately labeled as beef; (c) olive oil inaccurately labeled as cold-pressed; or (d) a recall of food by the producer, because of contamination with salmonella, listeria or other microbes.

In the context of the invention, there is no particular requirement that the food database 2000 be limited to information about foods and ingredients. The food database 2000 could include information about other samples, substances or materials present in the environment, and their ingredients. For example, the food database 2000 could contain information about: (a) the lead content of a particular brand of lipstick; (b) the titanium dioxide coating of a caplets of a particular pharmaceutical; (c) contaminated air, water, animal food, soil, or building materials; (d) black mold on the walls of a particular home; or (e) the possible contamination of particular ground water with PCBs.

In some embodiments, the food database 2000 includes information about whether a food can be eaten raw, or about how the food should be prepared or cooked or stored. For example, such information can include the recommended cooking temperatures, recommended cooking times, recommended cooking methods (such as microwave, boiling, roasting, and frying), and/or recommended storage procedures, conditions and times. In some embodiments, the food database 2000 includes information about how the flavour, or the nutrient or toxin etc. content, of a food likely changes according to how the food is cooked, prepared, or stored.

In some embodiments, the food database 2000 includes information about the supply chain of foods and their ingredients. For example, such information could include (i) the town, city, county, state, province, country, and/or coordinates, in or at which the food or its ingredients was grown, aged, manufactured, prepared, and/or packaged; (ii) the farm, land, waters, building, and/or factory where the food or its ingredients was grown, made, raised, bottled, and/or processed; (iii) the mode, vehicles, shipping companies, shipping conditions, transshipment points, and/or shipping delays related to the shipping of the food from the location at which it was grown, made, raised, bottled and/or processed to the location at which the user took physical custody of the food; (iv) the owners of such farm, land, plant, factory, shipping companies etc., whether such owners are individuals or corporate entities, and the owners of, or investors in, such owners, including their nationality, labor practices, political contributions etc.; and (v) the other foods or ingredients that are grown or made or processed in such facilities. For example, such information could relate to the supply chain as a whole e.g. whether coffee is fair trade. For example, such information could relate to whether a farm, land, plant, factory, individual, corporation, or investor is American or American-owned, or the target of a boycott or other action by consumer or political activists. For example, such information about meat, poultry, eggs, milk, and other foods, can relate to declared or assessed grade or quality, the treatment of livestock (e.g. cage free, free range, or free run), the ingredients in the livestock feed (e.g. grass, antibiotics, growth hormones, or fish oil), the treatment of the soil (e.g. depletion of nutrients), whether or not the food is organic, or certified as such, and/or the chemicals used on the food, or on or in the associated air, water or soil. For another example, the food database 2000 can include photographs or videos of the farm, farmers, fishing boats, fishermen, etc. who grew the crops, raised the livestock, or caught the fish.

In some embodiments, the food database 2000 includes information about the variety of fruits, vegetables, meats, seafood, grains and oils, the biological origin of that variety, and whether or not that variety is GMO.

In some embodiments, the food database 2000 includes information about how foods are handled, shipped, and packaged, and the impact of such handling, shipping, and packaging on the foods. For one example, such information can include whether canned foods may have been contaminated with BPA or whether water in plastic bottles was subjected to heat and now may be contaminated with phthalates.

In some embodiments, the food database 2000 includes information about particular samples of foods. Examples include information related to: (i) freshness, ripeness, tenderness, quality, age, or sweetness, and how those qualities are expected to change with time; (ii) whether a food has begun to spoil, rot, separate, or dry out; (iii) what kinds of fungus, bacteria, or disease are or may be present in a food, and in what possible or likely quantities; (iv) whether cooked food has been under-cooked, over-cooked, burnt, or undergone undesired chemical or other processes; and/or (v) how much longer food can be stored before it should be discarded.

In some embodiments, the food database 2000 includes information that is mainly of specialized interest. Examples, without limitation, include the real or purported: curative or medicinal properties of foods; properties of food of interest to users who follow a particular alternative medicine; psychoactive or aphrodisiac properties of foods.

In some embodiments, the food database 2000 includes information related to the taste of a food, or a sample of a food, and in particular the its sweetness, sourness, saltiness, bitterness, and/or umami, measured quantitatively or qualitatively. In some such embodiments, the intensity of one or more of these potential taste sensations of a sample can be estimated partially with reference to scan data.

In some embodiments, the food database 2000 includes information related to the smell of a food, or a sample of a food. For example, such information can relate to volatilized chemical compounds, such as estimates of: (a) the intensity of odors, like musk, putrid, pungency, camphor, ether, floral and peppermint, of the food measured quantitatively or qualitatively; and/or (b) the concentration in the food of diacetyl, isoamyl acetate, benzaldehyde, cinnamic aldehyde, ethyl propionate, methyl anthranilate, limonene, ethyl decadienoate, allyl hexanoate, ethyl maltol, ethylvanillin, and/or methyl salicylate. This information can be partially in response to scan data.

In some embodiments, the food database 2000 includes information related to the texture or chemesthesis of a food, or sample of a food. For example, such information could include estimated quantity of: (a) capsaicin or capsaicinoids, and thus "hotness"; (b) piperine, for the pungency of pepper; (c) ATC, for the pungency of mustard and horseradish; or (d) allicin for the pungency of garlic. This information can be partially in response to scan data.

In some embodiments, the food database 2000 includes information that can be used to discriminate between wine or other alcoholic beverages from different vintages, or between types or varieties of cheeses or other aged, cured or preserved foods.

FIG. 21 illustrates a database of correlations between spectra, calculated in various ways.

The correlation database 2100 includes information about the correlations between spectra. In some embodiments, these spectra were obtained by the spectroscopes 101. In FIG. 21, the correlation database includes a row for various pairs of distinct spectra. The correlation database need not contain a row for every possible pair of distinct spectra. For example, if a row is present for a key A in column 1 and for a key B in column 2, then no row need be present for A in column 2 and B in column 1. In some embodiments, pairs of spectra obtained from samples of similar foods are more likely to have a row in the correlation database while pairs of spectra obtained from samples of dissimilar food are less likely to have a row in the correlation database.

For each pair of spectrum keys for which a row is present in the correlation database 2100, the correlations written, for example, in the 3rd, 4th, . . . columns of FIG. 21 are the n-dimensional Euclidean distances between the corresponding ortho spectra of the two spectra indexed by that pair of spectrum keys. That is, the entry in the 1st row and 3rd column of FIG. 21 might be the n-dimensional Euclidean distance between the ortho spectra written in the 1st and 2nd rows of FIG. 21 in the 5th column. The variable n in the phrase n-dimensional refers the length of the spectrum array, or the number of different indices or positions or offsets for which a magnitude (for example, a photon count), of the spectrum is given. In some embodiments, the correlations are dot products or distances under other metrics, such as the sup metric.

In some embodiments, for each given spectrum key A, for each "correlation column" or distinct kind of correlation recorded in the correlation database 2100, the database of spectra 2200 contains a field, whose entries are a list of spectrum keys B, ordered by the magnitude of the corresponding correlation between A and B. For example, the first entry in the list of spectrum keys for a particular spectrum key A and a particular kind of correlation, is that spectrum key B such that that correlation between A and B is largest.

FIG. 22 illustrates a database of spectra, including an identifier for the spectrum, an identifier for the user who obtained the scan, the date and time the scan was obtained, the raw spectrum, the various ortho spectra obtained after processing, and the food ID that was assigned to the scan.

The spectra database 2200 includes information about spectra. In some embodiments, these spectra have been obtained by spectroscopes 101. In FIG. 22, the spectra database includes a row for each spectrum recorded by a spectroscope 101. When the server 102 (and server system 401) receives a spectrum from a spectroscope 101, whether or not through a personal computing device 103, the system: (a) assigns and records a globally unique key to that spectrum, which is depicted in column 1 of FIG. 22; (b) assigns and records an identifier that uniquely identifies the user who obtained the scan, which is depicted in column 2; (c) records the date and time that the scan was made, which is depicted in column 3; (d) records the spectrum itself, which is the raw spectrum depicted in column 4; and (e) records the spectrum after it has been processed by the spectrum processing subsystem 403, which is depicted in column 5. The personal computing device 103 can have a feature, by which the current user of record of a spectroscope 101 can be changed, so that more than one person, such as the persons in a family, can use a single spectroscope.

The ortho spectra fields of the spectra database 2200 depicted in FIG. 22, contain the ortho spectra computed by the orthogonalizer at step 806 of FIG. 8, after input of the processed spectrum in the 5th column of FIG. 22, to the orthogonalizer, as written in step 807 of FIG. 8. These ortho spectra are calculated relative to reference spectra. The food ID field of the spectra database 2200 is written by the spectrum analysis subsystem in step 1008 of the process flow 1000.

In the context of the invention, there is no particular requirement that the spectra database 2200 be limited to information about Raman spectra. The spectra database 2200 can contain information about any spectra, as defined herein. For example, such spectra include fluorescence spectra, mass spectra, ion mobility spectra, transmission spectra etc.

Figure 23:
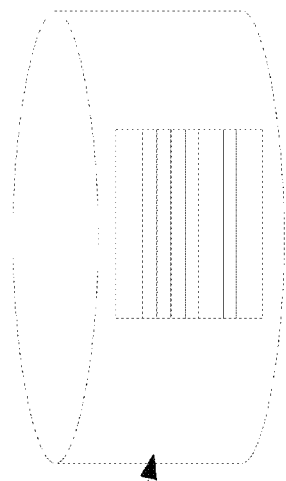
FIG. 23 illustrates a database of strategies for identifying and analyzing spectra, including the model generator, a rank, the local behavior expected, the best guess, the derivation used, the strategy depth, and the confidence level.

FIG. 23 illustrates a database of strategies for identifying and analyzing spectra, including the model generator, a rank, the local behavior expected, the best guess, the derivation used, the strategy depth, and the confidence level.

FIG. 23 depicts rows of the strategy database 2300 containing information about a particular strategy (M,B) where M is a model generator and B is a bit string. The fields in the first column of FIG. 23, entitled model generator, contain representations of the model generators M, which are arrays of functional computer programs. The fields in the second column contain integers indicating the order in which a particular strategy is applied in step 1005 of the process flow of the spectrum analysis subsystem 1000. The fields in the third column of FIG. 23 contain B, the particular bit strings that might be output by the action of the model mapper on a spectrum key and the model generators M. The fields in the fourth column represent the particular columns of correlations in the database of correlations 2100, which correspond to the model generators M, which are used by the strategy optimizer in writing the food ID of the closest spectrum to the input spectrum as the food ID of that spectrum. The fields in the fifth column of FIG. 23 contain data identifying the particular orthogonalization used by that column of correlations, and sufficient information to identify any additional processing done to spectra before the correlations are calculated. The fields in the sixth column contain numerical measures of the complexity of the model generator, such as, for example, the total length of a standard representation of the model generator M. The fields in the seventh column contain the confidence levels of the strategies, which for example can be computed at the time the ordered list of strategies is generated at step 1007 of the process flow 1000 depicted in FIG. 10, and can comprise an ordered pair, the first of which is the proportion of input spectra that are computed correctly, and the second of which is the number of input spectra computed correctly.

Presentation of Information to User

FIG. 24, FIG. 25, FIG. 26, and FIG. 27 depict user interfaces on a display 301 on a personal computing device as described herein, such as, for example, a smart phone, smart watch, a tablet, or personal computer. In these figures, the branding element 2401 is a rectangular area at the top of the display 301, which depicts the logo of the brand under which the service provided by the system 100 is provided.

In the figures, the information elements, text elements, and color elements, and their choice and placement, are responsive to: (a) information related to the sample 105 which was most recently scanned; (b) the outputs of the various programs, subsystems, and submodules in the server system 401; and/or, for example, (c) one or more inputs from the user 104; (d) collaborative filtering data; (e) information in the user profile database 1900 associated with the user 104, (f) pseudo-random or random values; and/or (g) other information or input or states. All of these information, inputs, outputs, data, values, and states can be used in combination or conjunction.

Figure 24:
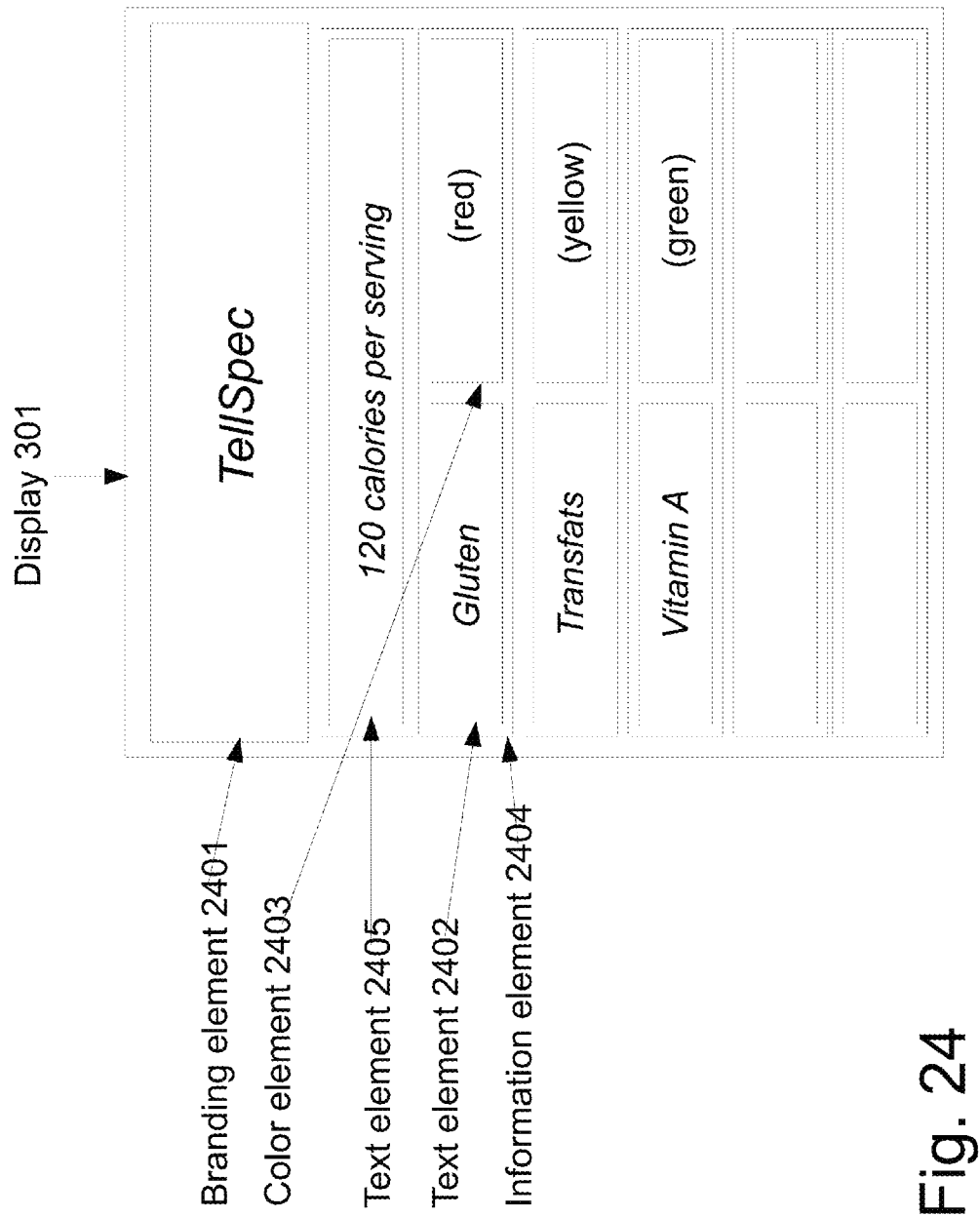
FIG. 24 illustrates a user interface, in which a list of facts and other elements containing information about a food are depicted.

FIG. 24 illustrates a user interface, in which a list of facts and other elements containing information about a food are depicted.

In FIG. 24, the area on the display 301 is partitioned into the branding element 2401 and (a) smaller rectangles extending the width of the display, containing text elements, and/or (b) two columns of smaller rectangles, the ones in the left column containing text elements and the ones in the right column containing color elements.

In FIG. 24, the text element 2405 extends substantially the full width of the display and depicts information on the number of calories per serving for the corresponding sample. In embodiments in which a method capable of estimating the volume of a sample is available, the text element 2405 can report the number of calories for the whole sample. In other examples, the text element 2405 can indicate: (a) the number of grams of fats, carbohydrates, and/or proteins present in one serving of the sample; or (b) the glycemic index of the sample.

In FIG. 24, the information element 2404 contains a text element 2402 and a color element 2403. The text element 2402 can indicate a food, ingredient, or chemical that may or may not be present in the sample, and the color element 2403 can be of a color that indicates the nature of the information about that food, ingredient, or chemical, its possible presence in the sample, and, if present, the estimated concentration of that food, ingredient, or chemical in the sample. For example, the color element may be green, yellow, or red where: a green color element indicates good news, like the presence of vitamins or the absence of preservatives; a yellow color element indicates a warning, like high sugar content, or the presence of a relatively benign preservative; and a red color element might indicate danger like the presence of carcinogens, allergens or toxins. Other schemes are workable and obvious.

In FIG. 24, the figures, the information elements, text elements, and color elements, and their choice and placement, are responsive to the output of the fact selecting program 1305 within the ranking subsystem 406 of the server system 401.

FIG. 25 illustrates a user interface that shows: suggestions of alternate foods, with higher personalized rankings; reasons for these suggestion; and built-in hyperlinks to information about these alternate foods.

In FIG. 25, the area on the display 301 is partitioned into the branding element 2401 and into smaller rectangular information elements 2501, 2502, 2503, 2504, . . . extending the full width of the display.

In FIG. 25, the information element 2501 extends substantially the full width of the display and suggests an alternative A to a sample B. In some embodiments, the foods A and B are both stock-keeping units (SKUs) in food stores, and the alternative A is described so that that alternative A can be easily located in a food store, for example in a manner useful to a user who is shopping at that time in that food store.

In FIG. 25, the information element 2502 indicates a reason why the user may prefer to try food A instead of food B. For example, the information element 2502 can indicate: (a) that a particular vitamin is present in food A at a greater concentration than it is in food B; or (b) that food A does not have preservatives while food B does contain preservatives.

In FIG. 25, the choice and placement of the text elements 2501, 2502, . . . are responsive to the outputs of the food recommendation program 1306 within the ranking subsystem 406 of the server system 401.

Figure 26:
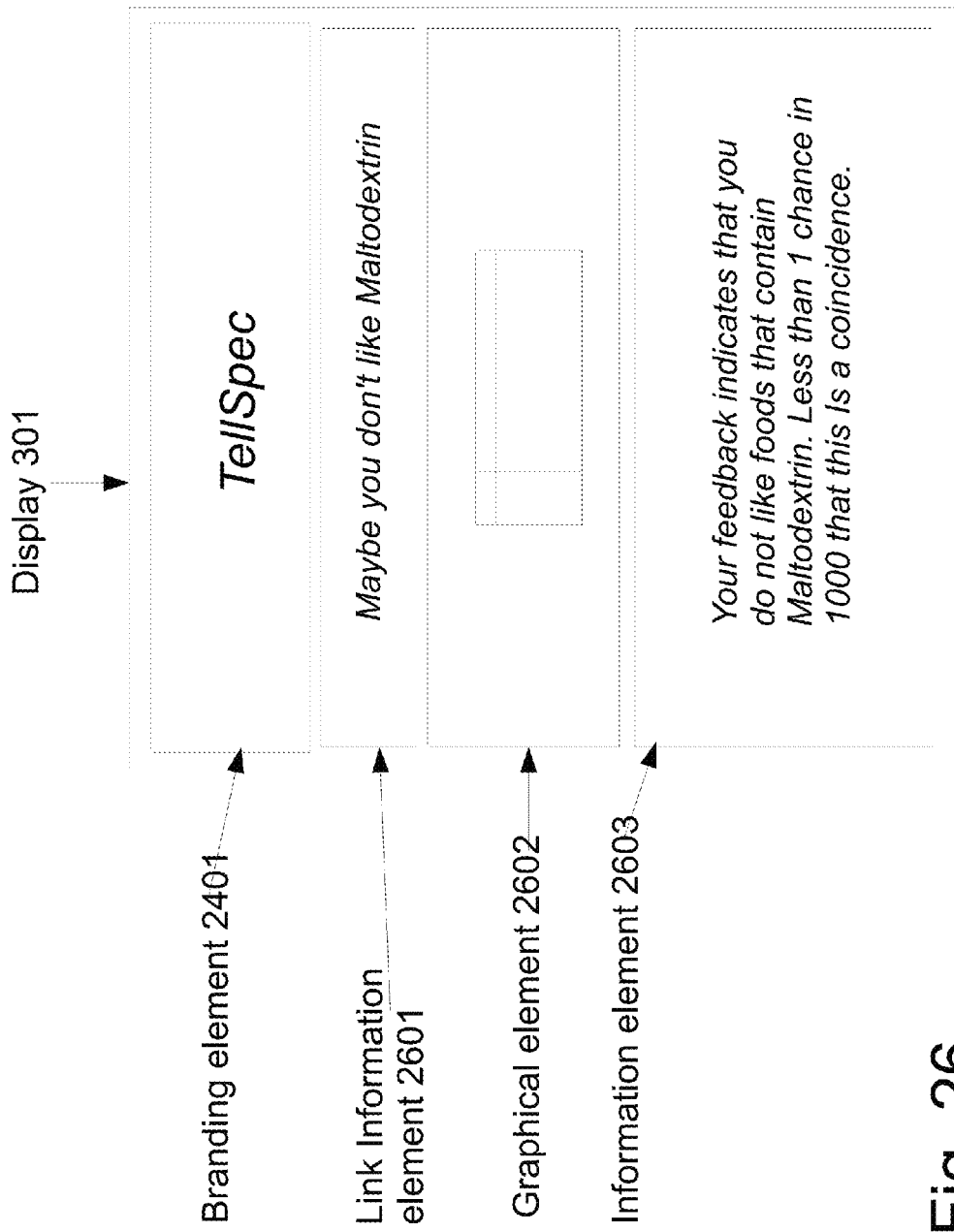
FIG. 26 illustrates a user interface, in which a possible problem food is shown, a confidence level, reasons for suspicion including a graphical representation, possible underlying reasons, and built-in hyperlinks to information about the possible problem food.

FIG. 26 illustrates a user interface, in which a possible problem food is shown, a confidence level, reasons for suspicion including a graphical representation, possible underlying reasons, and built-in hyperlinks to information about the possible problem food.

In FIG. 26, the area on the display 301 is partitioned into the branding element 2401 and into smaller rectangular information and graphical elements 2601, 2602, 2603, . . . extending substantially the width of the display.

In FIG. 26, the information element 2601 reports a possible problem food P for the user. For example, the food P may be a chemical, like sodium benzoate, or a class of chemicals, like gluten, and is given the name that is commonly used to describe it on ingredients labels or in layman media.

In FIG. 26, the information element 2603 reports a particular suspected problem food P, and some information related to the reason that the link detection subsystem has determined that this food P may be a problem for the user. Such information can include, for example: the user's dislike of food that contains P, based on user feedback about whether the user found foods containing P to be tasty; or allergic, intolerance, or other undesired reactions contemporaneous with, or immediately after, the user's ingestion of food containing P, based on user feedback about feelings of well-being after meals in which the user ingested foods P.

In FIG. 26, the graphical element 2602 presents a graphical image that represents, or otherwise contains information about, the correlation between the food consumption by the user over time that was compiled in step 1604 and the passive personal log data or other data related to the user over time that was compiled in step 1603, related to the evaluation of linkage over time at step 1605 and/or the finding of a possible link at step 1607, in the process flow of the link detection system 407.

In FIG. 26, the information and graphical elements 2601, 2602, 2603 . . . , are responsive to the operation of the link detection system 407. The choice and placement of the elements 2601, 2602, 2603 . . . are responsive to the possible links found at step 1607 of the process flow of the link detection subsystem within the server system 401.

In FIG. 26, the information element 2603 presents information related to the correlation between the food consumption by the user over time that was compiled in step 1604 and the passive personal log data or other data related to the user over time that was compiled in step 1603, the evaluation of linkage over time at step 1605 and/or the finding of a possible link at step 1607, in the process flow of the link detection system 407. For example, the information element 2603 can provide an estimate of the odds or probability or confidence level that this link is just a coincidence.

FIG. 27 illustrates a user interface, through the use of which the user can input information about the user's current health and well-being, presented as a linear scale.

In FIG. 27, the area on the display 301 is partitioned into the branding element 2401 and smaller rectangular information elements 2701, 2703, 2705, and graphical input elements 2702, 2704 . . . .

In FIG. 27, the information element 2701 extends the full width of the display and presents a question for the user about his/her state of well-being. For example, the question can ask about the user's general well-being, digestion, headaches, energy level, libido, asthma, joint pain, depression, ear, noise and throat, acid reflux, feeling of being bloated, hives, running nose, ability to concentrate, alertness, or about some other aspect of their health, sensations, or feelings. For example, the question can be asked at a particular time of each day, such as bedtime, noon, or at waking time, or at the start and/or end of each meal.

In FIG. 27, the graphical input elements 2702 and 2704 provide a range of spatial positions on the display 301 that the user can touch or click on to indicate the user's particular answer to the question presented in information element 2701. The information elements 2703 and 2705 present words or symbols that describe the possible particular answers to the question, parallel to, in simulation of, and/or beside or opposite to, graphical input elements 2702 and 2704. For example, with reference to FIG. 27, a user touching graphical input element 2704 in the center indicates that they are answering the question "How do you feel today?" with the answer "so-so".

In FIG. 27, the information elements 2701, 2703, 2705 . . . , are responsive to the operation of the user profile subsystem 405. The choice and placement of the text elements 2701, 2702, 2703 . . . are responsive to the data in the user profile database within the user profile subsystem 405. For example, a user that indicates a possible allergy to gluten can be asked questions about their digestion or gastric or intestinal comfort, while a user that indicates a frequent feeling of fatigue can be asked questions about energy level or alertness or ability to concentrate.

Motivating Users

In some embodiments, the presentation of information includes information related to the actions by, presentations to, and/or user interaction of, other users, and/or interpretations by the system thereof. For example, a "what's happening now" page can show the foods that other users have scanned, the suggestions presented by the system to those users, choices or changes in choices (switches) made by those users (for example, as evidenced by the use of a coupon). In some embodiments, the information presented to a user is selected so that the information is relatively interesting to that user. In one example, a user A is presented with information about choices, or changes in choices, by other users B, that are related to whatever the user A is scanning or perusing at that time. In another example, when the user scans a food, the system presents a suggestion of a food chosen by others who had also scanned that food or a similar food. In a specific example, when a customer scans Brand A Hot Sauce, the system can present a report that another customer switched from Brand A Hot Sauce to Brand B Hot Sauce, which has a higher rank or which has fewer preservatives. In another specific example, the system presents the information that-"John is considering Brand C Potato Chips instead of Brand D Potato Chips" or "John just scanned Brand E White Bread and is now reading about calcium peroxide" or "people who scan Brand C Potato Chips also tend to scan Brand D" or "Brand G Breads most scanned food is Garlic Baguette" or "Mary just read about vitamin B1". In some embodiments, information about users can be anonymized to respect each user's privacy setting or the privacy laws of various jurisdictions. For example, users can be referred to as "Mary" or "Mary in Chicago" or "Jane, a lawyer in Palo Alto" or "Dr. A in Norfolk, Va.".

In some embodiments the system presents a suggestion to the user that the user choose food B as an alternate to food A: (a) when food B has a higher personalized rank than food A for that user; (b) when food B is similar to food A in response to some measure of similarity of foods; (c) when this suggestion is made in response to the actions (for example, recommendations or choices) of other users, possibly to other similar users; and/or (d) when this suggestion is made in response to information related to the fact that a company wishes to promote sales of food B.

In some embodiments, users can scan a food A, and provide input to the system, that indicates that food A is a replacement for another food B for that user where (a) the user may or may not have scanned food B previously; and (b) the system may or may not have previously presented a suggestion of food B to the user. In some embodiments, users can scan a food A, and the system can decide, in response to data in the user profile database, that food A is a replacement for another food B, that the user may or may not have scanned previously. The choice of food A as a replacement for food B by a user can be recorded by the system as an "accomplishment" of that user.

In some embodiments: (a) if a first user offers a suggestion that other users choose food A as an alternate to food B, and a second user indicates that, or it is attributed by the system that, the second user has chosen food A as an alternate to food B, then this choice can be recorded as an accomplishment of the first user (and/or of the second user); and/or (b) if a first user offers a suggestion that users choose food A, not necessarily as an alternate, and a second user indicates that, or it is attributed by the system that, the second user has chosen food A, possibly as an alternate to food B, then this choice can be recorded as an accomplishment of the first user (and/or of the second user).

In some embodiments, the aforementioned accomplishments can contribute towards the completion of "portfolios" of possible accomplishments. For example, the system can present the user with a portfolio of "bad" foods, and recommendations of possible "better" alternates that the user might consume instead. For another example, the system can present the user with a portfolio of "good" foods, and recommendations that the user try them. For another example, the system could present the user with a portfolio of "rare" foods (including dishes prepared at home or at a restaurant) for which the system needs further data, and request that the user scan them. Some portfolios could be standard for many or all users, and other personalized portfolios could be generated dynamically for each user, and the like.

In some embodiments, some portfolios focus on: (a) particular classes of food e.g. green vegetables or mushrooms or red wine, and/or present only foods that are reasonably available to the user; (b) particular kinds of ingredients, for example processed sugars, starches, proteins and oils; (c) reaching a recommended weekly consumption of vitamins; (d) reducing the user's consumption of preservatives or other additives, or carcinogens, metals, or toxins; and/or (e) reaching a desired consumption of protein, as a percentage of total caloric intake. Examples include a mushroom portfolio that suggests that the user try ten different varieties of mushrooms, available to that user in local stores, and that offers suggestions on where to get them, and how to prepare them, and a portfolio that focuses on reducing the user's consumption of such processed sugars, starches, proteins and oils by 20%, and contains ten suggestions, which, if followed, would achieve this goal.

In some embodiments, some portfolios for a first user focus on accomplishments related to consumption by other users. Such "altruistic" portfolios can include goals such as, for example: (a) making suggestions that are subsequently followed by ten other users, as a result of which each such other user's daily sugar intake is lowered by 10 g; or (b) recommending a healthy food, that is then tried by ten other users as alternates to other foods that are less healthy for those users.

In some embodiments, some portfolios focus on adding content such as recipes, photographs, videos, stories, or reviews. Such "content" portfolios can include goals such as, for example, providing ten photographs of varieties of cheese, or receiving ten endorsements for a recipe that uses kale, or getting one hundred views for a video showing the preparation of a dish high in minerals and vitamins.

In some embodiments, a first user making an accomplishment credits a second user with thanks (and credit) for their accomplishment. In one example, the second user writes an interesting review of a food or a compelling story about their own experience, or takes an appetizing photograph of a food, and a first use makes an accomplishment, for which they were they inspired by that review, story, or photograph.

In some embodiments, when a user completes a portfolio, the user receives some public or private acknowledgment or "reward" for this. Examples of such acknowledgements or rewards include: (a) a badge or award that appears on that user's personal webpage, possibly visible to other users; (b) a tweet or email that is sent to some other users that reports that the user has completed this portfolio; (c) the raising of one or more "levels" of a user, say from level 14 to level 15, so that upon reaching a certain level, say level 20, that user gets the status of a "guru" or "expert" or "benefactor" or gets membership in an exclusive club like "vitamin advisory group"; (d) a virtual trading card, where these trading cards are responsive to the particular portfolio completed and/or random or pseudo-random values, so that certain trading cards could be relatively common, and others relatively rare, and a user who accumulates certain combinations of trading cards can receive additional badges, levels, or status, or coupons, or gift certificates or contributions to charities in their name.

In some embodiments, accomplishments can be measured quantitatively in terms of estimated health impact. For example, accomplishments could be associated with a quantity of microlifes, where one microlife is a unit of risk representing half an hour change of life expectancy, so that choosing one slice of whole grain bread as an alternate to two slices of white bread for one week might add an estimated 1 microlife to the user. In some embodiments, accomplishments can be associated with estimated minutes of increase of life expectancy, so that the same change in bread choice could add 30 minutes of life expectancy. In some embodiments, the system can credit users with the estimated amount of time by which an accomplishment has extended their life expectancy, or with the estimated amount of time by which that user's suggestions has extended the life expectancy of other users who acted on those suggestions. Other possible numerical values could include healthy life expectancy (HALE), healthy life years (HLY), or quality-adjusted life year (QALY).

In embodiments in which users can recommend foods or recipes to other users or contribute photographs, videos, stories or reviews related to food, users receive reports as to how many other users followed their recommendations, tried their recipes, viewed their photographs or videos, or read their stories or reviews. In some such embodiments, users can receive summary information such as the estimated amount of time they have added to their own life expectancy or to the life expectancy of others, for example, each month or each week.

In some embodiments, users are encouraged to scan by being rewarded for eating good foods, rather than penalized for eating too much, or eating the wrong foods. For example, accomplishments could be usually based on scanning a food, and rather than on not scanning a food.

In some embodiments, users can compare themselves against other users. For example, users can see themselves on a scoreboard with, and compared to, some other users, and those other users might be similar users chosen so as to place the user in the psychologically most compelling position—such as second last place on the scoreboard, and some of those users might be replaced from time to time by other users so as to preserve this relative position.

In some embodiments, users can create groups within the community of users with specialized interests like types of yogurt, or vitamins, or gluten allergy, or migraines.

Those of ordinary skill in the art will recognize, after perusal of this application, that the invention, makes it possible to build a worldwide ubiquitous food, human, and environment monitoring system. With this system, data can be gathered from many times and places related to food, humans, and the environment, including, without limitation, medical, psychological, genetic, geographical, dietary, and/or activity data, related to inputs, outputs, states and/or performance; and, with this system, this data can be analyzed and correlated, and things (e.g inputs, outputs, states and/or performance) and properties of things can be estimated and/or determined, and statistical relationships between those things and properties of things can be estimated and/or determined. The embodiments given herein are illustrative and in no way limiting, and that many variations are workable which remain within the concept, scope, and spirit of the invention.

The invention claimed is:

1. A method comprising: obtaining a first set of one or more spectral scans relating to a first sample of food from a handheld device associated with a user; analyzing spectral information included in the first set of one or more spectral scans using a plurality of program models to generate a corresponding plurality of program outputs, the program models of the plurality of program models comprising machine-learning programs that use a second set of a plurality of spectral scans related to a second sample of food substantially similar in composition to the first sample of food in connection with generating the plurality of program outputs;

determining nutritional composition information of the first sample based on at least one program output of the plurality of program outputs, the at least one program output being selected from the plurality of program outputs based, at least in part, on a calculated confidence associated with the at least one program output;

and sending a response to the handheld device associated with the user, the response comprising the nutritional composition information;

wherein the method further comprises: receiving first feedback information from the user comprising a first relative state of health of the user following consumption of the first sample of food; referencing second feedback information from the user relating to at least a third sample of food, the third sample of food being substantially similar in composition to the first sample of food, the second feedback information comprising a first relative state of health of the user following consumption of the third sample of food;

determining, based on a comparison of the first feedback information and the second information, that the first feedback information and the second feedback information are similar at least in part; and sending an indication to the handheld device associated with the user comprising a correlation between the first sample of food and the first relative state of health.

2. The method of claim 1 further comprising:
selecting possible actions by the user based on the nutritional composition information, the possible actions relating to an improvement of nutrition of the user,
wherein the response further comprises an indication of the possible actions.

3. The method of claim 1 further comprising:
selecting a group of users and creating a scoreboard shown to the user,
wherein one or more scores of the scoreboard are responsive to completion by users of the possible actions; and
the group of users is chosen so that at least one of the following is verified:
(a) the users in the group of users are similar; or
(b) the user has a score less than the median score of the group of users.

4. The method of claim 1 further comprising, wherein the first set of one or more spectral scans comprise near-infrared spectral scans.

5. The method of claim 1, wherein the nutritional composition information comprises at least one of a glycemic index associated with the first sample, a glycemic load, a caloric content associated with the first sample, a sodium content of the first sample, a fat content of the first sample, a protein content of the first sample, a carbohydrate content of the first sample, a pesticide content of the first sample, one or more allergens included in the first sample, a carcinogen content of the first sample, and one or more contaminants included in the first sample.

6. The method of claim 1, wherein the plurality of program models further comprise at least one of statistical-learning programs and chemometric analysis programs.

7. The method of claim 1, wherein the method further comprises determining a volume of the first sample and wherein determining the nutritional composition information is based, at least in part, on the at least one program output and the determined volume.

8. The method of claim 7, wherein determining the volume of the first sample comprises determining the volume of the first sample based, at least in part, on volume information provided by the user.

9. The method of claim 7, wherein determining the volume of the first sample comprises determining the volume of the first sample based, at least in part, on at least one photograph of the first sample provided by the user.

* * * * *